(12) United States Patent
Skeele et al.

(10) Patent No.: US 10,603,469 B2
(45) Date of Patent: Mar. 31, 2020

(54) MEDICAL DRESSING HAVING A TIMER

(71) Applicant: Harris Skeele Corporation, Manlius, NY (US)

(72) Inventors: Trina A. Skeele, Manlius, NY (US); Sherod V. Harris, Syracuse, NY (US)

(73) Assignee: Harris Skeele Corporation, Manlius, NY (US)

( * ) Notice: Subject to any disclaimer, the term of this patent is extended or adjusted under 35 U.S.C. 154(b) by 0 days.

(21) Appl. No.: 16/171,928

(22) Filed: Oct. 26, 2018

(65) Prior Publication Data

US 2019/0060615 A1 Feb. 28, 2019

Related U.S. Application Data

(63) Continuation of application No. 15/405,720, filed on Jan. 13, 2017, now Pat. No. 10,112,032.

(60) Provisional application No. 62/279,247, filed on Jan. 15, 2016.

(51) Int. Cl.
| | |
|---|---|
| *G08B 1/00* | (2006.01) |
| *A61M 25/02* | (2006.01) |
| *A61M 25/00* | (2006.01) |
| *G04F 3/06* | (2006.01) |

(52) U.S. Cl.
CPC ........ *A61M 25/02* (2013.01); *A61M 25/0017* (2013.01); *G04F 3/06* (2013.01); *A61M 2025/024* (2013.01); *A61M 2025/026* (2013.01); *A61M 2025/028* (2013.01); *A61M 2025/0266* (2013.01); *A61M 2205/276* (2013.01); *A61M 2205/33* (2013.01)

(58) Field of Classification Search
CPC ............ A61M 2025/024; A61M 25/02; A61M 25/0017; A61M 2205/33; A61B 2090/0803; G04F 1/005; G04F 3/06
USPC .............................. 340/309.7, 573.1, 539.12
See application file for complete search history.

(56) References Cited

U.S. PATENT DOCUMENTS

| | | | |
|---|---|---|---|
| 4,057,066 A | 11/1977 | Taylor | |
| 4,229,813 A * | 10/1980 | Lilly ...................... | G04F 13/06 116/206 |
| 4,408,557 A | 10/1983 | Bradley et al. | |
| 4,460,356 A | 7/1984 | Moseley | |

(Continued)

FOREIGN PATENT DOCUMENTS

| | | |
|---|---|---|
| EP | 0408389 B1 | 9/1994 |
| EP | 2460548 A1 | 6/2012 |

(Continued)

OTHER PUBLICATIONS

IIC AG; Innovative Packaging; Timestrip®; On or before Dec. 31, 2011; retrieved from the Internet: <http://www.iic-ag.com/timestrip/products/time-monitoring/>; 2 pages.

(Continued)

*Primary Examiner* — Toan N Pham
(74) *Attorney, Agent, or Firm* — Barclay Damon LLP

(57) ABSTRACT

A medical dressing is disclosed herein. The medical dressing, in an embodiment, includes a body and a see-through surface supported by the body. The medical dressing also includes a timer coupled to the body. The timer includes a structure configured to track the passage of time based on liquid diffusion or otherwise without relying on a battery or electrical power source.

21 Claims, 55 Drawing Sheets

(56) References Cited

U.S. PATENT DOCUMENTS

| | | | |
|---|---|---|---|
| 4,629,330 A | 12/1986 | Nichols | |
| 4,701,162 A | 10/1987 | Rosenberg | |
| 4,726,716 A | 2/1988 | McGuire | |
| 4,903,254 A | 2/1990 | Haas | |
| 5,259,838 A | 11/1993 | Taylor et al. | |
| 5,785,354 A * | 7/1998 | Haas | G04F 1/00 283/114 |
| 5,944,696 A | 8/1999 | Bayless et al. | |
| 6,121,565 A | 9/2000 | Allott, III | |
| 6,269,764 B1 | 8/2001 | Adamy et al. | |
| 6,436,073 B1 | 8/2002 | Von Teichert | |
| 6,701,864 B2 | 3/2004 | Watson, Jr. et al. | |
| 7,090,660 B2 | 8/2006 | Roberts et al. | |
| 7,215,604 B2 | 5/2007 | Haas et al. | |
| 7,280,441 B2 * | 10/2007 | MacDonald | A61F 13/42 116/206 |
| 7,372,780 B1 * | 5/2008 | Braunberger | G04F 13/04 116/206 |
| 7,434,535 B2 | 10/2008 | Adamy | |
| 7,766,870 B2 | 8/2010 | Dabbs | |
| 7,785,299 B2 | 8/2010 | Crawford et al. | |
| 7,817,498 B1 | 10/2010 | Hinckley | |
| 8,162,922 B2 | 4/2012 | Sacco et al. | |
| 8,500,698 B2 | 8/2013 | Kyvik et al. | |
| 8,801,671 B2 | 8/2014 | Müller et al. | |
| 2004/0240324 A1 | 12/2004 | Isbitsky et al. | |
| 2006/0247574 A1 | 11/2006 | Maule et al. | |
| 2007/0219500 A1 | 9/2007 | Wright et al. | |
| 2009/0216197 A1 | 8/2009 | Russo | |
| 2009/0259178 A1 | 10/2009 | Brechbuehler et al. | |
| 2010/0179482 A1 | 7/2010 | Wright et al. | |
| 2011/0071482 A1 | 3/2011 | Selevan | |
| 2012/0041378 A1 | 2/2012 | Bierman | |
| 2012/0089129 A1 | 4/2012 | Engelhardt | |
| 2012/0172846 A1 | 7/2012 | Nakamoto et al. | |
| 2012/0232490 A1 | 9/2012 | Andino | |
| 2012/0271237 A1 | 10/2012 | Andino | |
| 2012/0330255 A1 | 12/2012 | Carlin | |
| 2013/0079723 A1 * | 3/2013 | Andino | G04F 1/005 604/180 |
| 2013/0218107 A1 | 8/2013 | Aydelotte | |
| 2014/0081206 A1 | 3/2014 | Mueller et al. | |
| 2014/0228807 A1 | 8/2014 | Hart | |
| 2015/0109135 A1 | 4/2015 | Sandock | |
| 2015/0343173 A1 | 12/2015 | Tobescu et al. | |
| 2016/0136356 A1 | 5/2016 | Ribble et al. | |

FOREIGN PATENT DOCUMENTS

| | | |
|---|---|---|
| GB | 2454203 A | 5/2009 |
| WO | 2002006904 A1 | 1/2002 |
| WO | 200239196 A1 | 5/2002 |
| WO | 2007027216 A3 | 3/2007 |
| WO | 2012027342 A1 | 3/2012 |
| WO | 2014100906 A1 | 7/2014 |

OTHER PUBLICATIONS

IIC AG; Innovative Packaging Timestrip; Sep. 1, 2015; retrieved from the Internet: <http://web.archive.org/web/20150901203001/http://www.iic-ag.com/timestrip/>; 4 pages.

Timestrip Healthcare; Oct. 17, 2015; retrieved from the Internet: <http://web.archive.org/web/20151017093707/http://timestrip.com/industries/healthcare/>; 6 pages.

TimestripIV; TimeStrip Plc; Mar. 9, 2009; 2 pages.

Timestrip® Time indicators; On or before Nov. 30, 2014; 2 pages.

PCT/US17/13406; International Filing Date Jan. 13, 2017; International Search Report and Written Opinion; dated Apr. 4, 2017; 12 pages.

EP 17739032.5; filed Jan. 13, 2017; Extended European Search Report; dated Aug. 7, 2019 (7 pages).

* cited by examiner

MEDICAL DRESSING HAVING A TIMER

CROSS-REFERENCE TO RELATED APPLICATIONS

This application is a continuation of, and claims the benefit and priority of, U.S. patent application Ser. No. 15/405,720 filed on Jan. 13, 2017 (now U.S. Pat. No. 10,112,032), which is a non-provisional of, and claims the benefit and priority of, U.S. Provisional Patent Application No. 62/279,247 filed on Jan. 15, 2016. The entire contents of such applications are hereby incorporated by reference.

BACKGROUND

According to standards of care in the healthcare industry, certain medical articles are to be placed in use for no more than a designated usage period. For example, in-dwelling catheters are supposed to be removed and replaced periodically to avoid infection. The Foley urinary catheter, for example, is supposed to be replaced a designated number of days after placement. Other types of medical articles, such as breathing tubes, feeding bags and blood transfusion filters, have other designated usage periods.

The failure to replace a medical article when its usage period expires, poses significant health risks for the patient. Specifically, this failure can cause hospital-acquired infections (HAIs). In the case of urinary applications, this failure can cause urinary tract infection (UTI) or catheter-associated urinary tract infection (CAUTI). UTI is the single most common HAI, and the majority of cases of hospital-acquired UTI are associated with an indwelling urinary catheter. The consequences of these infections can include prolonged illness, the onset of new medical conditions, injury or death.

Attempts have been made to properly manage the usage periods of deployed medical articles. For example, clinicians are known to attach tags to medical articles and write dates and times on the tags. Other known attempts involve timers that are attachable to medical articles.

These attempts, however, have several shortcomings. Hospitals can be high-paced environments, especially in the areas relating to surgery, including the pre-operative, peri-operative and post-operative phases. It can be burdensome to require clinicians to physically write times on tags. Also, hand writing can be illegible, leading to inaccurate time tracking information.

Furthermore, use of the known tag and timer can be relatively complex. For example, the use of the known tag and timer requires several implementation steps. The clinician must attach the tag or timer to the medical article. Then, the clinician must manually write the time on the tag. When every second is a precious commodity in high-paced medical environments, the burden of these tasks can have a significant disadvantage, requiring too much time to implement the tag or timer.

In addition, the time pressures on clinicians can lead some of them to intentionally tamper with the known tag or timer. For example, to avoid the time necessary to replace a medical article, a clinician might wrongfully mark-out or change the time information written on the known tag to make it appear as if the usage period has not expired. Likewise, when the timer of a medical article shows an expired usage period, a busy clinician might wrongfully keep the medical article in use while replacing its timer with a new timer. The new timer would falsely indicate an unexpired usage period for the medical article. This type of tampering or wrongdoing can lead to the health risks and infections described above. The tamper vulnerability and complexities of the known tag and timer can frustrate the adoption and implementation of time-tracking practices by the medical community.

The foregoing background describes some, but not necessarily all, of the problems, disadvantages and shortcomings related to the known management of usage periods of medical articles.

SUMMARY

In an embodiment, a medical timing device includes: (a) a body including a first lock member, wherein the body defines an article-receiving space configured to receive an article portion of a medical article; (b) a timer coupled to the body, wherein the timer is configured to indicate an in-use time of the medical article; (c) a triggering element; and (d) a retainer coupled to the triggering element. The retainer is moveably coupled to the body, and the retainer is configured to be moved from an open position providing access to the article-receiving space to a closed position blocking at least part of the article-receiving space. The retainer includes second lock member, and the retainer is configured so that, in response to a single action of moving the retainer from the open position to the closed position: (i) the triggering element activates the timer to initiate a process to indicate the in-use time of the medical article; and (ii) the triggering element causes the second lock member to become locked together with the first lock member to lock the retainer in the closed position after the article portion has been inserted in the article-receiving space. The locked retainer is configured to keep the medical timing device coupled to the article portion even after the timer may indicate that the medical article has been used for more than a designated usage period. This inhibits the wrongful removal of the medical timing device from the article portion.

In another embodiment, the medical timing device including: (a) a body; (b) a timer coupled to the body, wherein the timer is configured to be activated so as to indicate in-use time of a medical article; (c) a retainer moveably coupled to the body; (d) a lock condition in which the retainer is moved relative to the body so as to lock the body to an article portion of the medical article; (e) an activation condition in which the timer is activated; and (f) a multi-condition trigger coupled to the body. In response to a single action applied to the multi-condition trigger, the multi-condition trigger is configured to cause both the lock condition and the activation condition to occur simultaneously or sequentially.

Yet another embodiment includes a method to facilitate monitoring an in-use time of a medical article. The method includes the following steps: (a) providing a body; (b) providing a timer, wherein the timer is configured to be activated so as to indicate in-use time of a medical article; (c) coupling the timer to the body; (d) providing a retainer; and (e) moveably coupling the retainer to the body, wherein the retainer is moveable relative to the body so as to lock the body to an article portion of the medical article. The retainer is configured so that, in response to a single action that moves the retainer relative to the body, the timer is activated and the article portion is locked to the body. The timer activation and locking can occur simultaneously or sequentially.

Additional features and advantages of the present disclosure are described in, and will be apparent from, the following Brief Description of the Drawings and Detailed Description.

DETAILED DESCRIPTION

The present disclosure relates to multiple embodiments of a medical timing device configured to be secured to a medical article, including, but not limited to, a catheter (e.g., a Foley urinary catheter, venous catheter or arterial catheter), feeding tube, breathing tube, corrugated ventilation tube, endotracheal tube, tracheostomy tube, ventilation circuit, catheter insertion dressing, feeding bag component of medical equipment (e.g., ventilator or respirator), such as a blood transfusion filter of a blood transfusion machine, and other types of medical articles.

In addition, the present disclosure relates to multiple embodiments of various medical devices that incorporate the medical timing device. For example, as described below, a catheter securement device can incorporate the medical timing device. Such catheter securement device is operable to anchor the catheter to the patient's skin while also tracking and indicating the usage period of the catheter.

Figure 1:
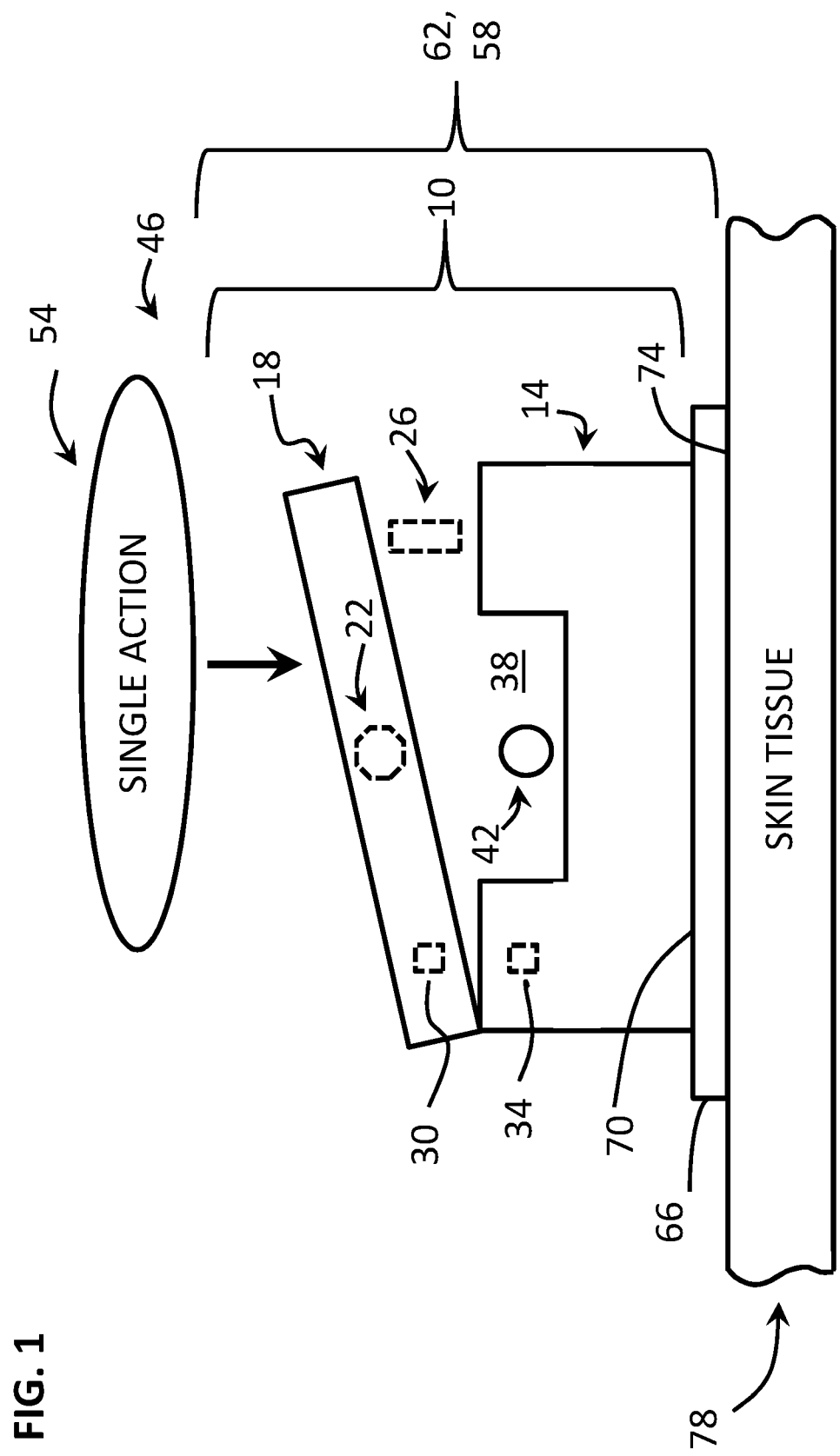
FIG. 1 is a side diagrammatic view of an embodiment of a medical timing device, an embodiment of a medical device and an embodiment of a catheter securement device, illustrating the open or unlocked position.
Figure 2:
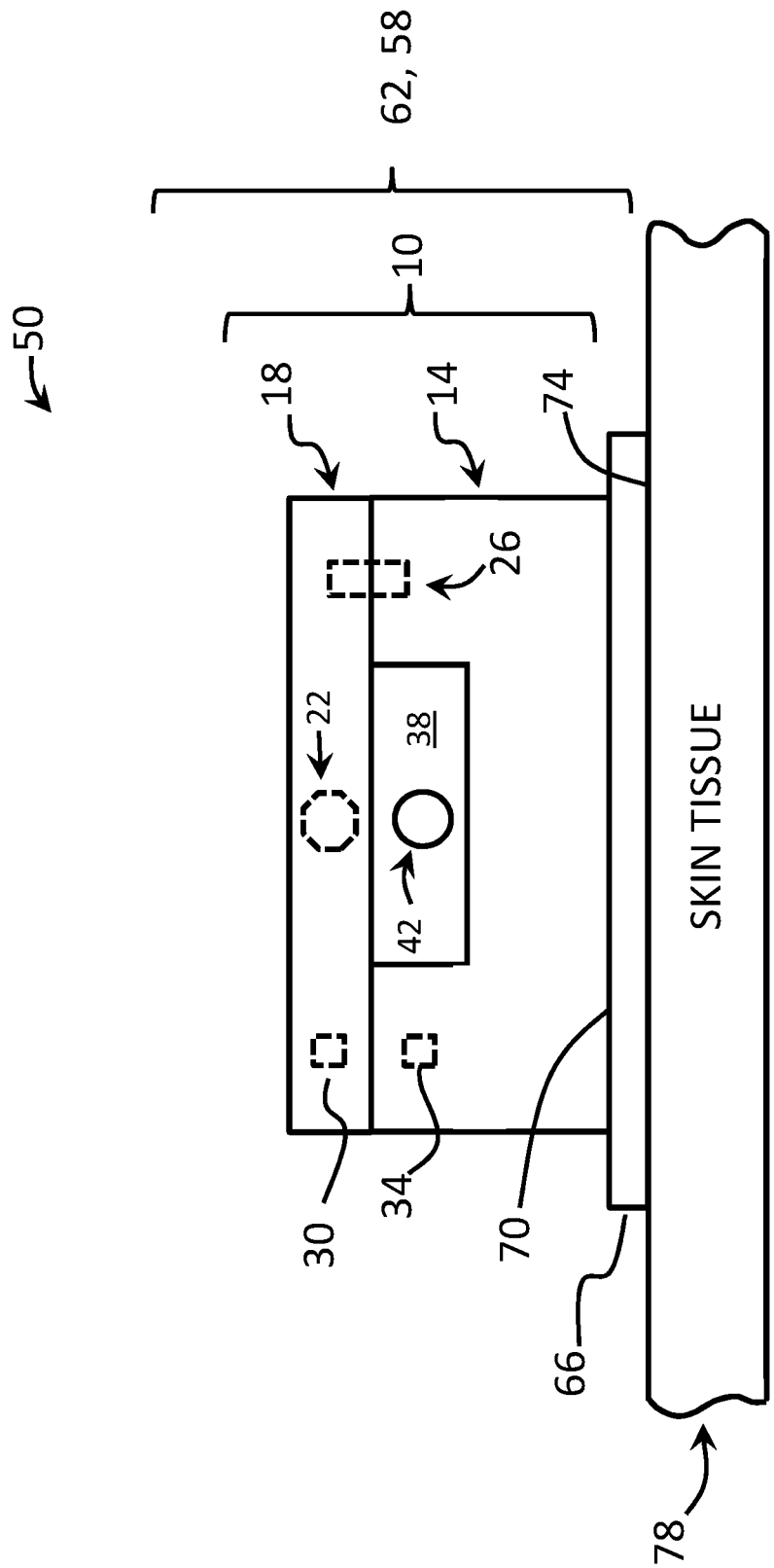
FIG. 2 is a side diagrammatic view of the medical timing device, medical device and catheter securement device of FIG. 1, illustrating the closed or locked position.
Figure 3:
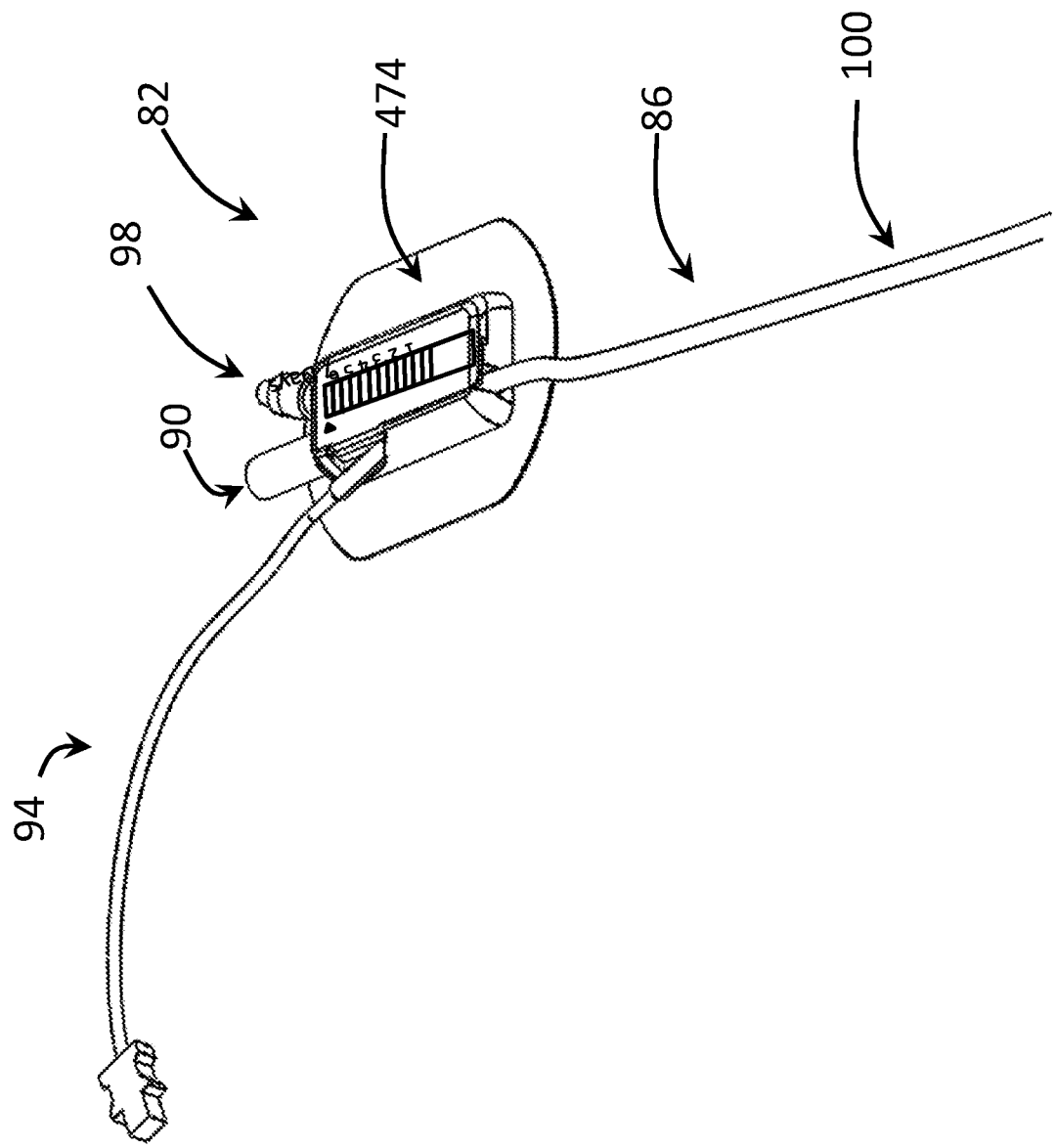
FIG. 3 is a top, front isometric view of an embodiment of a catheter securement device locked onto a urinary catheter, illustrated in the closed or locked position.
Figure 4:
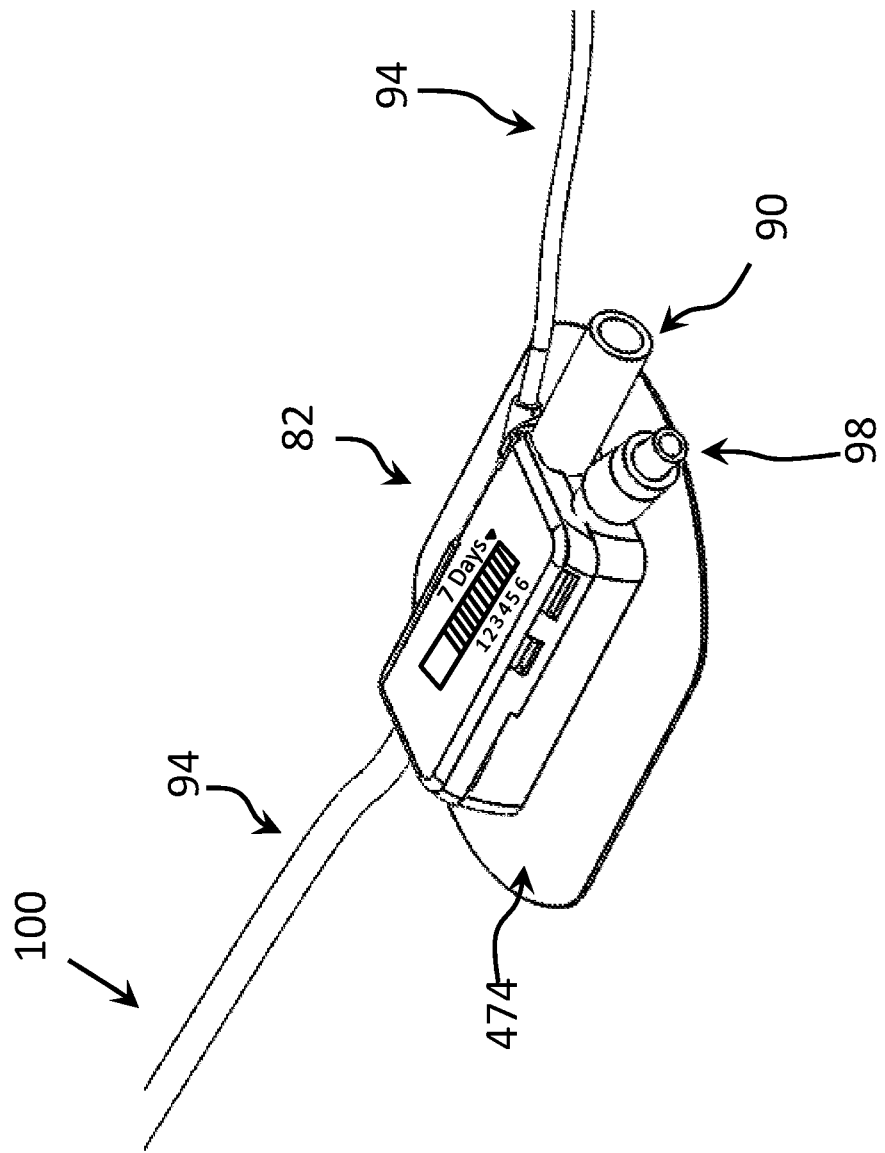
FIG. 4 is a top, rear isometric view of the catheter securement device of FIG. 3 locked onto the urinary catheter, illustrated in the closed or locked position.
Figure 5:
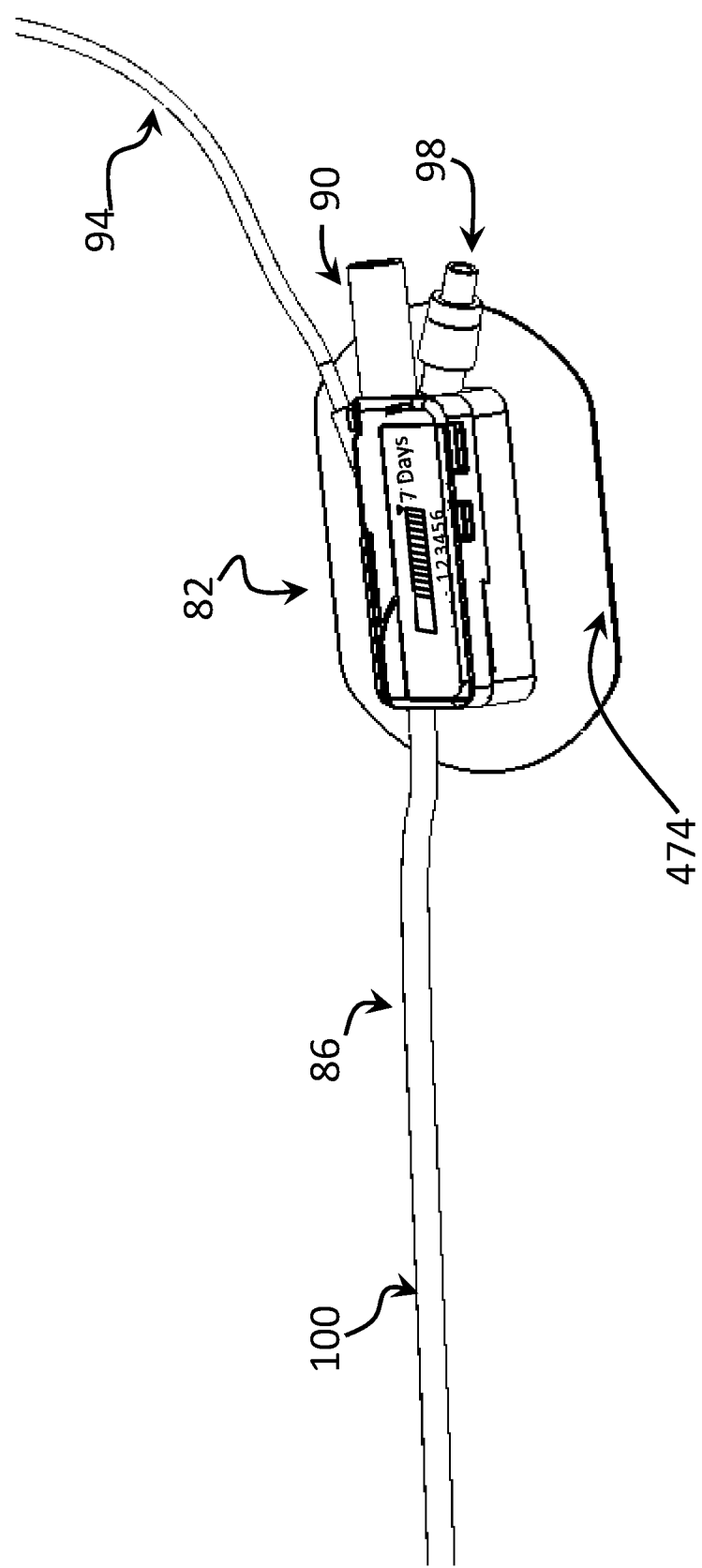
FIG. 5 is a top, side isometric view of the catheter securement device of FIG. 3 locked onto the urinary catheter, illustrated in the closed or locked position.

In an embodiment illustrated in FIGS. 1-2, the medical timing device 10 includes: (a) a body 14; (b) a retainer 18 moveably or pivotally coupled to the body 14; (c) a timer 22 supported by or coupled to the body 14; (d) a triggering element 26 supported by or coupled to the body 14; and (e) one or more locking members 30, 34 supported by or coupled to the body 14. In the example shown, the timer 22 is connected to the retainer 18. In other embodiments, however, the timer 22 can be connected to the body 14. Also, in the example shown, upper locking member 30 is connected to the retainer 18, and lower locking member 34 is connected to the body 14. In other embodiments, however, the medical timing device 10 can include a single locking member 30 or 34 connected to the retainer 18 or the body 14. For example, such single locking member could be incorporated into a one-way, locking hinge (not shown) operable to couple the retainer 18 to the body 14.

Depending upon the embodiment, the retainer 18 can be a door, panel, hook, U-shaped member or other capturing structure. The retainer 18 can be moveably coupled to the body 14 through any suitable fastener or coupler, including, but not limited to, a pivot member, pin, shaft, hinge, threaded engagement or tooth-based, interlocking structure. The timer 22 is operable to be adjusted, switched or otherwise changed from an inactive mode to an activate mode. In the inactive mode, the timer 22 is not functional to track or indicate the passage of time. In the active mode, the timer 22 is functional to track or otherwise indicate the passage of time. For example, when the timer 22 is changed to the active mode, the timer 22 starts a process of tracking the passage of time, such as the passage of seconds, minutes, hours, days, weeks, months, years or any suitable fractions or portions of such time periods. In addition, the timer 22 generates a visual indication or visual output representing such passage of time. For example, the timer 22 can display, point to, or otherwise indicate "Hour 1," "Hour 2," Hour 3," "Day 1," "Day 2," "Day 3" and the like. In an embodiment, the timer 22 generates an active indicator (e.g., a green light) indicating that the timer 22 is in the active mode. In an embodiment, the timer 22 also generates an expiration indicator (e.g., a red light, a pulsating or flashing red light or an audible alert) indicating an expiration of the applicable usage period of the medical article connected to the timer 22.

In an embodiment, the timer 22 tracks and indicates the passage of time based on a fluid or liquid diffusion process, as described below. In another embodiment, the timer 22 includes an electrical circuit or electronic component, together with a battery or solar-based power source. In such embodiment, the timer 22 electronically tracks and indicates the passage of time. For example, such timer 22 can generate a digital display of numerals, images or text corresponding to time passage.

In an embodiment, the triggering element 26 is a structural portion of the retainer 18. In another embodiment, the triggering element 26 is a structural portion of the body 14. In yet another embodiment, the triggering element 26 includes a structural portion of the retainer 18 and a structural portion of the body 14. It should be appreciated that in other embodiments, the triggering element 26 can include a ram, a plunger, a gear, an electrical conductor, an electrical switch or another suitable electronic, electromechanical or mechanical actuator operable to trigger both the locking of the medical timing device 10 and the changing of the timer 22 to its active mode.

The one or more locking members 30, 34, in an embodiment, cooperate to change the medical timing device 10 from an open or unlocked position 46 (FIG. 1) to a closed or locked position 50 (FIG. 2). In the locked position 50, the retainer 18 is irreversibly secured or locked to the body 14. In an embodiment, locking member 30 includes a plurality of semi-rigid, flexible teeth, and locking member 34 includes a tooth engager. For example, locking members 30, 34 can incorporate the structure of a self-locking tie. Once the locking members 30, 34 are moved together and engaged, the teeth and tooth engager prevent or inhibit the separation of the locking members 30, 34 without damaging or destroying the locking members 30, 34.

The body 14 defines at least part of an article-receiving recess 38 (e.g., a space or cavity) configured to at least partially receive an article portion 42 of a medical article. In the example shown, the article portion 42 is a tubular portion of a catheter. In operation, the user opens the retainer 18 and inserts the article portion 42 into the article-receiving recess 38. Next, the user applies a single action 54 (e.g., a hand closing force) to the retainer 18. Depending upon the embodiment, the single action 54 can be a downward, upward, sideward, rotary or other force. In the example shown, the single action 54 is a downward force. In response to the single action 54, the triggering element 26 causes the following outcomes or events to occur without requiring any further action from the user: (a) the medical timing device 10 changes form the unlocked position 46 (FIG. 1) to the locked position 50 (FIG. 2), wherein the retainer 18 becomes locked with the body 14, causing the medical timing device 10 to be locked onto the article portion 42; and (b) the timer 22 changes from its inactive mode to its active mode.

Depending upon the embodiment, such outcomes (e.g., locking and timer activation) can occur simultaneously in response to the single action 54, or such outcomes can occur sequentially in response to the single action 54. For example, the locking can occur a fraction of a second before the timer activation, or the timer activation can occur a fraction of a second before the locking.

In an embodiment illustrated in FIGS. 1-2, the medical timing device 10 is incorporated into or otherwise attached to a medical device 58 which, in this example, is a catheter securement device 62. The catheter securement device 62 includes: (a) the medical timing device 10; and (b) a body support or base 66 coupled to the bottom body surface 70. The base 66, in an embodiment, is pivotally coupled to the body 14. The base 66 also has a tissue interface 74 configured to be attached to the skin tissue 78 of the patient. In an embodiment, the bottom body surface 70 is detachably secured to the base 66 through use of a suitable non-permanent adhesive. Likewise, the tissue interface 74 includes a peel-away layer that, when removed, exposes an adhesive layer on the tissue interface 74.

Figure 10:
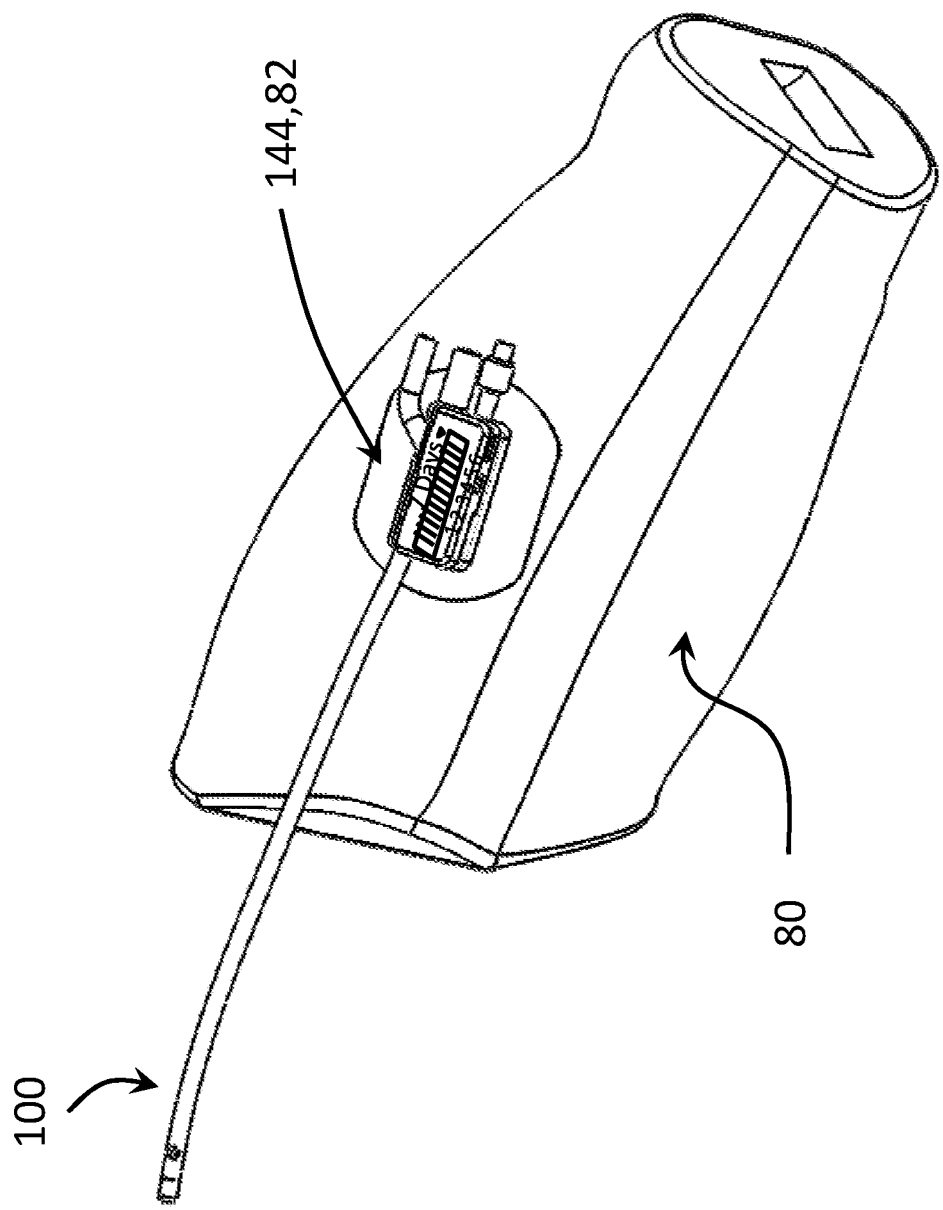
FIG. 10 is an isometric view of the catheter securement device of FIG. 3 locked onto a urinary catheter, illustrating the attachment of the catheter securement device (in its locked position) to the thigh of a leg of a patient.

In use, an assembler adheres the body 14 to the base 66. Next, the user (e.g., clinician) adheres the base 66 to the skin tissue 78, such as the skin of the patient's thigh 80 (FIG. 10). Next, the user inserts the article portion 42 into the medical timing device 10 and applies a single action 54, causing the timer 22 to activate and the medical timing device 10 to lock onto the article portion 42. If the patient moves his/he legs slightly during treatment, the body 14 pivots relative to the base 66 to relieve stress and forces that would otherwise urge the catheter securement device 62 to separate from the skin tissue 78.

Figure 6:
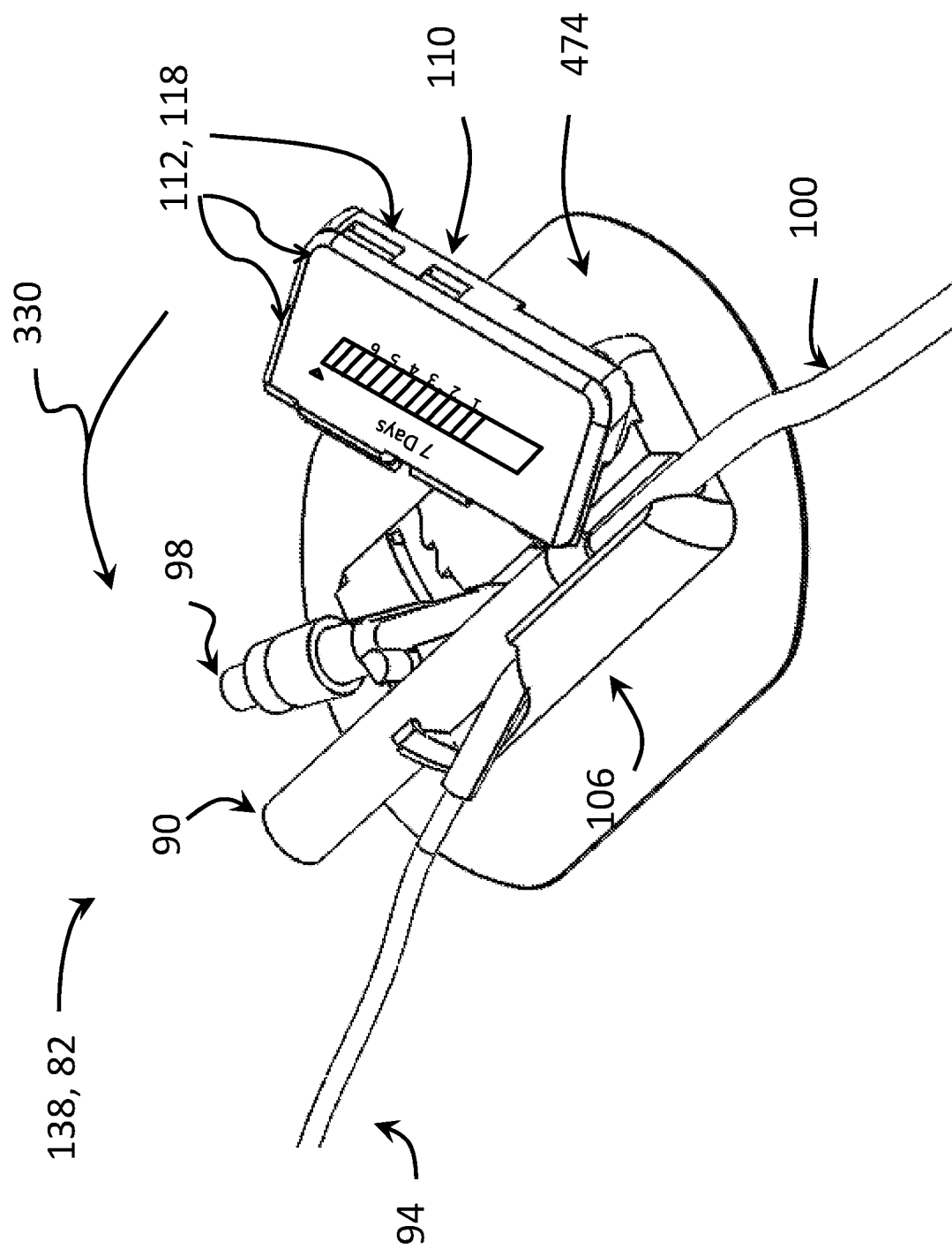
FIG. 6 is a top, front isometric view of the catheter securement device of FIG. 3 holding the urinary catheter, illustrated in the open or unlocked position.
Figure 7:
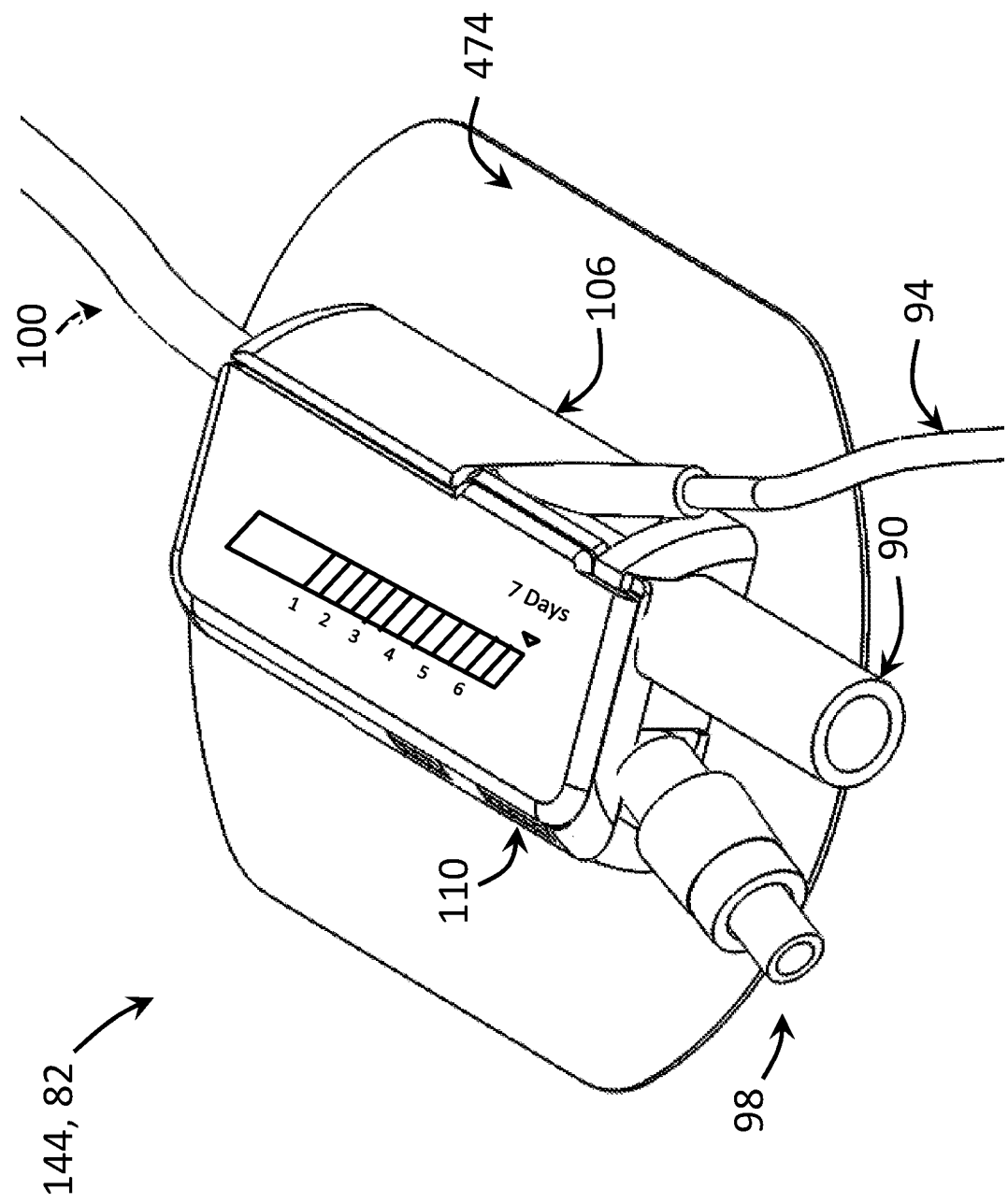
FIG. 7 is an enlarged, top, rear isometric view of the catheter securement device of FIG. 3 locked onto the urinary catheter, illustrated in the closed or locked position.
Figure 8:
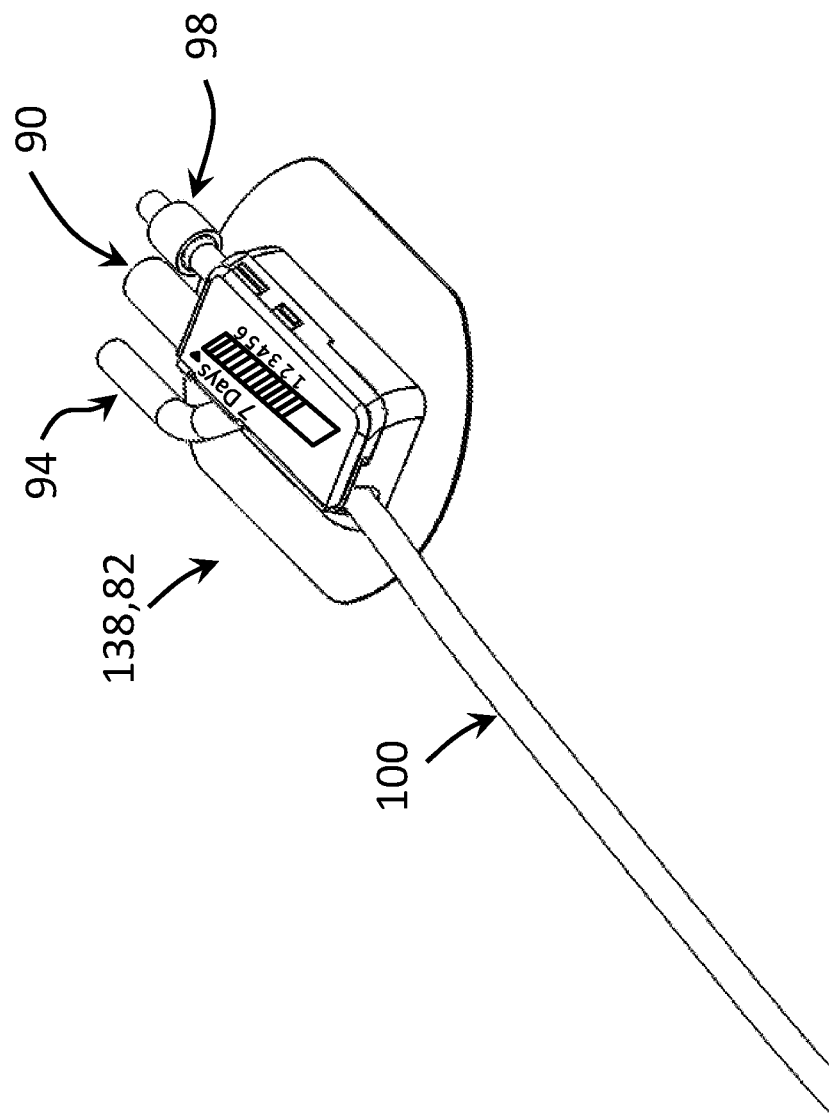
FIG. 8 is a top, rear isometric view of the catheter securement device of FIG. 3 locked onto a urinary catheter having differently-shaped branches, illustrated in the closed or locked position.
Figure 11:
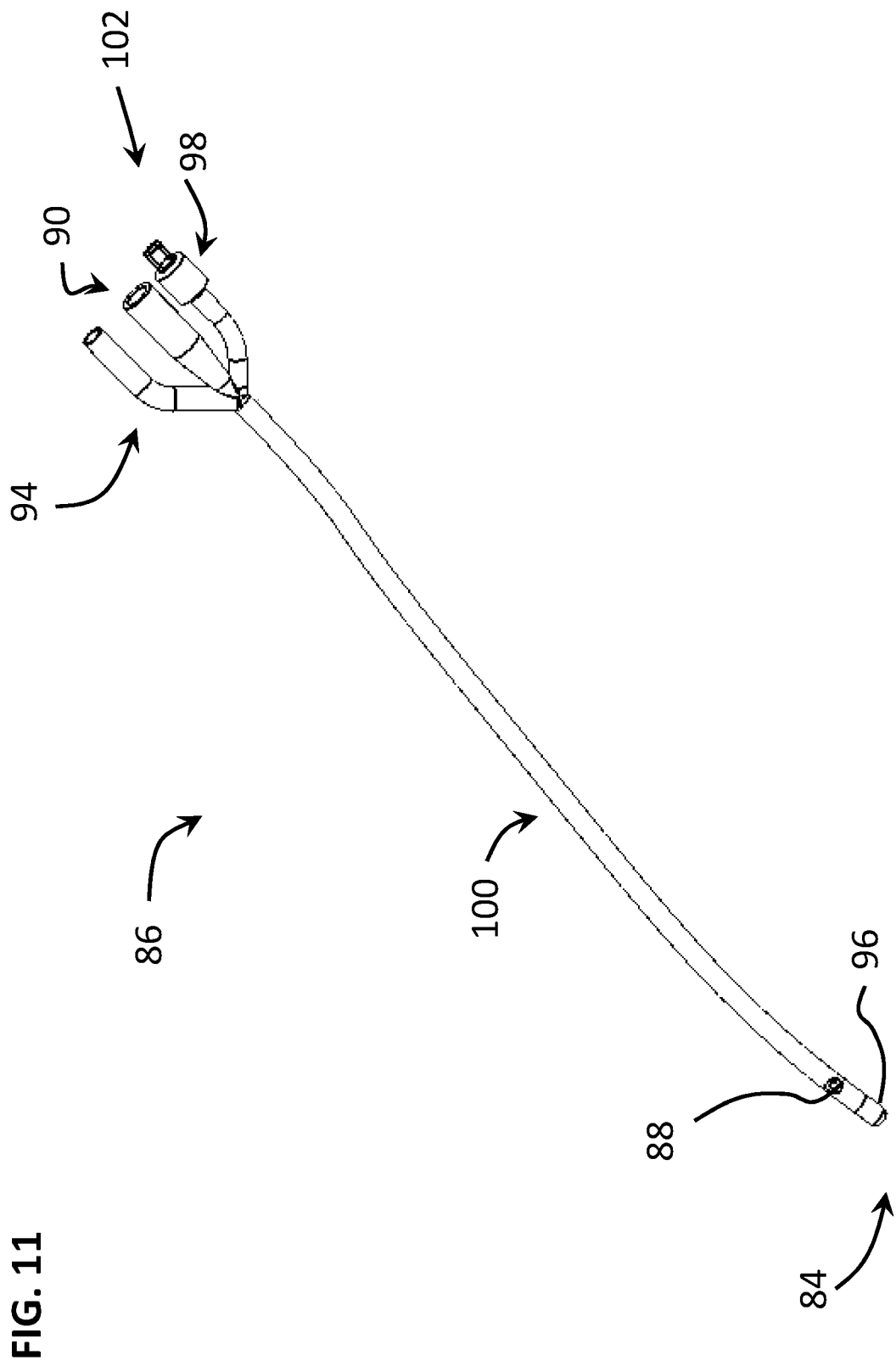
FIG. 11 is an isometric view of the urinary catheter of FIG. 8.

In an embodiment illustrated in FIGS. 3-31, the catheter securement device 82 is configured to be locked onto a three-way Foley urinary catheter 86. The urinary catheter 86 is configured to be inserted through the patient's urethra until the distal end 84 (FIG. 11) reaches the patient's bladder. Referring to FIGS. 6 and 11, in the example shown, the urinary catheter 86 includes: (a) a urine drainage channel or lumen (not shown) extending from the proximal urinary drainage branch 90 to the distal end 84 of the urinary catheter 86, wherein the urine drainage lumen is fluidly connected to distal opening 88 for fluidly communicating with the urine contents of the patient's bladder; (b) an inflation channel or lumen (not shown) extending form the proximal inflation branch 94 to the distal end 84 of the urinary catheter 86, wherein the inflation lumen is fluidly connected to a balloon or inflatable portion 96 of the urinary catheter 86; (c) an irrigation channel or lumen (not shown) extending from the proximal irrigation branch 98 to the to the distal end 84 of the urinary catheter 86, wherein the irrigation lumen is configured to be fluidly connected to a source of pressurized fluid or liquid for purposes of irrigating the urinary catheter 86 or delivering solutions through distal opening 88 to the patient's bladder; and (d) a main tube 100 extending from the branches 90, 94, 98 to the distal end 84 of the urinary catheter 86.

As shown in FIG. 11, the proximal end 102 of urinary catheter 86 has a Y-shape or W-shape. It should be appreciated, however, that other types and shapes of urinary catheters can be used with the catheter securement device 62. For example, the catheter securement device 62 can be used to secure and time-track two-way urinary catheters having only two proximal branches instead of three.

Figure 15:
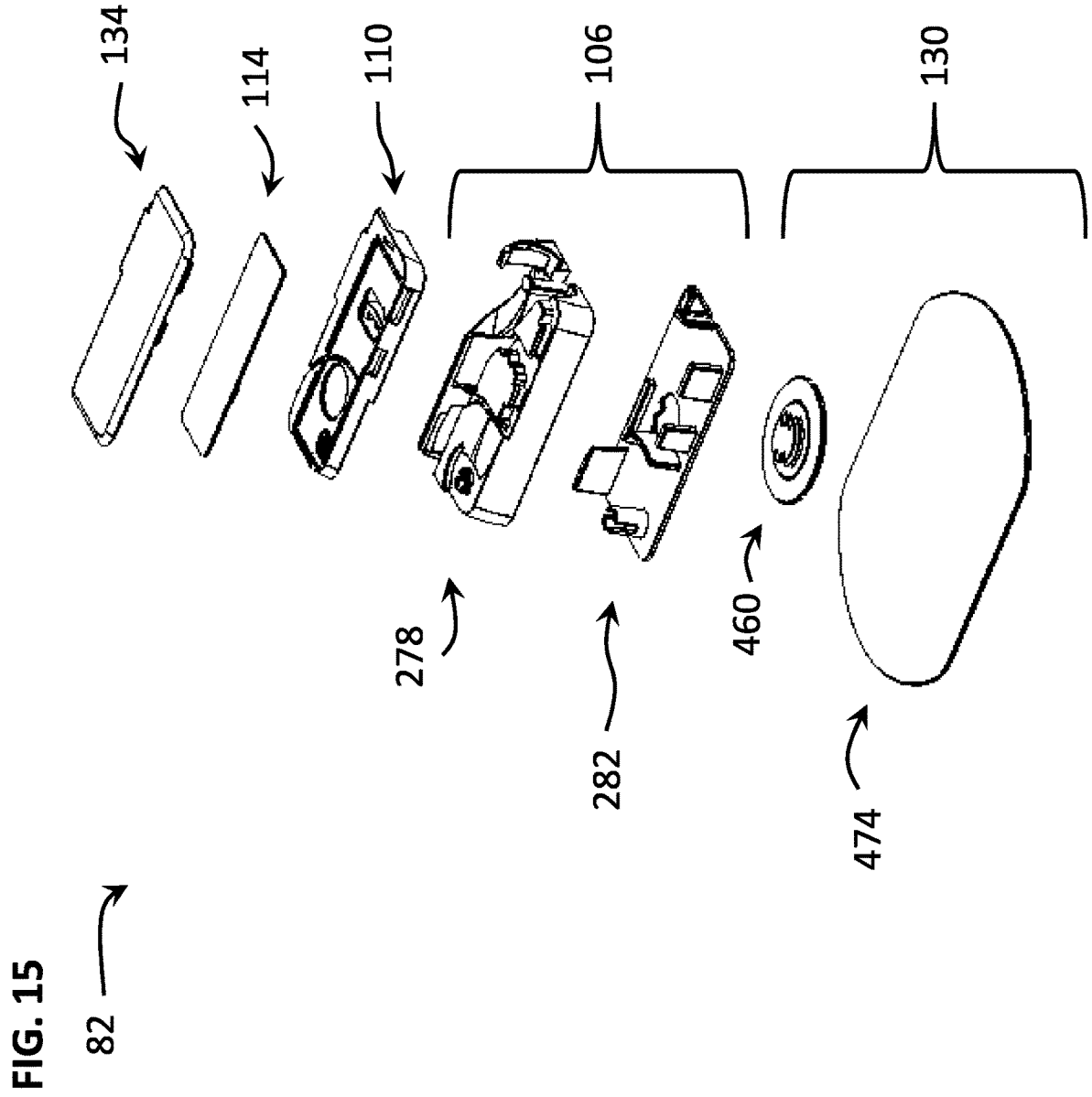
FIG. 15 is an exploded, top isometric view of the catheter securement device of FIG. 3.
Figure 16:
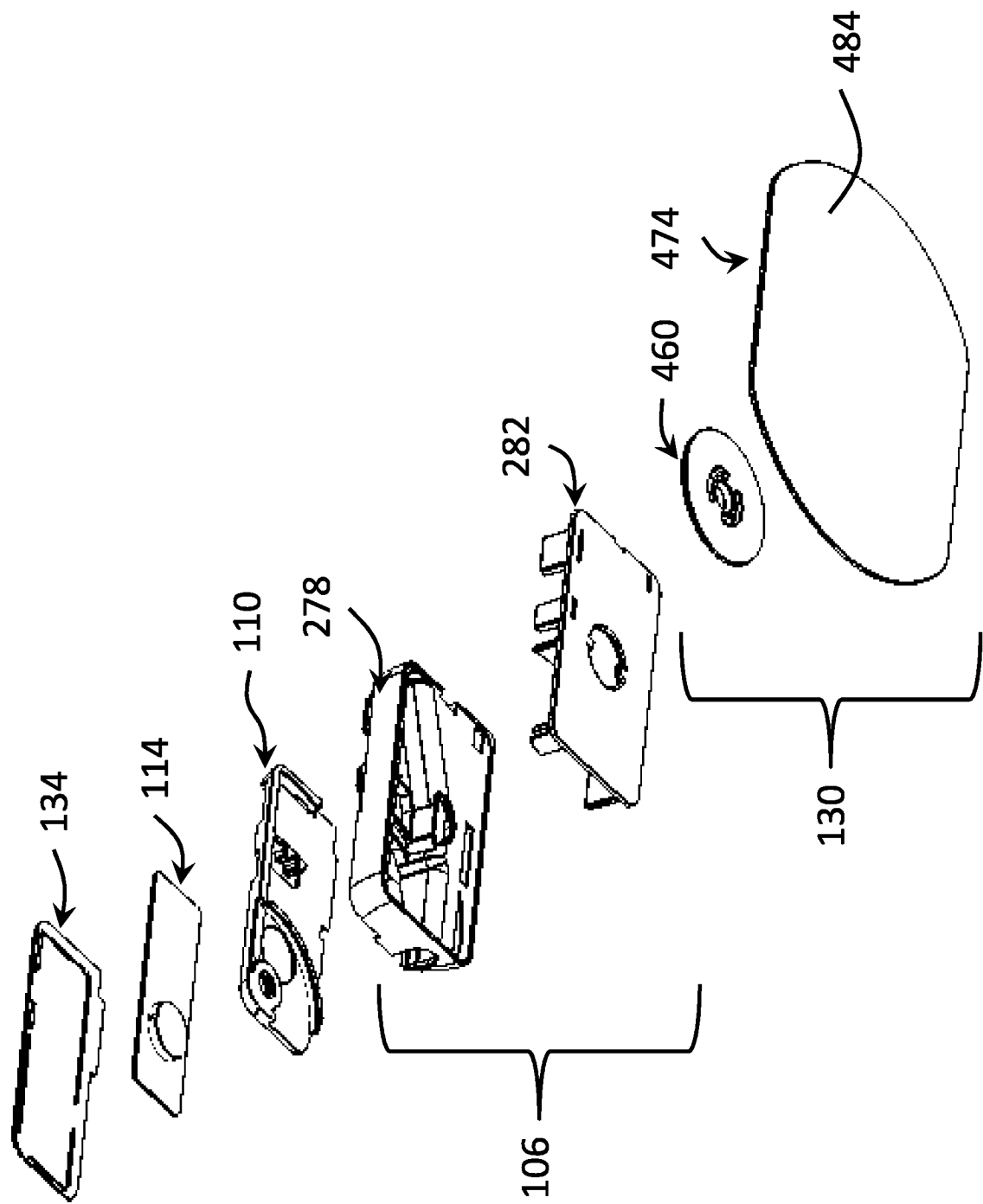
FIG. 16 is an exploded, bottom isometric view of the catheter securement device of FIG. 3.

Referring to FIG. 15, in an embodiment, the catheter securement device 82 includes: (a) a body 106; (b) a retainer 110 pivotally coupled to the body 106; (c) a timer 114 supported by or coupled to the body 106; (d) a triggering element 118 (FIG. 6) incorporated into retainer 110; (e) retainer locking member 122 (FIG. 17) incorporated into retainer 110; (f) body locking member 126 (FIG. 13) incorporated into body 106; (g) a body support or base 130 coupled to body 106; and (h) a security cover 134 attachable to the retainer 110 so as to sandwich the timer 114 between the security cover 134 and the retainer 110. As described below, the base 130 is configured to anchor the urinary catheter 86 to the patient's skin tissue.

In this embodiment, the triggering element 118 of retainer 110 includes the exterior retainer surface 112 (FIG. 6) of the retainer 110. As described below, by pushing or applying a single action 54 force to the exterior retainer surface 112, the user can change the catheter securement device 82 from an unlocked position 138 (FIGS. 6 and 13-14) to a locked position 144 (FIGS. 3-5, 7-10 and 12).

Figure 29:
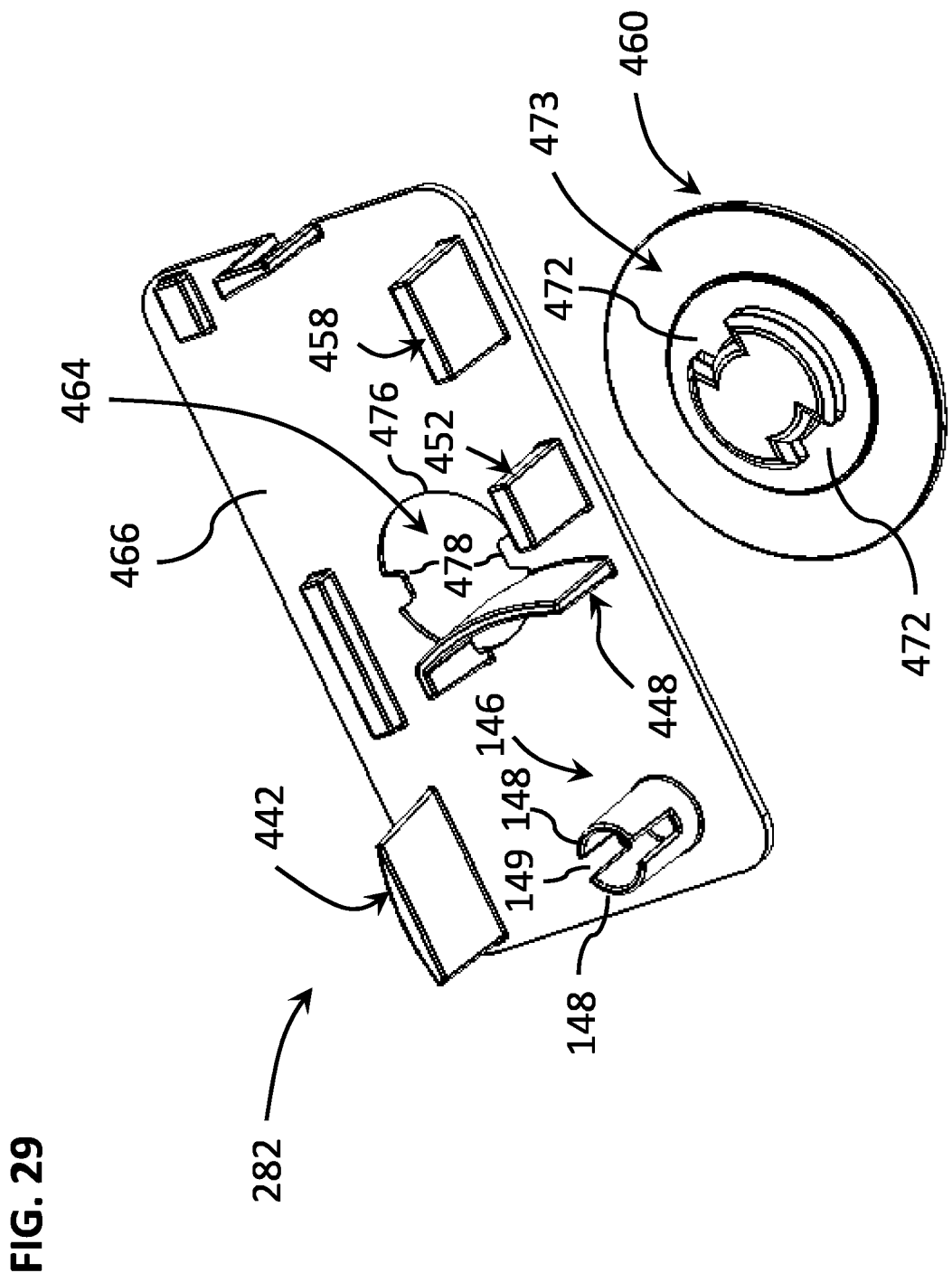
FIG. 29 is yet another exploded isometric view of embodiments of the lower body portion and rotary mount or pivot mount of the catheter securement device of FIG. 3.
Figure 30:
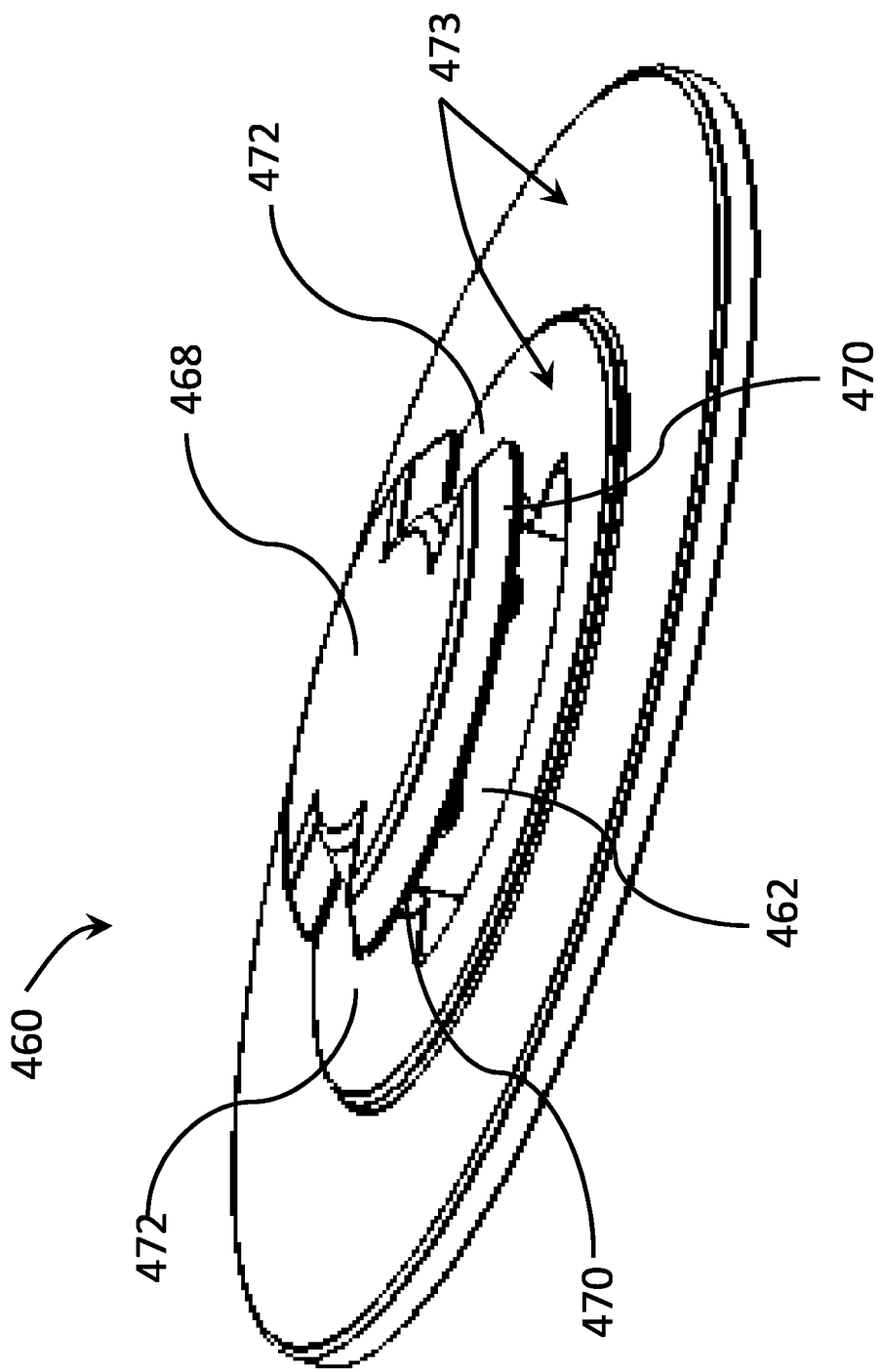
FIG. 30 is a top isometric view of an embodiment of the rotary mount or pivot mount of the catheter securement device of FIG. 3.
Figure 31:
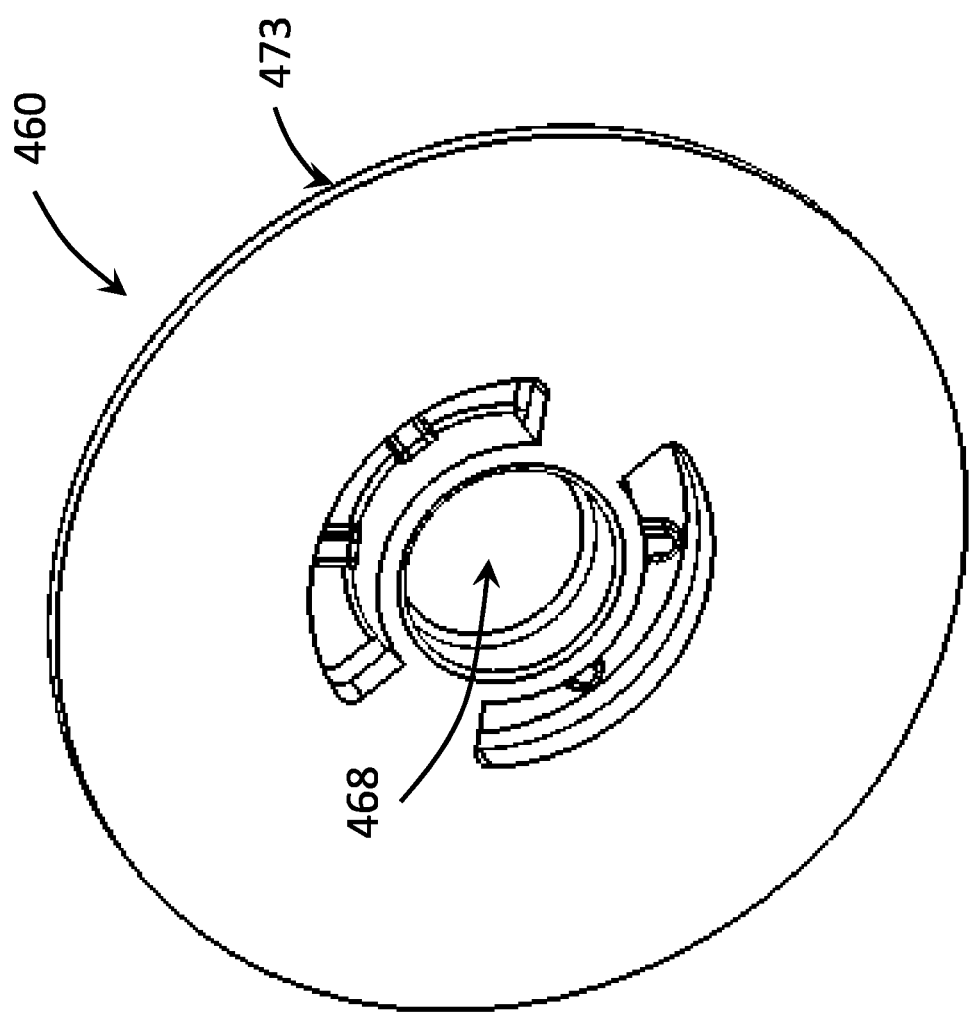
FIG. 31 is a bottom isometric view of an embodiment of the rotary mount or pivot mount of the catheter securement device of FIG. 3.
Figure 32:
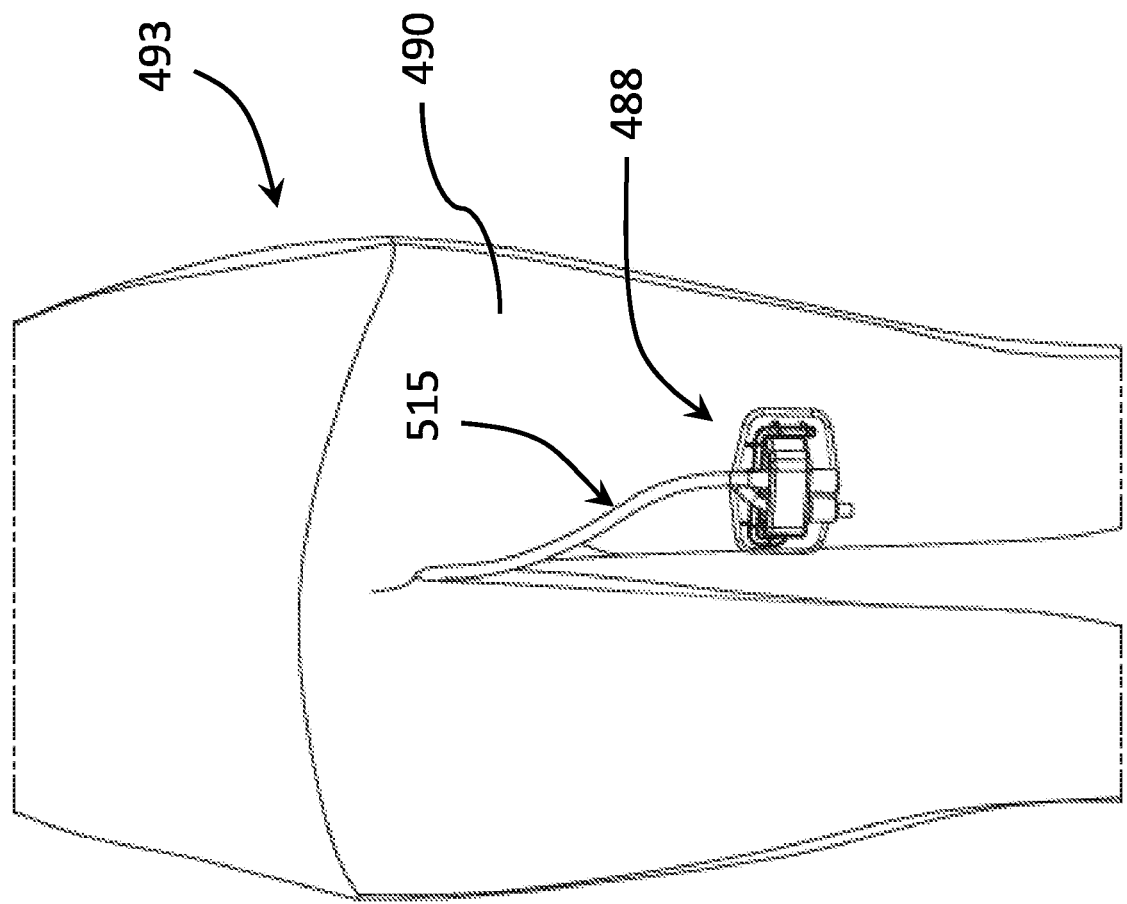
FIG. 32 is an isometric view of another embodiment of a catheter securement device locked onto a urinary catheter, illustrating the catheter securement device attached to the thigh of a patient.

The retainer 110 defines a pivot opening 142 (FIG. 17) configured to receive a pivot member 146 (FIG. 17) of body 106. The pivot member 146 couples to the retainer 110 in a press-fit or snap-fit configuration, wherein the pivot member 146 radially compresses, then snaps into the pivot opening 142, and then radially expands. In the expanded form, the perimeter of the collar 150 (FIG. 24) is greater than the perimeter of the pivot opening 142, thereby pivotally securing the retainer 110 to the body 106. As shown in FIG. 29, the pivot member 146 has a split configuration including a plurality of fingers 148 separated by a slit or gap 149. Upon insertion into the pivot opening 142, the fingers 148 flex toward each other, and after full insertion, the fingers 148 are predisposed to flex away from each other.

Figure 22:
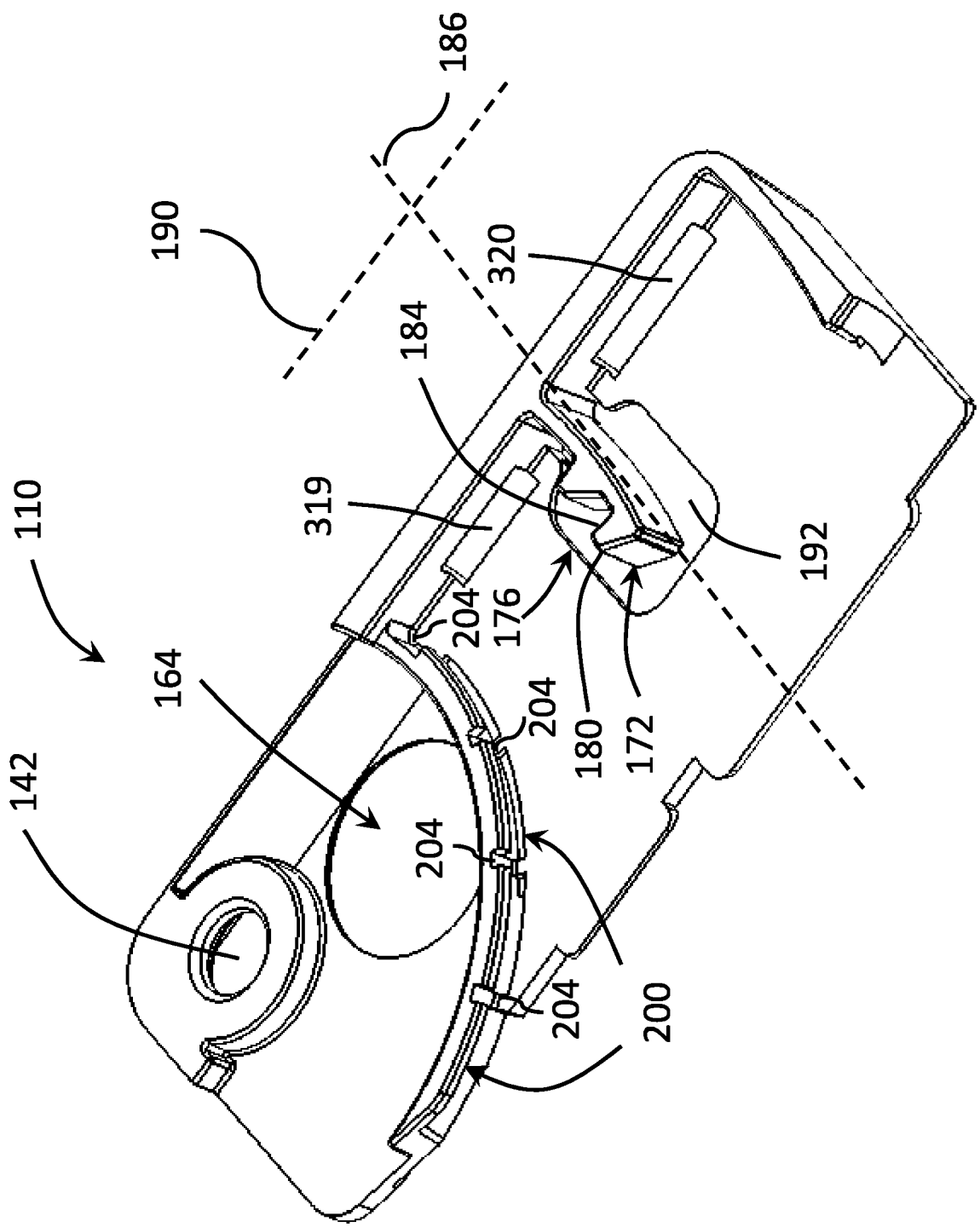
FIG. 22 is a bottom isometric view of an embodiment of the retainer of the catheter securement device of FIG. 3.
Figure 23:
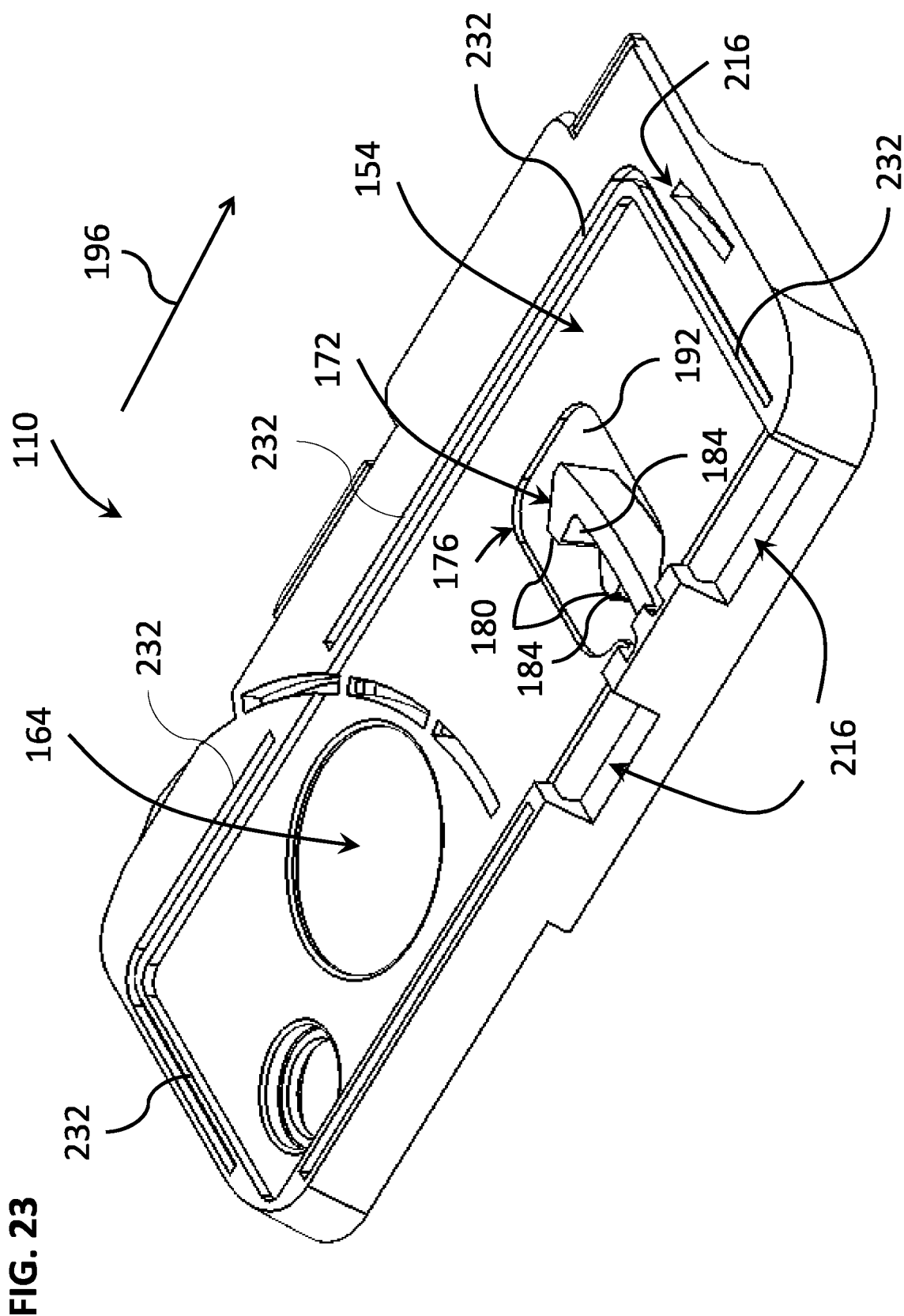
FIG. 23 is a top isometric view of an embodiment of the retainer of the catheter securement device of FIG. 3.
Figure 24:
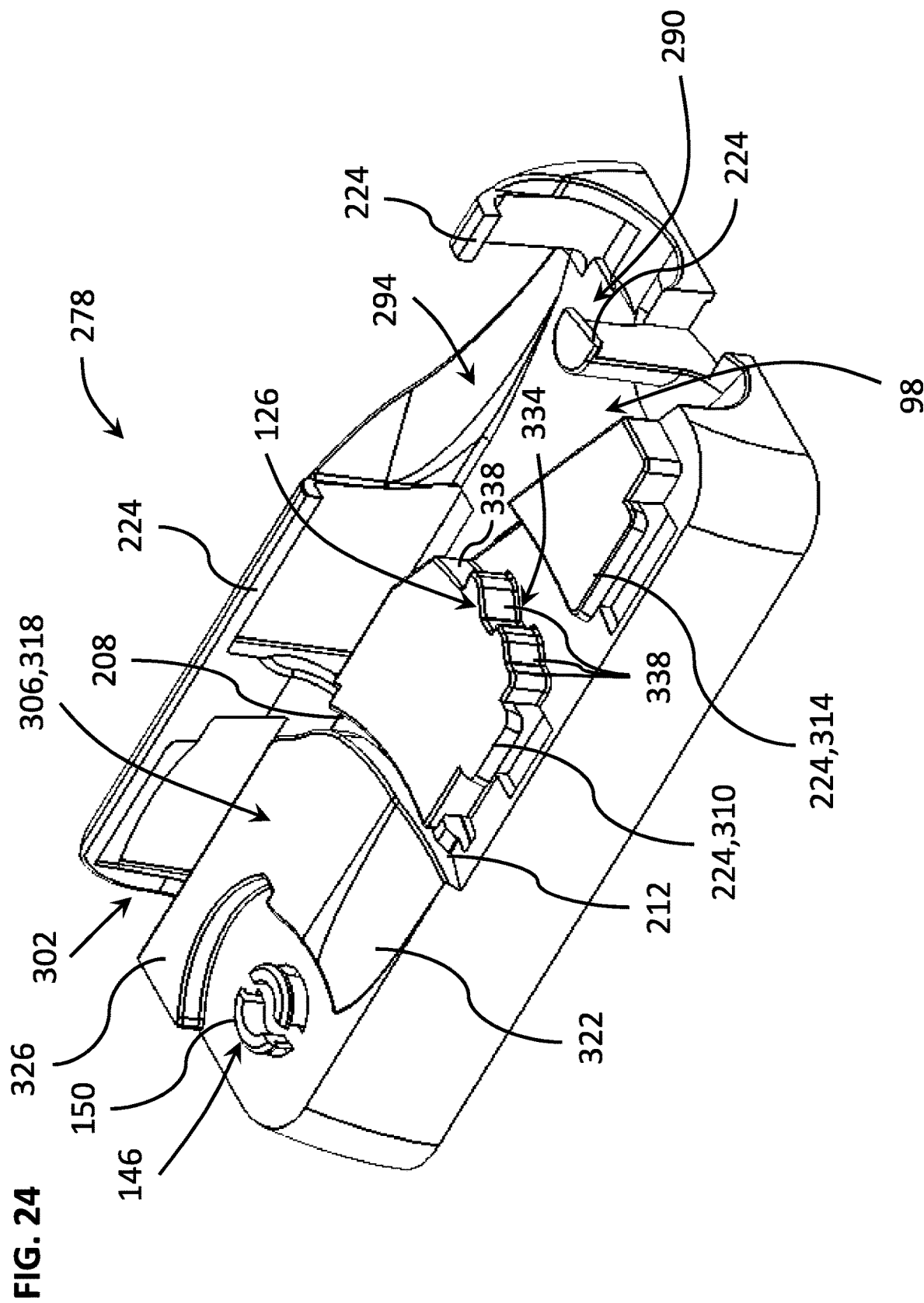
FIG. 24 is a top isometric view of an embodiment of the upper body portion of the catheter securement device of FIG. 3.
Figure 25:
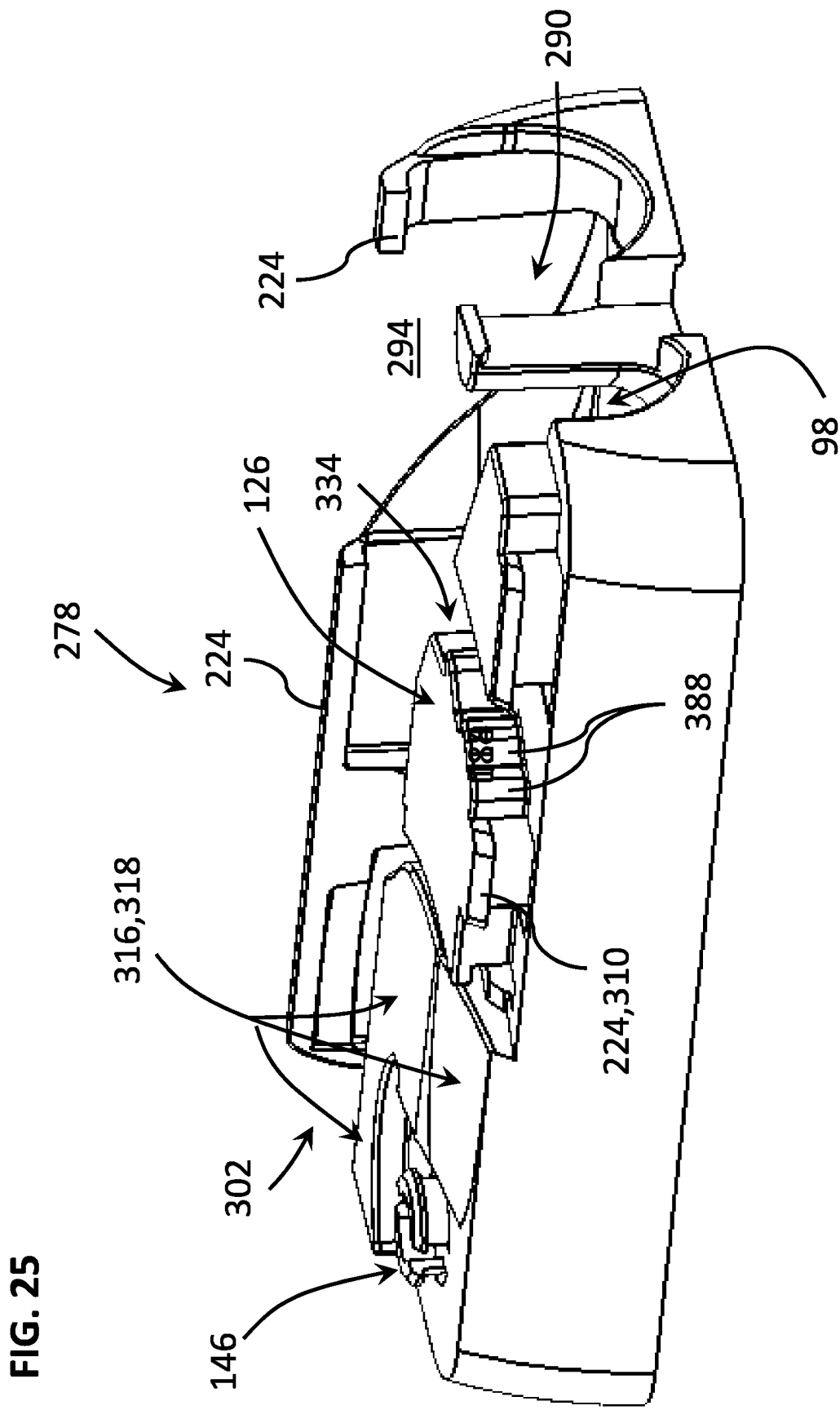
FIG. 25 is a side isometric view of an embodiment of the upper body portion of the catheter securement device of FIG. 3.
Figure 26:
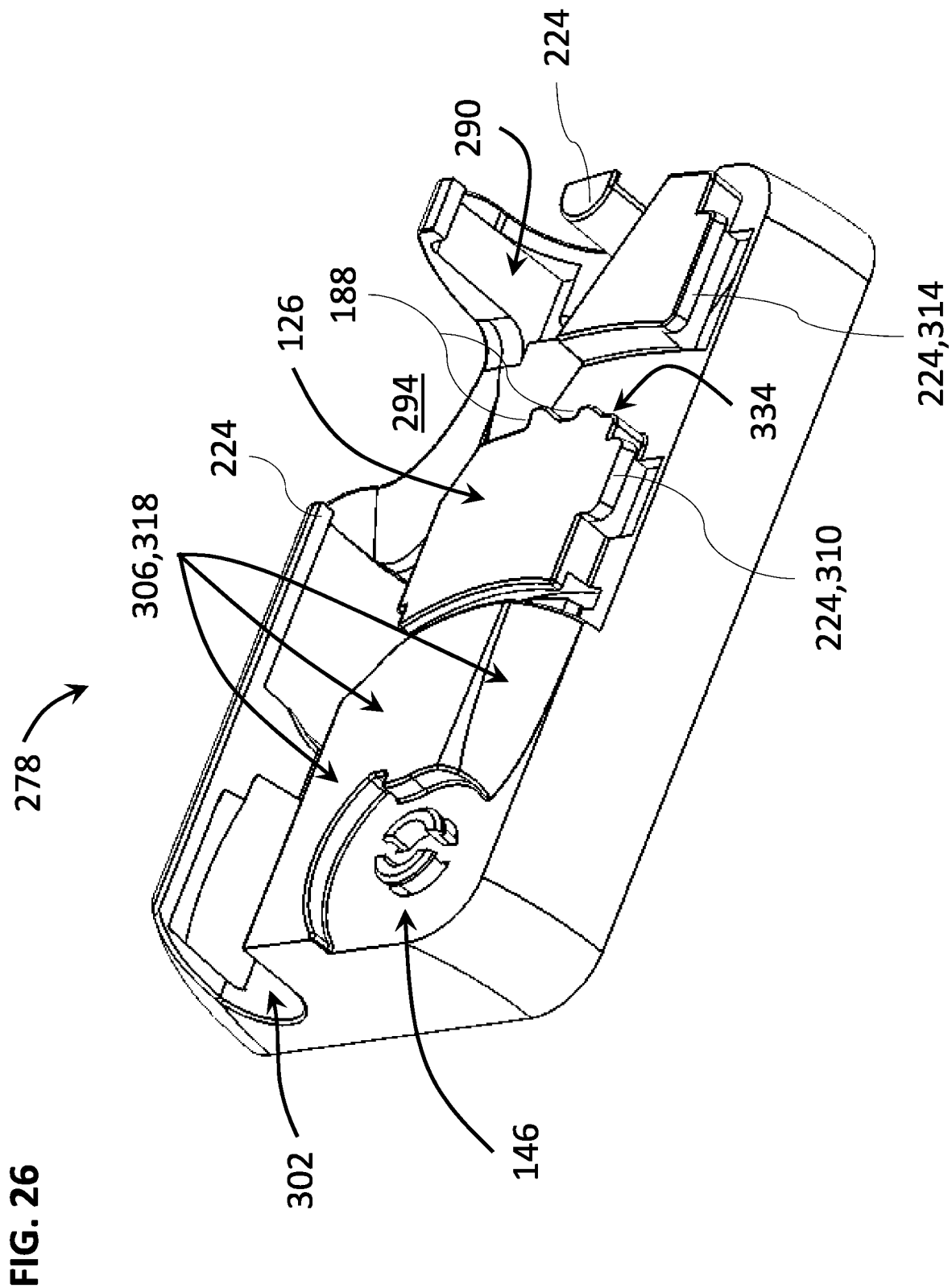
FIG. 26 is another top isometric view of an embodiment of the upper body portion of the catheter securement device of FIG. 3.

Furthermore, the retainer 110 defines: (a) a main recess 154 (FIG. 23) configured to receive the timer perimeter 160 (FIG. 21) of the timer 114; and (b) a pass-through opening or passage 164 (FIG. 23) configured to receive the flexible fluid container 168 (FIG. 21) of the timer 114. As illustrated in FIGS. 22-23, the retainer locking member 122 includes a flexible arm 172 having a plurality of retainer teeth 176. Each tooth 176 has a retainer slide surface 180 and a retainer lock surface 184. As described below, as the catheter securement device 82 is locked, the arm 172 flexes or bends while the retainer slide surfaces 180 slide against the body locking member 126 (FIGS. 24-26). Eventually, the retainer lock surfaces 184 become seated on the body lock surfaces 188 (FIG. 26).

As shown in FIG. 22, the retainer lock surface 184 can be angled at least partially downward because the flexible arm 172 is predisposed to extend along a slanted axis 186 (FIG. 22) that intersects with horizontal axis 190 in a non-perpendicular fashion. During locking, the flexible arm 172 moves so as to extend along a different axis (not shown) that also intersects with the horizontal axis 190.

In an embodiment, the retainer 110 also defines a lock access passage 192, as illustrated in FIGS. 22-23. Lock access passage 192 enables a technician to access the arm 172 to flex it in the unlock direction 196 (FIG. 23) to unlock the retainer 110 from the body 106. This enables the technician to remove the catheter securement device 82 from the catheter 86 for refurbishment, repair or other purposes. In another embodiment, the retainer 110 has a solid surface (not shown) that covers the lock access passage 192 for supplemental security.

The retainer 110 includes a lock guide 200, as illustrated in FIG. 22, that controls and guides the pivoting motion of the retainer 110 relative to the body 106. In the embodiment shown, the lock guide 200 has an arc-shape defining a plurality of equally spaced-apart guide slots 204. As the retainer 110 is pivoted for locking, the lock guide 200 slides against the opposing body guide walls 208, 212 (FIG. 24). In an embodiment, one or both of the body guide walls 208, 212 defines one or more ridges or teeth configured to at least partially fit into the guide slots 204 of the retainer 110. Such arrangement can provide additional locking security when the catheter securement device 82 is locked.

Figure 17:
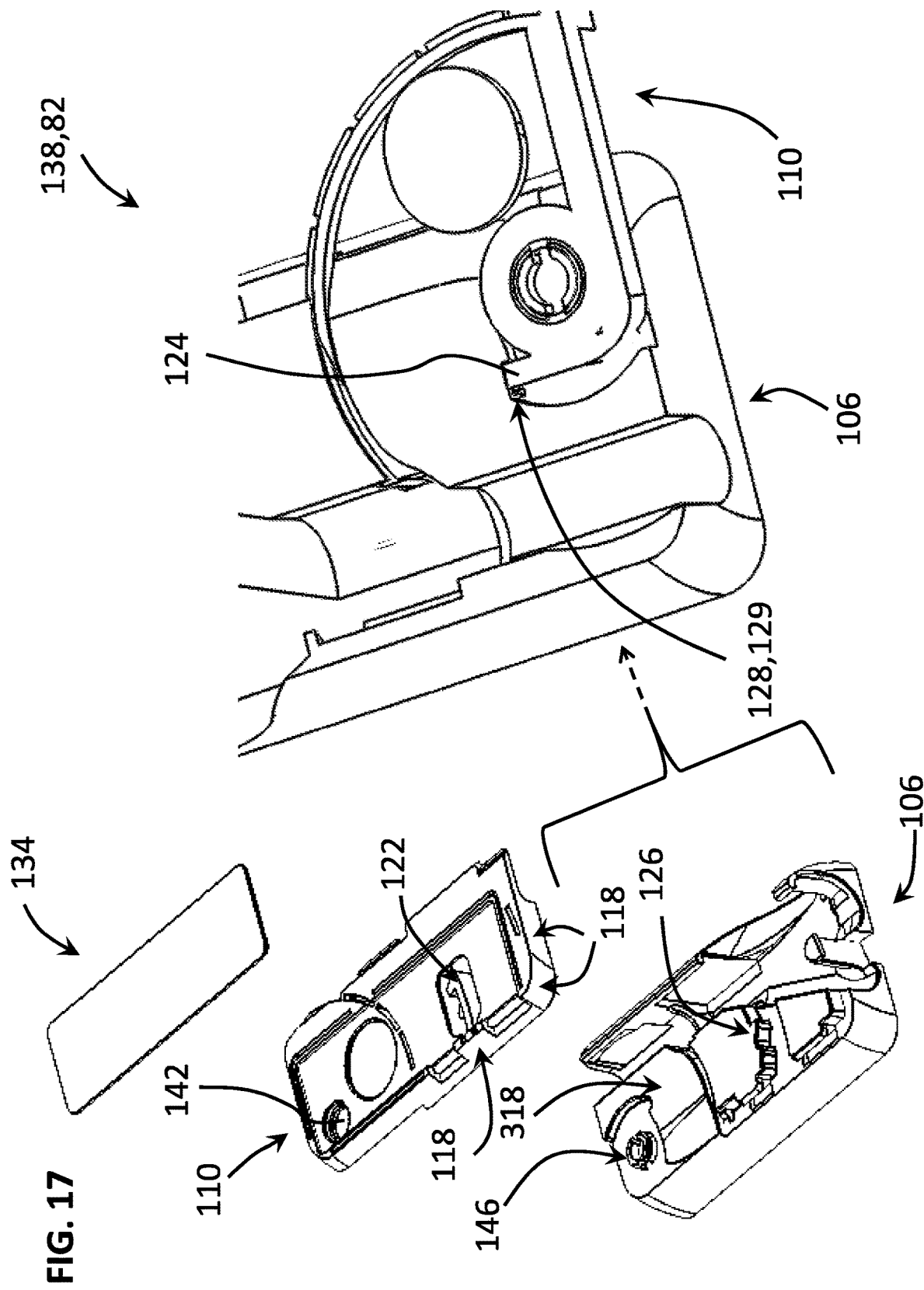
FIG. 17 is an exploded isometric view of the catheter securement device of FIG. 3, illustrating an enlarged view of portions of embodiments of the body and retainer.
Figure 18:
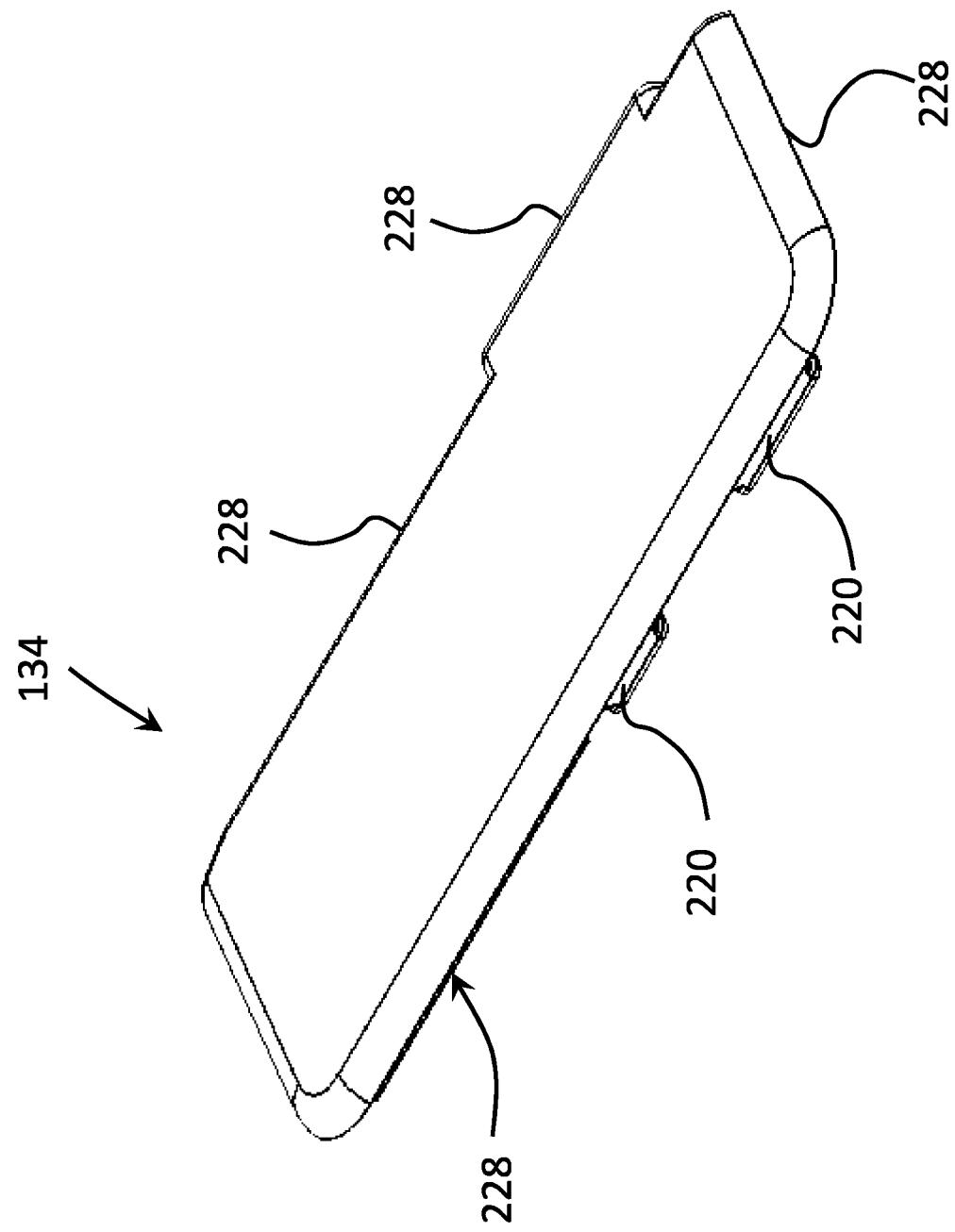
FIG. 18 is a top isometric view of an embodiment of the security cover of the catheter securement device of FIG. 3.
Figure 19:
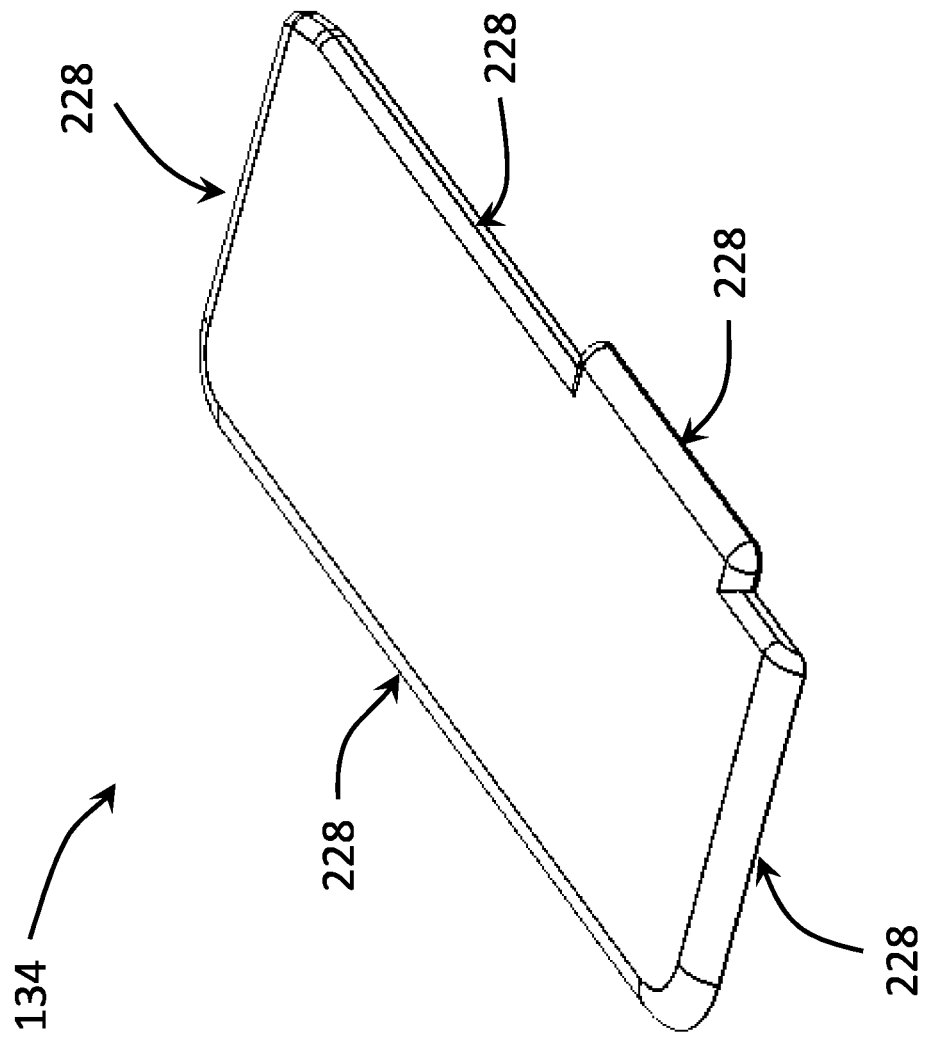
FIG. 19 is another top isometric view of an embodiment of the security cover of the catheter securement device of FIG. 3.
Figure 20:
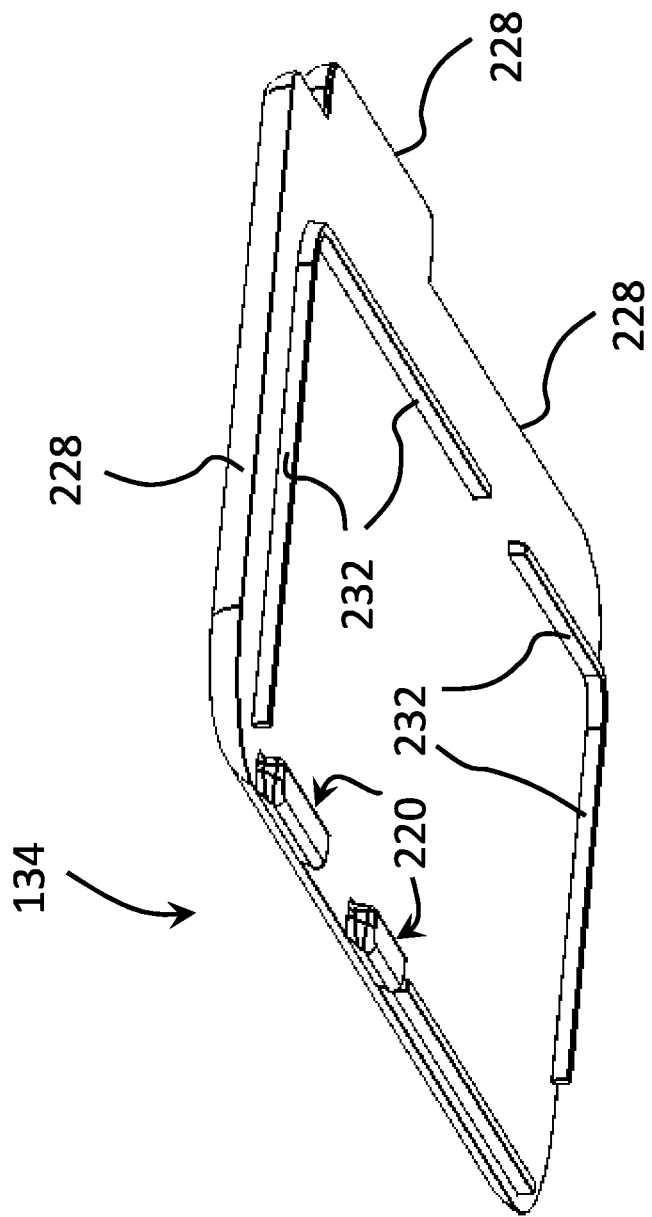
FIG. 20 is a bottom isometric view of an embodiment of the security cover of the catheter securement device of FIG. 3.

In an embodiment illustrated in FIG. 17, the retainer 110 includes a retainer mode controller 124, and the body 106 includes a body mode controller 128. In this embodiment, when assembling the catheter securement device 62, the assembler positions the retainer 110 in the open or unlocked position 138, as illustrated in FIG. 17. The retainer mode controller 124 cooperates with the body mode controller 128 to control the inactive and active modes of the catheter securement device 62. In the example shown, the retainer mode controller 124 includes a member or retainer portion that interferes with the body mode controller 128 which, in this example, is a finger, projection or detent 129 extending upward from the body 106. This physical interference helps to maintain the catheter securement device 62 in the inactive mode and open position 138 while it is packaged, transported and inventoried for future use. This reduces the likelihood of an inadvertent or unintentional early activation of the catheter securement device 62.

When a user is ready to deploy the catheter securement device 62, the user applies the single action 54 (e.g., a hand force) so as to overcome the counteractive force of the body mode controller 128. For example, the detent 129 eventually fails, cracks or otherwise breaks to enable the retainer mode controller 124 to continue moving, which enables the user to fully lock the catheter securement device 62 in the closed or locked position 144.

As illustrated in FIG. 23, the retainer 110: (a) defines a plurality of security openings or security slots 216; (b) includes security lips 224 (FIG. 9) configured to receive and hold (or hook onto) the cover edges 228 (FIG. 18) of security cover 134; and (c) defines L-shaped insertion guide slots 232 (FIG. 23) configured to receive the cover inserts 236 (FIG. 20) of the security cover 134. The security slots 216 are configured to receive or mate with the security projections or security tabs 220 (FIG. 20) of the security cover 134. In an alternative embodiment (not shown) the security slots 216 are configured to lock with the security projections or security tabs 220 of the security cover 134. In an embodiment, the security cover 134 is a rigid or semi-rigid panel that is partially or fully transparent, translucent or otherwise see-through to enable the user to see the visual output of the timer 114, as described below.

Figure 21:
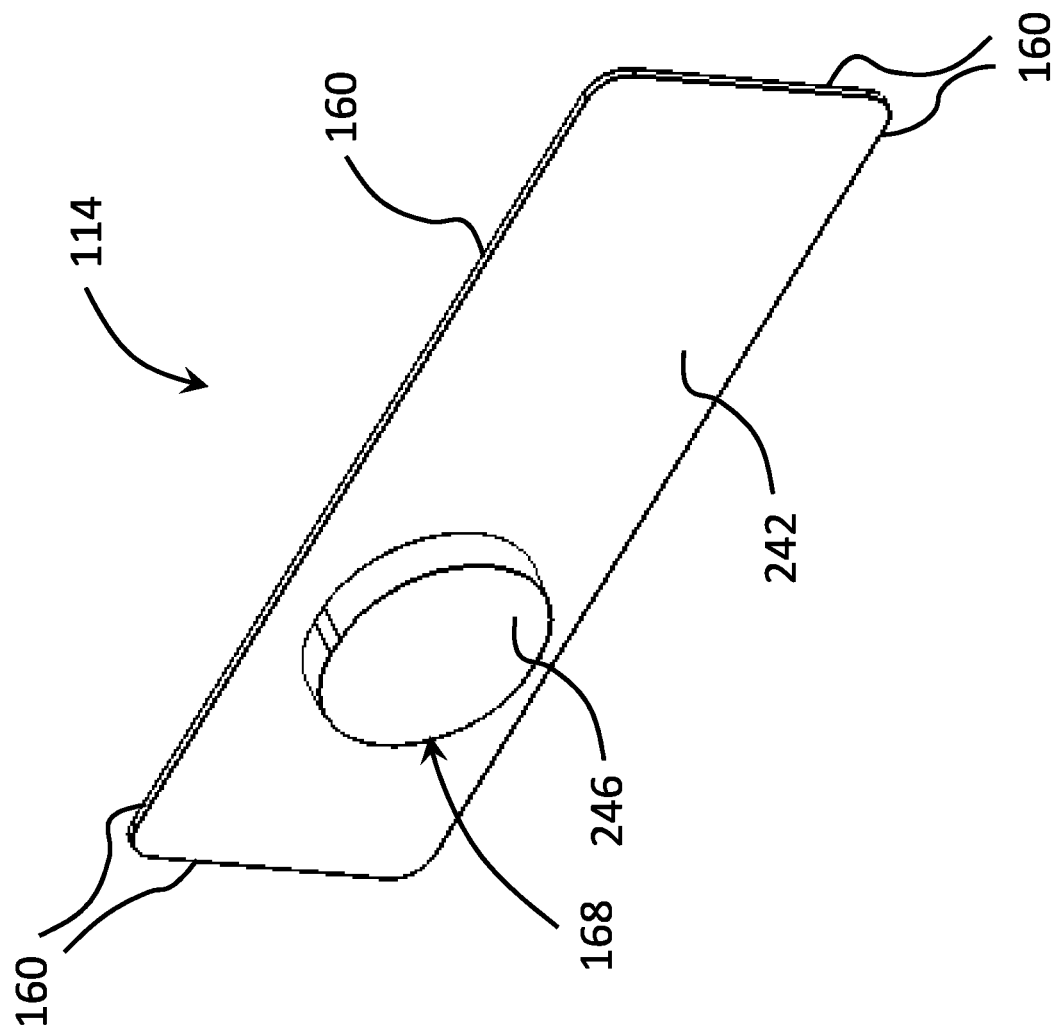
FIG. 21 is a bottom isometric view of an embodiment of the timer of the catheter securement device of FIG. 3.

In an embodiment illustrated in FIG. 21, the timer 114 includes a timer body 240 and the flexible fluid container 168 connected to the bottom side 242 of the timer body 240. In an embodiment, the timer body 240 is flexible or semi-rigid and includes a stack of substrates or layers of a suitable wicking material or porous material. Each such layer has a liquid absorption characteristic. The fluid container 168 is flexible or deformable such as a pouch or bag, and the fluid container 168 includes a container bottom 246. The fluid container 168 is configured to hold, retain or contain a colored liquid, such as ink, paint or another suitable liquid having a dye, such as a red or blue dye. The timer 141 includes a membrane or seal (not shown) located opposite of the container bottom 246. When a force is applied to the liquid-filled fluid container 168, this causes deformation of the fluid container 168 and increased pressure within fluid container 168. When the pressure reaches a threshold level, the seal ruptures, enabling the liquid to travel toward the stack of layers. The layers gradually absorb the liquid through diffusion. The rate of diffusion, which can depend upon the viscosity of the liquid and other factors, is associated with a clock function or time-tracking function. This non-electronic time-tracking function has the advantage of dependability independent of electrical power. Therefore, this reduces the risk of time-tracking failures caused by bad batteries, power outages or failed electronic components.

Figure 9:
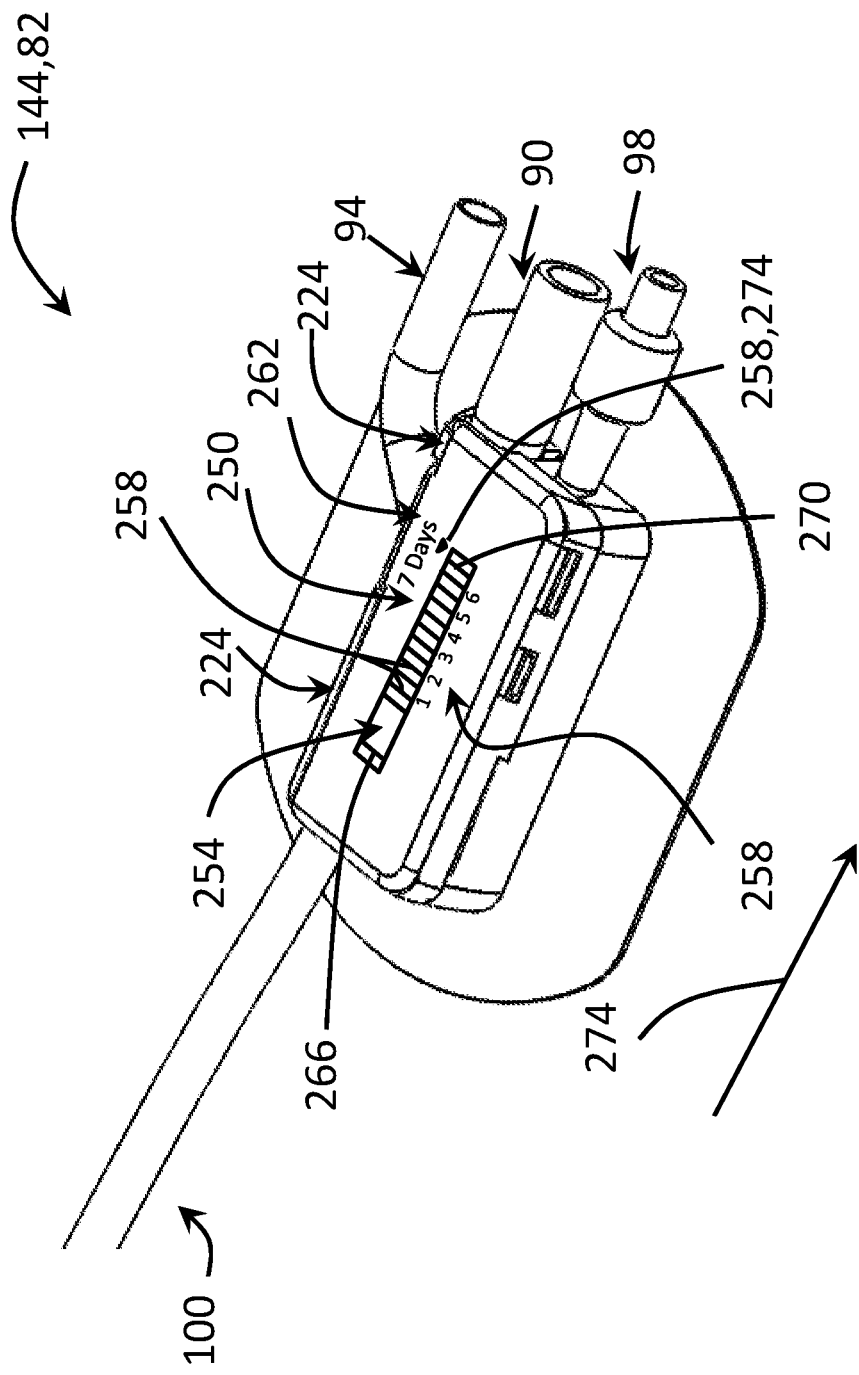
FIG. 9 is an enlarged, top, side isometric view of the catheter securement device of FIG. 3 locked onto the urinary catheter of FIG. 8, illustrated in the closed or locked position.
Figure 12:
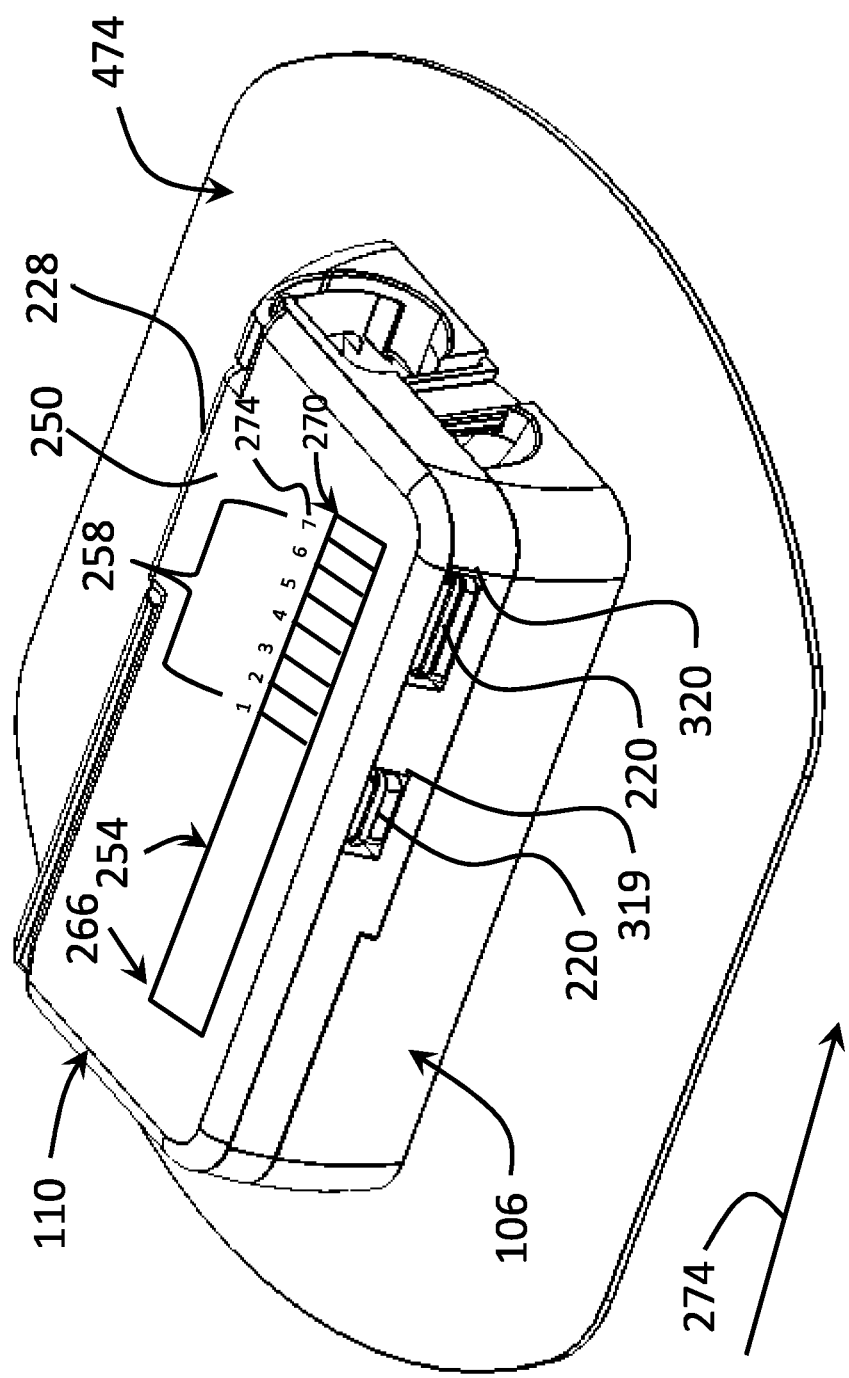
FIG. 12 is an enlarged isometric view of the catheter securement device of FIG. 3, illustrated in the closed or locked position.
Figure 13:
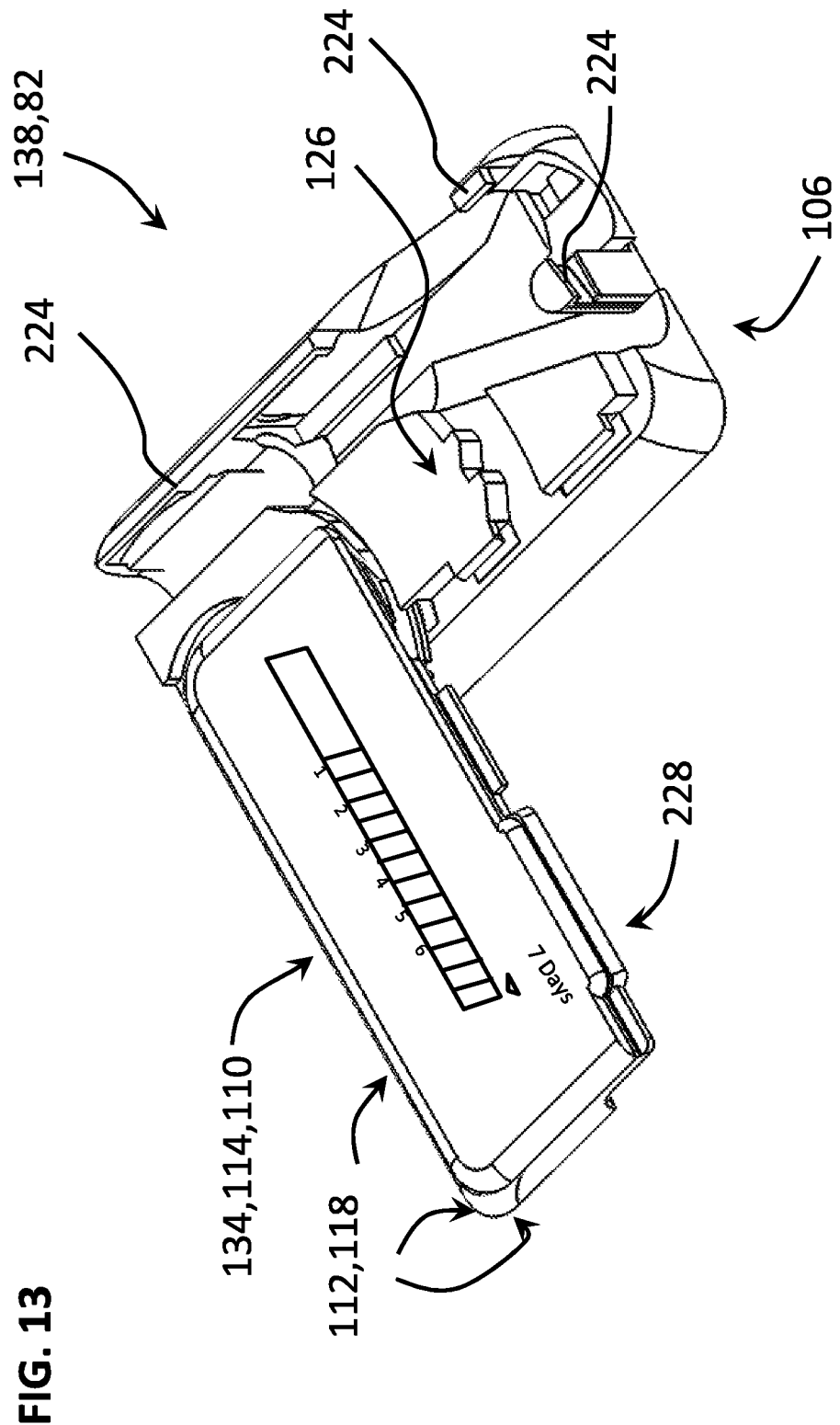
FIG. 13 is an enlarged isometric view of the catheter securement device of FIG. 3, illustrated in the open or unlocked position.
Figure 14:
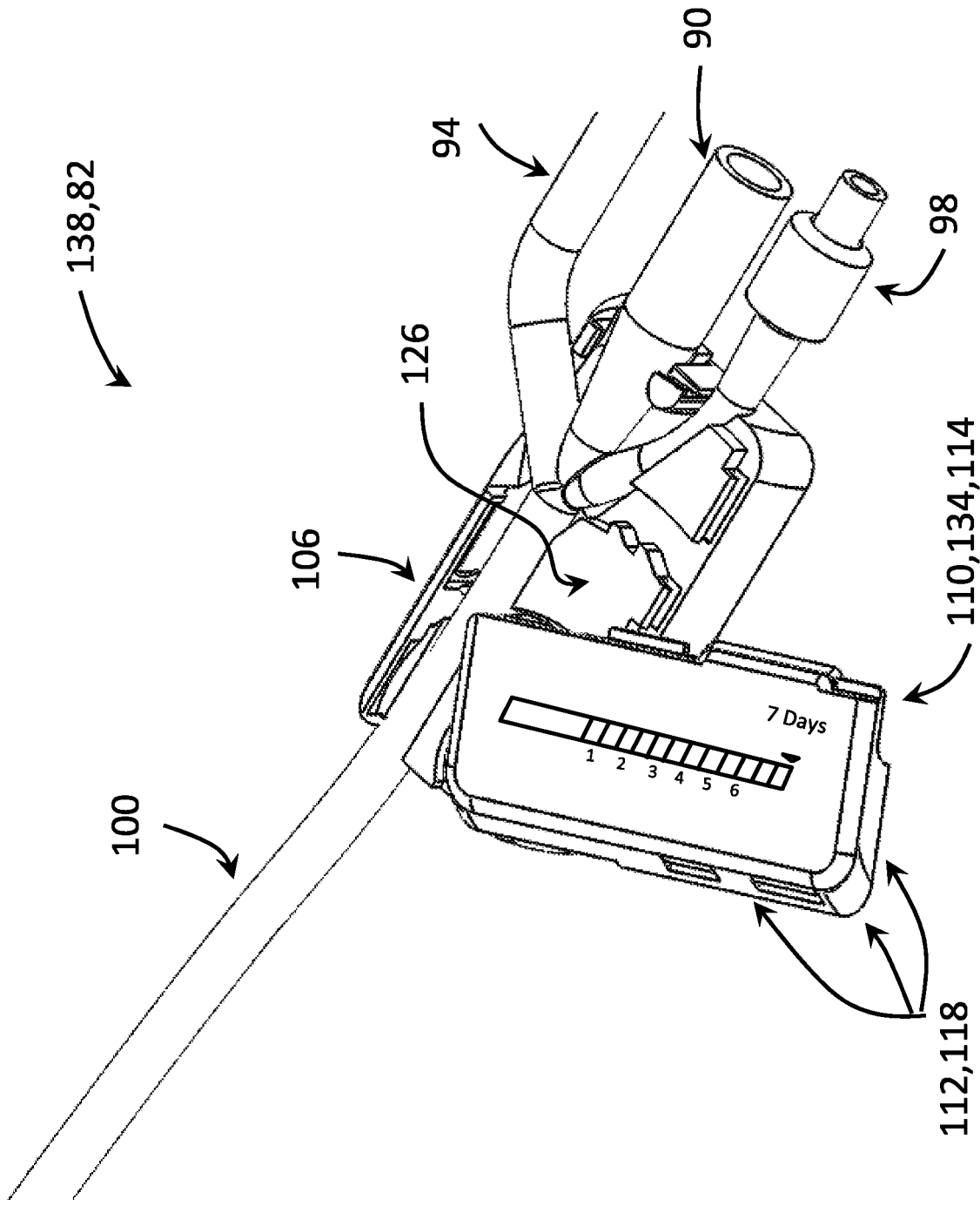
FIG. 14 is an enlarged isometric view of the catheter securement device of FIG. 3, illustrated in the open or unlocked position, revealing the branches of the urinary catheter positioned within the catheter securement device.

As shown in FIGS. 9 and 12, the top side 250 of the timer 114 displays, indicates or otherwise includes: (a) a window or display area 254; (b) a line or series of time period markers 258 (e.g., vertical bars and corresponding "1, 2, 3, 4, 5, 6, 7") positioned in association with each one of the time period markers 258; and (c) time-indicative symbols or time text 262 (e.g., "7 Days").

In operation, once the timer 114 is changed to the active mode, the timer's diffusion process and time-tracking process begins. As the diffusion progresses, the display area 254 will change in color, shade, darkness or visible contrast, starting at the left end 266 and proceeding toward the right end 270. This visible change will gradually enlarge in the time direction 274, gradually passing past the time period markers 258 in sequence. In an embodiment, this gradual enlargement occurs like that of the rising volume of colored liquid in a thermometer. In this example, when the visible change reaches the 7-Days marker 274 (e.g., the downward pointing triangle in FIG. 9), the urinary catheter 86 has been in-use for its designated usage period. The user can therefore easily recognize the need to replace the urinary catheter 86. For example, when the timer 114 is in inactive mode, the display area 254 can be white, gray or black. When the timer 115 is in the active mode and the designated usage period has expired, the display area 254 will have changed from its original non-colored appearance (e.g., white, gray or black) to a solid red color.

As illustrated in FIG. 15, in an embodiment, the body 106 includes an upper body portion 278 and a lower body portion 282. As described below, the upper body portion 278 (while locked with the retainer 110) is configured to be detached from the lower body portion 282. Similarly, as described below, the lower body portion 282 is detachable from the base 130. This enables the base 130 to be replaced if it becomes soiled before the expiration of the designated usage period of the urinary catheter 86. Depending upon the circumstances, such soiling can include urine, fecal material, blood, perspiration or other bodily fluids. Since the upper body portion 278 (and timer 114) remain locked to the urinary catheter 86 during the replacement of the lower body portion 282, the user is unable to wrongfully replace the timer 114 after the expiration of the usage period.

Referring to FIGS. 24-27, in an embodiment, the upper body portion 278 defines at least part of an article-receiving space 286 (e.g., a cavity or recess) which includes: (a) a first passageway or channel 290 configured to receive a portion of the proximal urinary drainage branch 90; (b) a second passageway or channel 294 configured to receive a portion of the proximal inflation branch 94; (c) third passageway or channel 298 configured to receive a portion of the proximal irrigation branch 98; and (d) a fourth passageway or channel 302 configured to receive a portion of the main tube 100.

Referring to FIGS. 24-26, the upper body portion 278 also includes: (a) a compressor 306 configured to apply a compression force to the container bottom 246 (FIG. 21); (b) the body locking member 126; (c) the pivot member 146; and (d) the security lips 224, including side security lips 310, 314 configured to be inserted into the side coupling or security slots 319, 320 (FIG. 22), respectively, of retainer 110.

The compressor 306 has a ramp-shaped, upwardly sloped, or upwardly inclined surface 318. The ramp or inclined surface 318 has a variable height that gradually increase in height, transitioning from a first level 322 (FIG. 24) to a second level 326 (FIG. 24), higher than the first level 322. When the retainer 110 is pivotally fastened to the pivot member 146, the pivot member 146 holds the retainer 110 at a designated or fixed distance from the upper body portion 278. As the retainer 110 is pivoted in the closing or locking direction 330 (FIG. 6), the inclined surface 318 applies a force to the container bottom 246. As the pivoting progresses, this force gradually increases caused by the increasing height of the inclined surface 318. Consequently, the inclined surface 318 squeezes the flexible fluid container 168. This force and squeezing action causes the internal seal (not shown) of the timer 114 to rupture or break which, in turn, changes the timer 114 from the inactive mode to the active mode, as described above.

The body locking member 126 includes a plurality of tooth engagers 334. Each tooth engager 334 has a body slide surface 338 and a body locking surface 188 (FIG. 26). The body slide surfaces 338 are configured to slideably engage the retainer slide surfaces 180 while the retainer is pivoted in the locking direction 330. In this process, the flexible arm 172 (FIG. 23) flexes away from the body slide surfaces 338 while, at the same time, the flexible arm 172 applies an inward force, urging the body slide surfaces 338 toward the body slide surfaces 338. When the retainer 110 is fully closed or locked in the locked position 144, the retainer slide surfaces 180 engage the recess walls 346, and the body locking surfaces 188 mate or otherwise physically engage the retainer locking surfaces 184 (FIG. 23). At this point, the body locking surfaces 188 prevent the flexible arm 172 from becoming disengaged from the upper body portion 278. In an embodiment, this process irreversibly or permanently locks the retainer 110 to the body 106. Therefore, this locked position 144, in an embodiment, prevents users from removing the catheter securement device 62 from the urinary catheter 86, whether based on wrongful or erroneous intent. This provides tamper-resistant or tamper-proof protection for the time-tracking function of the catheter securement device 82.

Figure 27:
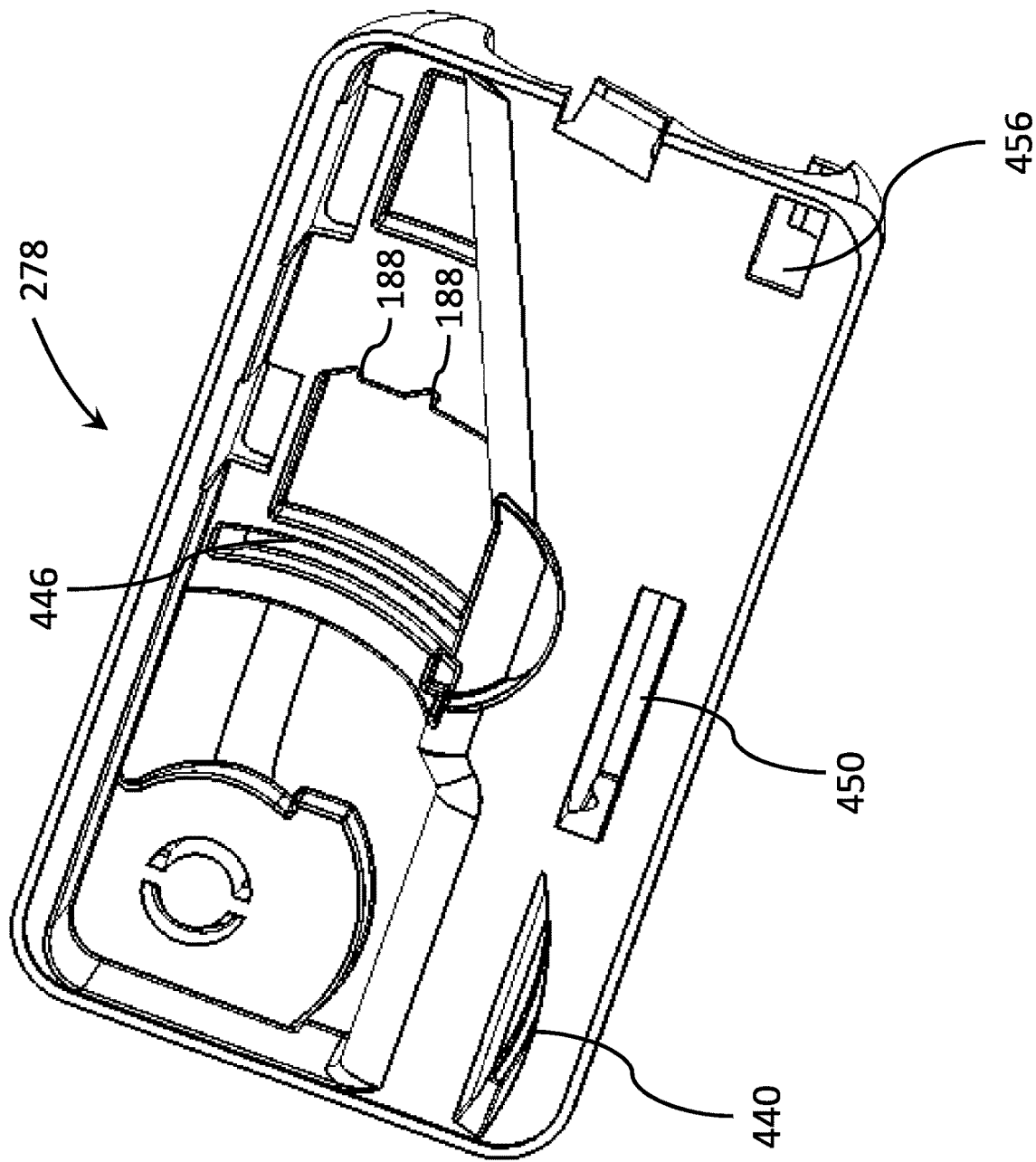
FIG. 27 is a bottom isometric view of an embodiment of the upper body portion of the catheter securement device of FIG. 3.
Figure 28:
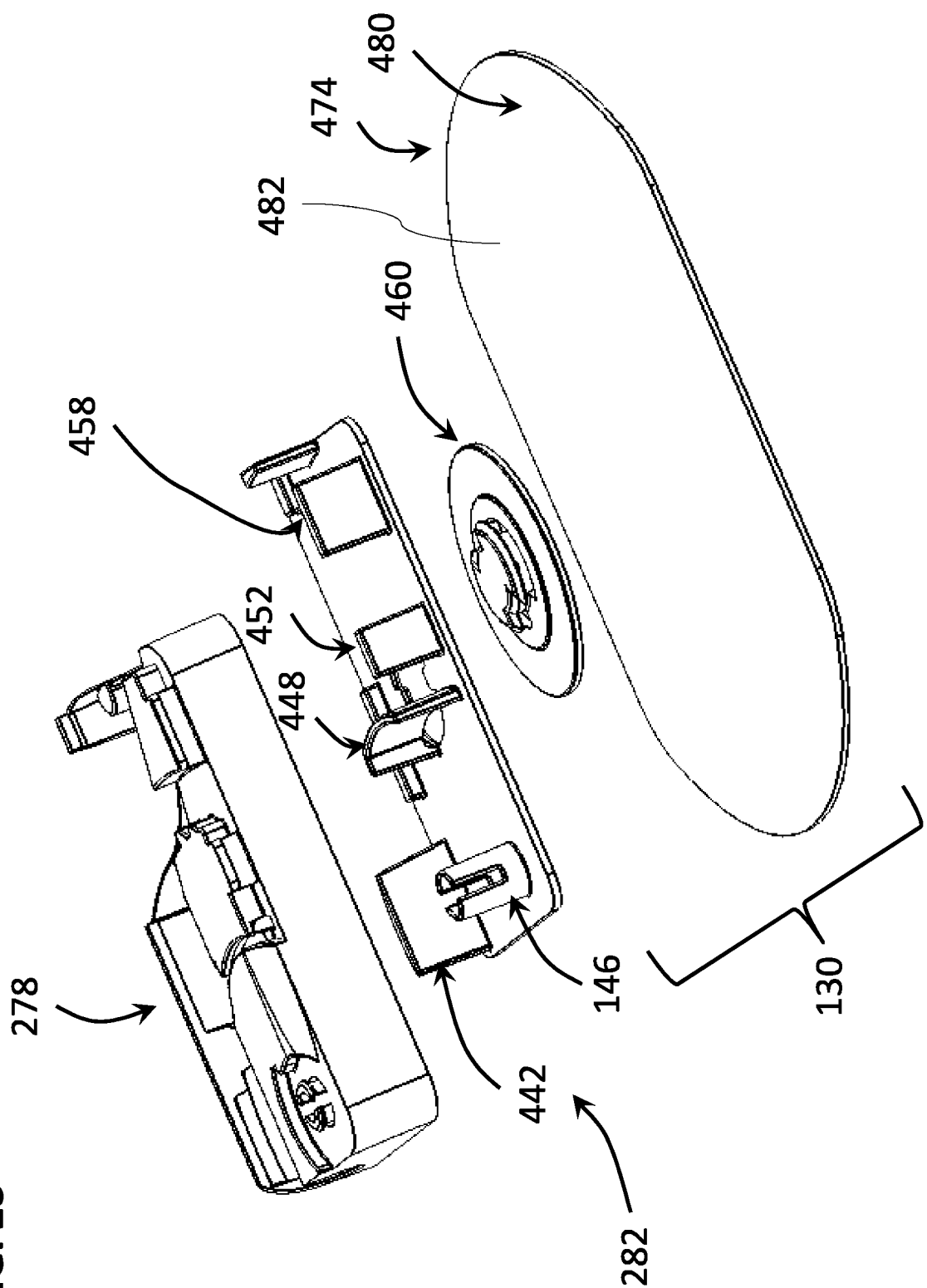
FIG. 28 is another exploded isometric view of embodiments of the upper body portion, lower body portion and other components of the catheter securement device of FIG. 3.

In addition, as illustrated in FIGS. 27-28, the upper body portion 278 of the catheter securement device 82 defines: (a) a first peripheral passage 440 configured to receive, in snap-fit or press-fit configuration, a coupling riser or coupling post 442 of the lower body portion 282; (b) a second peripheral passage 446 having an arc shape configured to receive an arc-shaped support 448 of the lower body portion 282; (c) a third peripheral passage 450 configured to receive, in snap-fit or press-fit configuration, a coupling riser or coupling post 452 of the lower body portion 282; and (d) a fourth peripheral passage 456 configured to receive, in snap-fit or press-fit configuration, a coupling riser or coupling post 458 of the lower body portion 282.

The post 442, support 448 and posts 452, 458 are configured to provide support to the upper body portion 278. Furthermore, one or more of these posts 442, 452, 458 functions to enable the upper body portion 278 to be detachably or removably coupled to the lower body portion 282. This enables a user to replace a soiled base 130 while keeping the retainer 110 and upper body portion 278 locked to the urinary catheter 86.

As illustrated in FIGS. 28-31, in an embodiment, the base 130 includes: (a) a rotary mount or pivot mount 460 having: (i) a neck 462 configured to be inserted through the mount passage 464 that passes through the bottom surface 466 of the lower body portion 282; (ii) a head 468 connected to the neck 462, wherein the head 468 has a head perimeter 470 defining a plurality of head slots 472; and (iii) a mount support 473 that is moveably, rotatable or pivotally coupled to the neck 462; and (b) a tissue interface 474 configured to physically interface with, and engage the tissue (e.g., skin) of the patient.

The mount passage 464 is defined by a perimeter wall 476 which further defines a plurality of tabs, fingers or mount projections 478. To couple the lower body portion 282 to the mount 460, the assembler aligns the mount projections 478 with the head slots 472, then pushes the head 468 through the mount passage 464, then rotates the head 468 relative to the lower body portion 282, and then releases. In an embodiment, this results in a press-fit or friction fit connection that inhibits the unintentional realignment of the mount projections 478 with the head slots 472. Once the head 468 is seated within the lower body portion 282, the mount support 473 is configured to rotate or pivot relative to the lower body portion 282. Depending upon the embodiment, the mount support 473 can be rigid, semi-rigid or flexible.

As illustrated in FIG. 28, the tissue interface 474, in an embodiment, includes: (a) a compliant or compressible body 480 configured to flex or deform to conform to the shape of the patient's tissue; (b) a top surface 482 having a top adhesive (e.g., suitable cement or glue) configured to adhere the compressible body 480 to the mount support 473; and (c) a bottom surface 484 (FIG. 16) having a bottom adhesive and an adhesive cover (not shown) overlying the bottom adhesive.

In an embodiment, the compressible body 480 includes a flexible foam material that is water proof or water resistant. In an embodiment, the adhesive cover is a wax-based substrate or layer configured to preserve the wetness and adhesion characteristics of the bottom adhesive. To adhere the tissue interface 474 to the tissue of a patient, the user peels away the adhesive cover, positions the bottom surface 484 on the tissue, and applies pressure. In doing so, the user attaches the entire catheter securement device 62 to the patient's tissue which, in turn, anchors the urinary catheter 86 to the patient.

Periodically, the indwelling urinary catheter 86 will be subject to forces. These forces can be caused by movement of the patient's legs or torso, the patient grasping the urinary catheter 86, or users (e.g., clinicians) repositioning the indwelling urinary catheter 86 for medical treatment purposes. These forces are first applied to the body 106. In response, the mount support 473 rotates or pivots relative to the body 106. This movement relieves stress so as to reduce binding, kinking or bending of the urinary catheter 86. This relief also avoids or decreases discomfort on the patient's tissue that would otherwise result from such forces.

Figure 33:
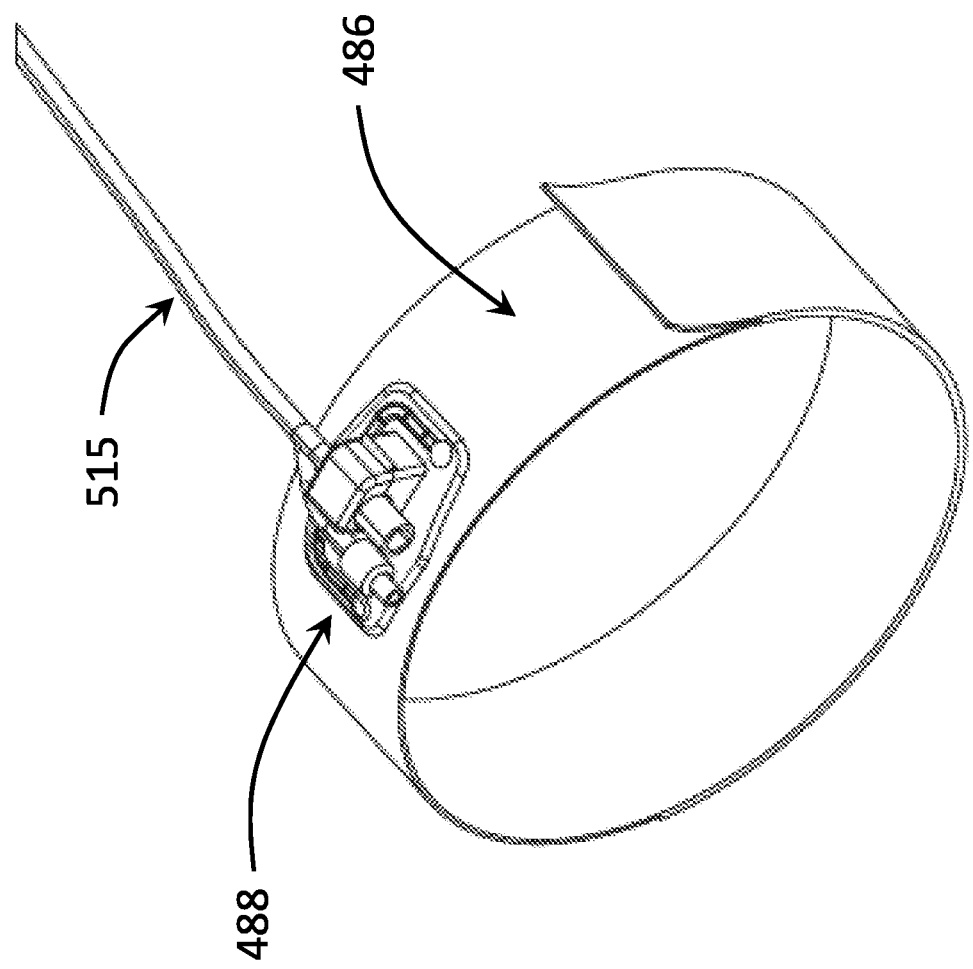
FIG. 33 is an isometric view of the catheter securement device of FIG. 32 locked onto a urinary catheter, illustrating the catheter securement device coupled or mounted to a strap.
Figure 34:
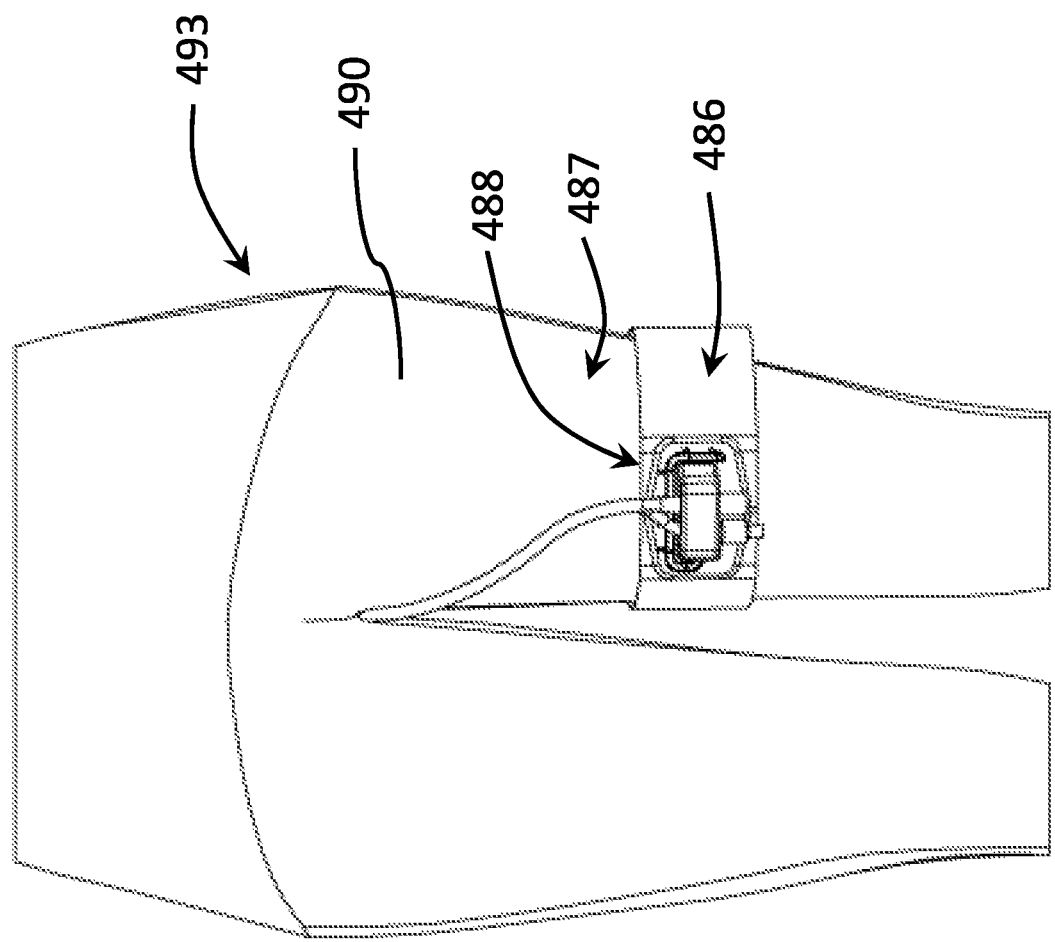
FIG. 34 is an isometric view of the catheter securement device and strap of FIG. 33, illustrating the strap secured to a patient's thigh.

In an embodiment not shown, the catheter securement device 62 is mounted or incorporated into a patient harness or patient strap, such as the strap 486 illustrated in FIG. 33. In such embodiment, the base 130 excludes the tissue interface 474 because the strap 486 includes the tissue interface. Depending upon the embodiment, the base 130 can exclude the mount support 473 and be directly adhered, bonded or otherwise coupled to the strap 486.

In another embodiment illustrated in FIGS. 32-38, the catheter securement device 488 is configured to be adhered to skin tissue 490 of a patient 493 or to the strap 486 (FIG. 33). The strap 486 is configured to be removably attached to a patient's leg, arm or other body part. In the example shown in FIG. 34, the strap 486 is harnessed to the upper leg or thigh 487 of the patient 493.

Figure 39:
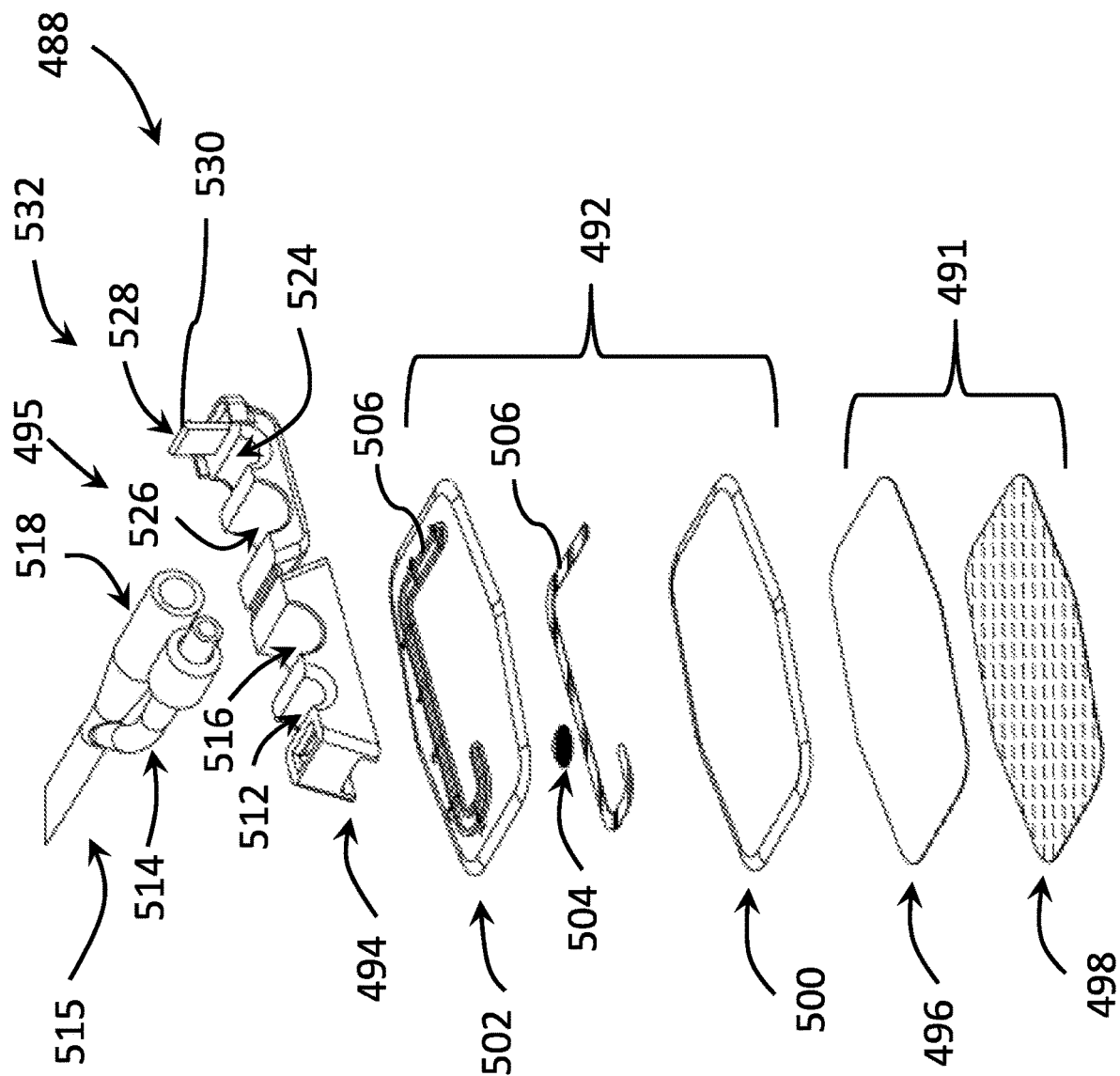
FIG. 39 is an exploded view of the catheter securement device of FIG. 32.
Figure 40:
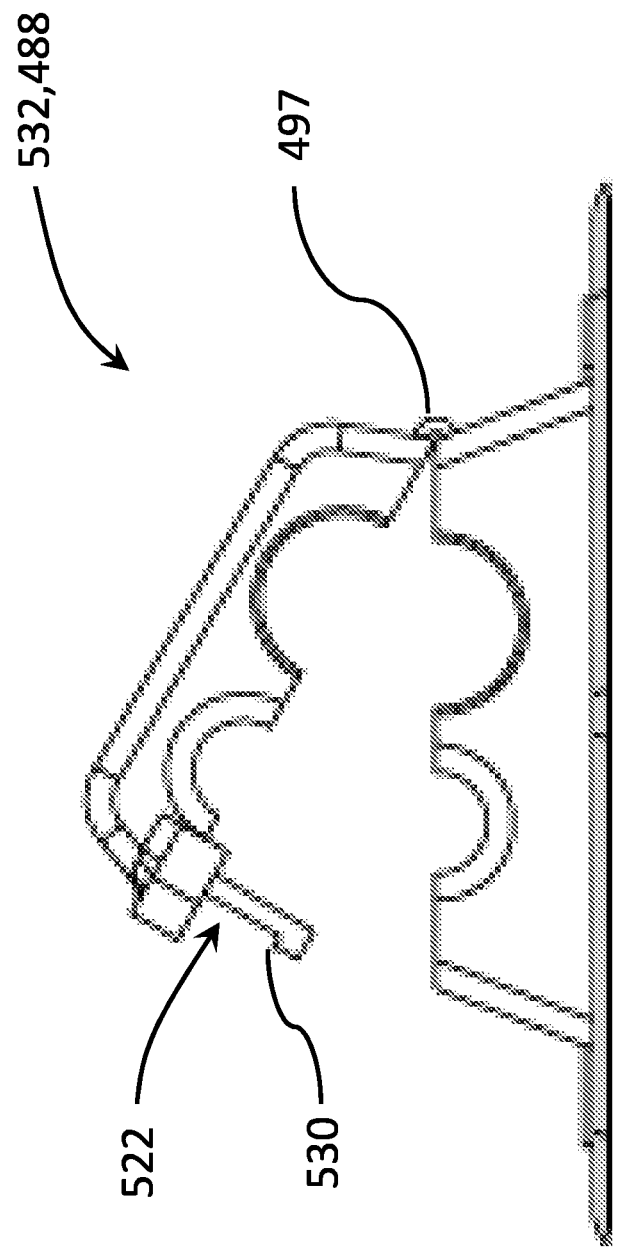
FIG. 40 is a side view of the catheter securement device of FIG. 32, illustrating the catheter securement device in the open or unlocked position.

Referring to FIG. 39, in an embodiment, the catheter securement device 488 includes: (a) base 491 having an adhesive configured to adhere the base 491 to the skin tissue 490 or strap 486; (b) a timer 492 adhered, bonded or otherwise connected to the base 491; (c) a body 494 adhered, bonded or otherwise connected to the timer 492; and (d) a retainer 495 hinged to (and moveably coupled to) the body 494 through hinge 497 (FIG. 40). The base 491 includes a plurality of layers, including a foam layer 496 and a peel-away layer 498 to preserve the unapplied adhesive. The timer 492 includes a lower layer 500, an upper layer 502 (e.g., a top), a plurality of absorptive layers (not shown) between the layers 500, 502, an activator, button or activation member 504, and a display portion 506.

Figure 35:
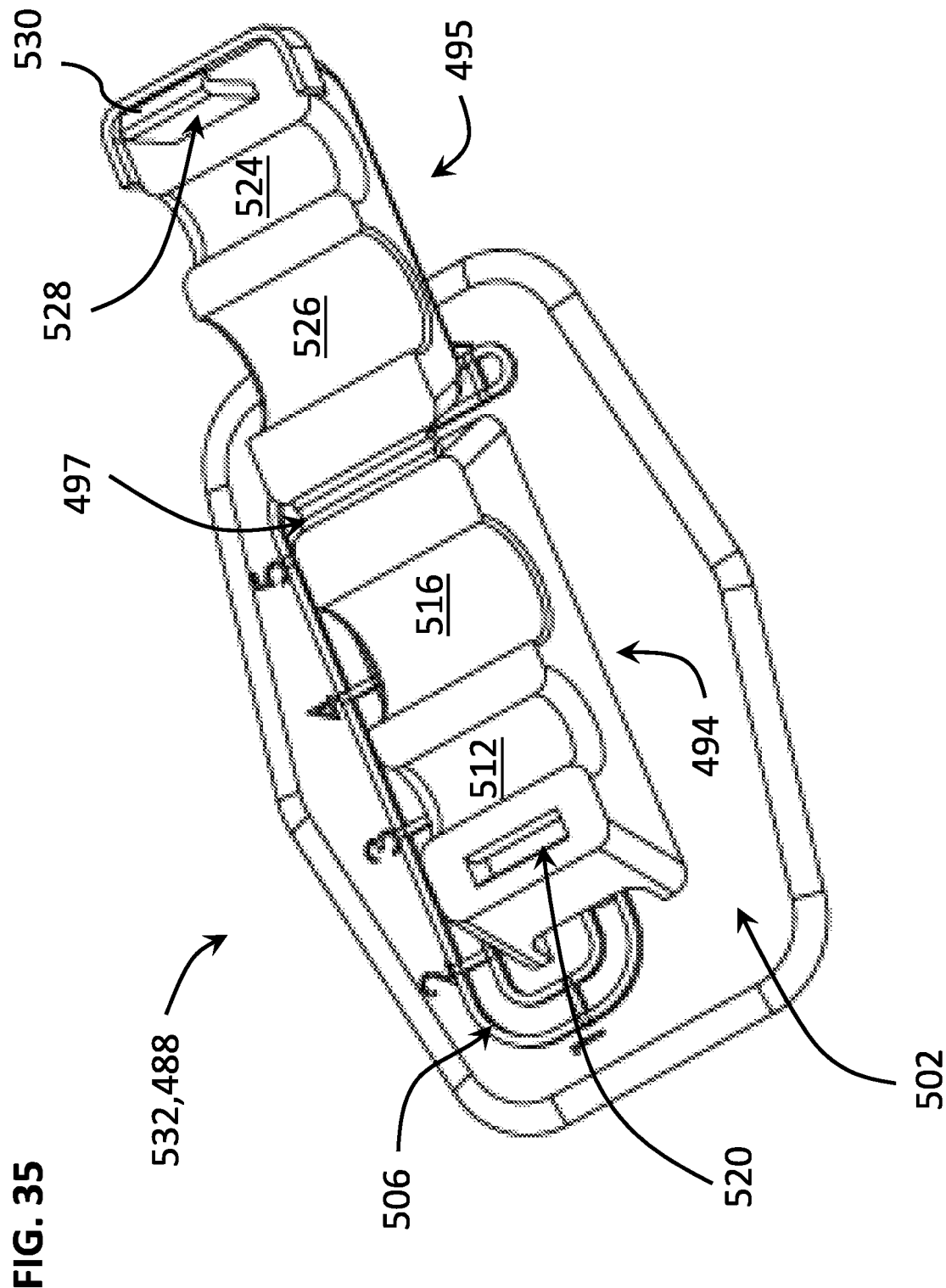
FIG. 35 is a top isometric view of the catheter securement device of FIG. 32, illustrating the catheter securement device in the open or unlocked position.

In an embodiment, timer 492 has the same diffusion-based, time-tracking function as timer 114 described above. As shown in FIG. 35, the body 494 defines: (a) a first article-receiving space 512 configured to receive a first portion of a catheter branch 514 of urinary catheter 515; (b) a second article-receiving space 516 configured to receive a first portion of a catheter branch 518 of urinary catheter 515; and (c) a tooth locker 520 configured to be interlocked with tooth 528 of the retainer 495.

The retainer 495: (a) defines a first article-receiving space 524 configured to receive a second portion of the catheter branch 514; (b) a second article-receiving space 526 configured to receive a second portion of the catheter branch 518; and (c) a tooth 528 configured to be inserted into the tooth locker 520. The tooth 528 is predisposed to exert a biasing force on the tooth locker 520 to urge the projection 530 into irreversible or permanent, locking engagement with the tooth locker 520.

Figure 41:
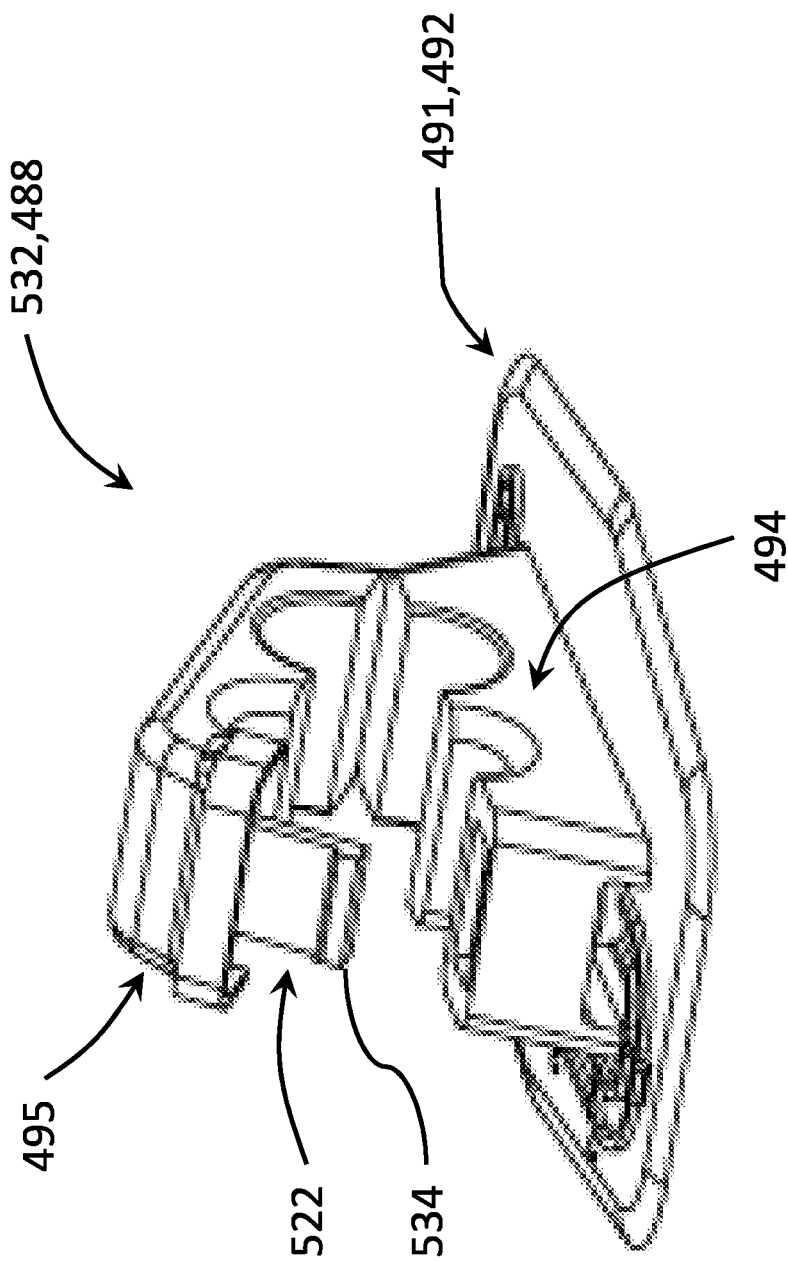
FIG. 41 is an isometric view of the catheter securement device of FIG. 32, illustrating the catheter securement device in the open or unlocked position.
Figure 42:
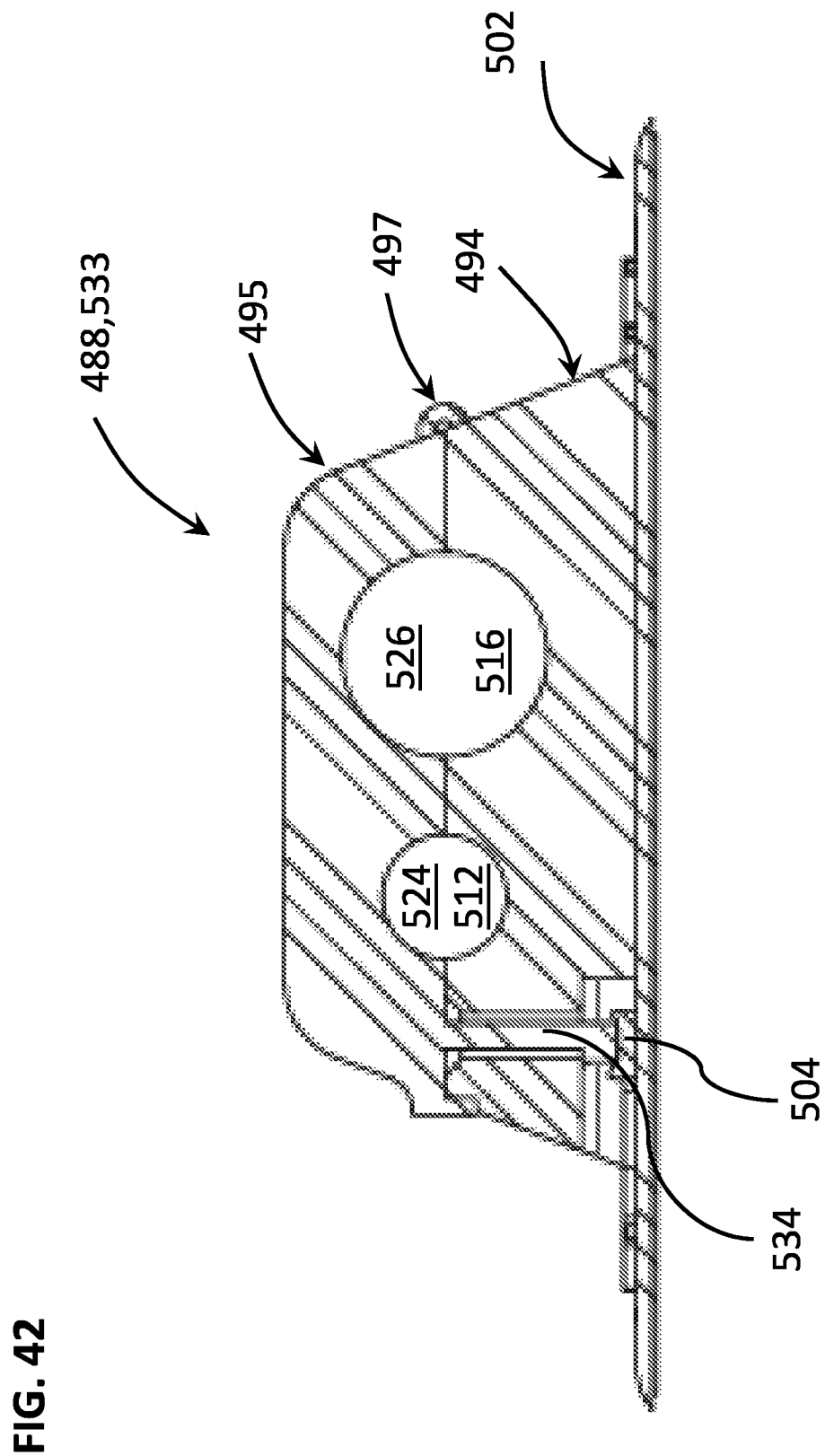
FIG. 42 is a cross-sectional view of the catheter securement device of FIG. 32, taken substantially along line 42-42 of FIG. 36, illustrating the catheter securement device in the closed or locked position.

In operation, the user inserts the branches 514, 518 into the catheter securement device 488 when the catheter securement device 488 is in the unlocked position 532 (FIGS. 39-41). Next, the user applies a single action 54 (e.g., a downward force) to the retainer 495. As a result of the single action 54: (a) the tooth 528 travels through the tooth locker 520, and the tooth end 534 (FIGS. 41-42) makes contact with, and applies a force to, the activation member 504; and (b) the tooth 528 become locked together with the tooth locker 520, thereby causing continuous application of such force on the activation member 504. In an embodiment, this force ruptures an internal seal or membrane of the timer 492, causing the timer 492 to change to the active mode for indicating the passage of time. In another embodiment, this force causes the liquid in the timer 492 to diffuse throughout the timer 492, causing the timer 492 to change to the active mode for indicating the passage of time. Due to this single action 54, the catheter securement device 488 is changed to the locked position 533 (FIGS. 36 and 42).

Figure 36:
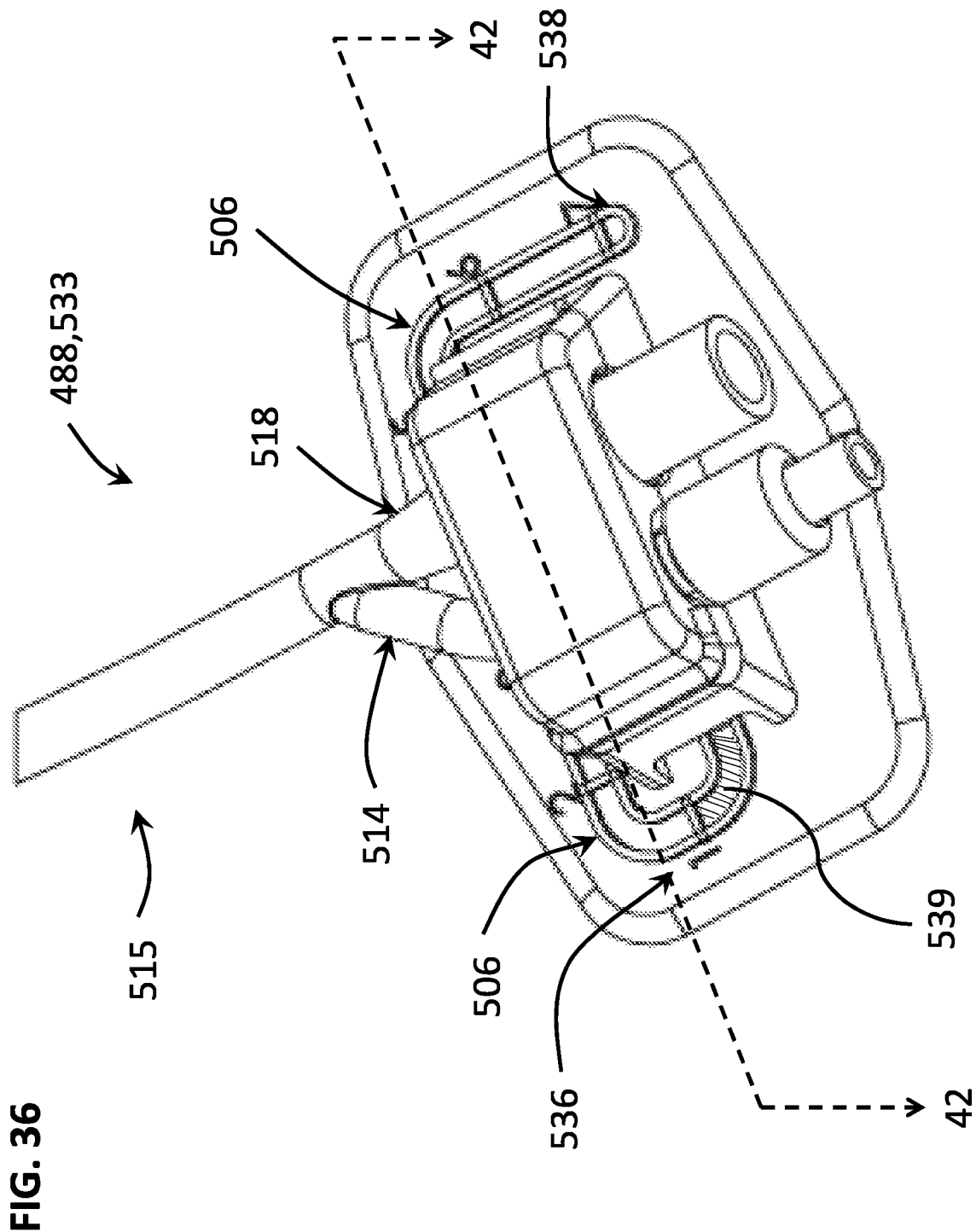
FIG. 36 is a top isometric view of the catheter securement device of FIG. 32 locked onto a urinary catheter, illustrating the catheter securement device in the closed or locked position.
Figure 37:
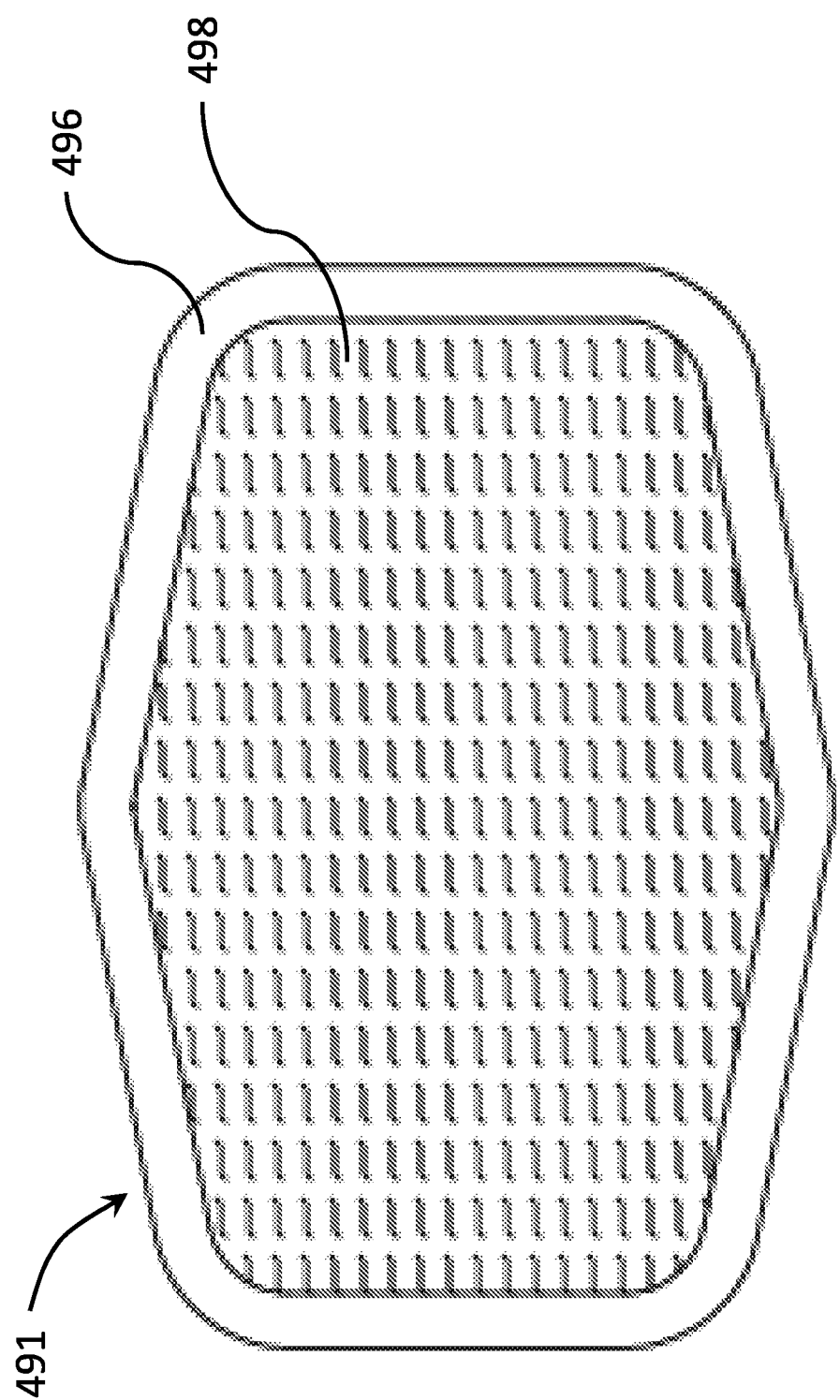
FIG. 37 is a bottom view of the catheter securement device of FIG. 32.
Figure 38:
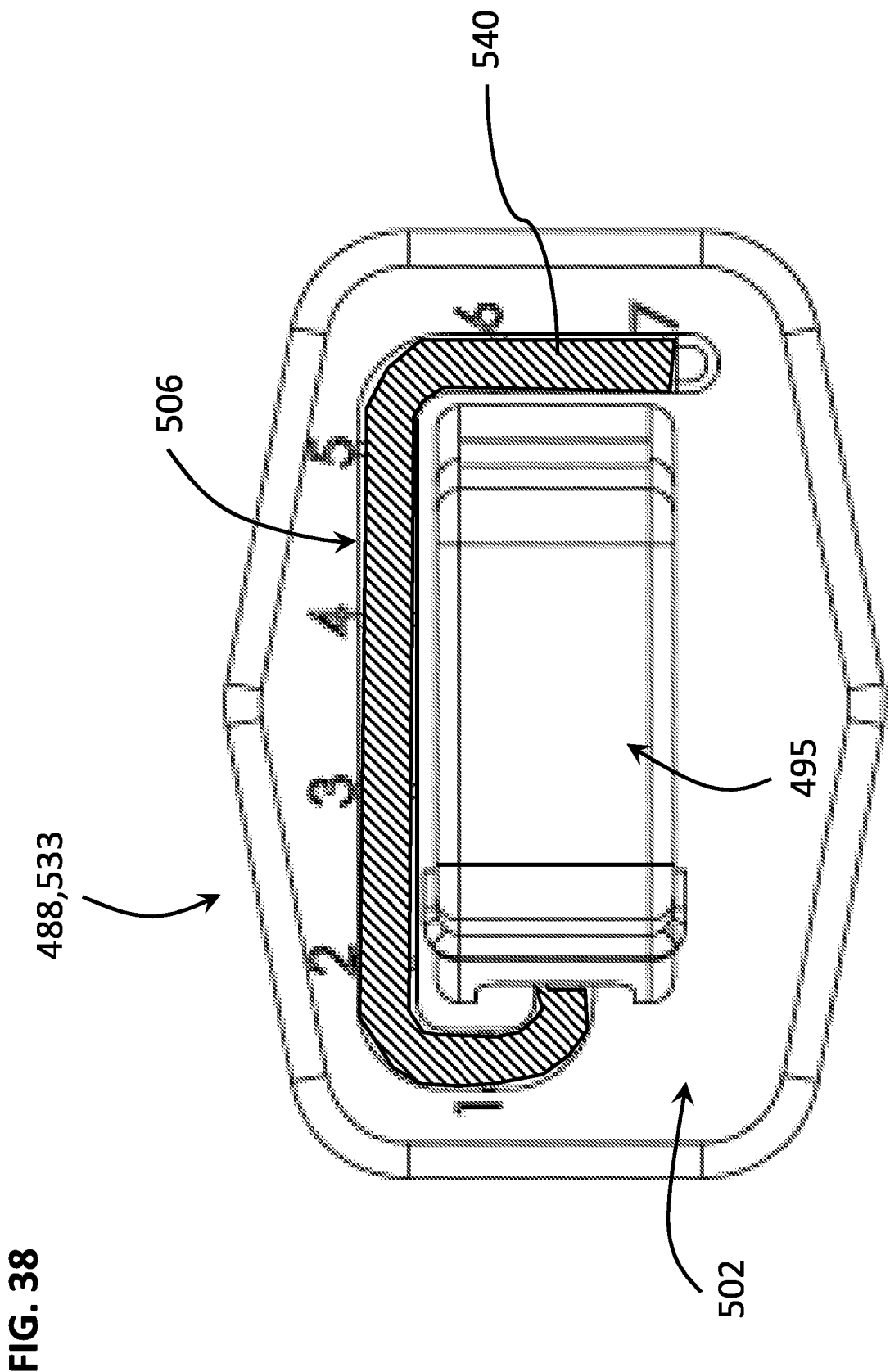
FIG. 38 is a top view of the catheter securement device of FIG. 32.

As illustrated in FIGS. 36 and 38, the display portion 506 displays or indicates a continuous indicator (e.g., color contrast), gradually expanding from starting period marker 536 to ending period marker 538. In this example, ending period marker 538 indicates a seven day usage period, the designated usage period for the urinary catheter 515. At day one, the timer 492 displays an initial color contrast level 539 (FIG. 36), and at day seven, the timer 492 displays the ending color contrast level 540 (FIG. 38) associated with the expiration of the designated usage period.

In another embodiment illustrated in FIGS. 43-46, the catheter insertion dressing or catheter insertion cover 544 is configured to cover the site 546 at which a venous catheter 548 is inserted through a hole in the skin 550 of a patient 553. The venous catheter 548 can be a central venous catheter including intravenous (IV) tubing for continuous access to the central vein of the patient for administering fluids and medicines over time. In this embodiment, the catheter insertion cover 544 includes a flexible body 551. The body 541 defines a transparent or see-through window 552 configured to overlay the hole in the skin 550. The body 551 also defines a cut-out or slot 554 configured to receive a connector 557 of the venous catheter 548. The top 559 reveals or displays a display portion 556 having period markers 558. The bottom 560 (FIG. 44) has an adhesive layer covered by a peel-away layer.

In an embodiment, the catheter insertion cover 544 includes: (a) a button or time activation member 562; and (b) a timer having the same structure, functionality and elements as the timer 492 described above. To deploy the catheter insertion cover 544, the user prepares the skin site 546 and then inserts the venous catheter 548 into the patient's central vein. Next, the user removes the peel-away layer from the bottom 560 of the catheter insertion cover 544. Next, the user positions the bottom 560 onto the skin 550 so that the window 552 covers the site 546, and the connector 557 is located within the slot 554. Finally, the user can apply a single action 54, such as a palm or finger pressing force on the top 559. This force, including a sub-force applied to the time activation member 562, causes the timer to enter into the active mode, and it also causes the catheter insertion cover 544 to be adhered to the patient. In an embodiment, this force ruptures in internal seal or membrane of the timer, causing the timer to change to the active mode for indicating the passage of time. In another embodiment, this force causes the liquid in the timer to diffuse throughout the timer, causing the timer to change to the active mode for indicating the passage of time.

Figure 43:
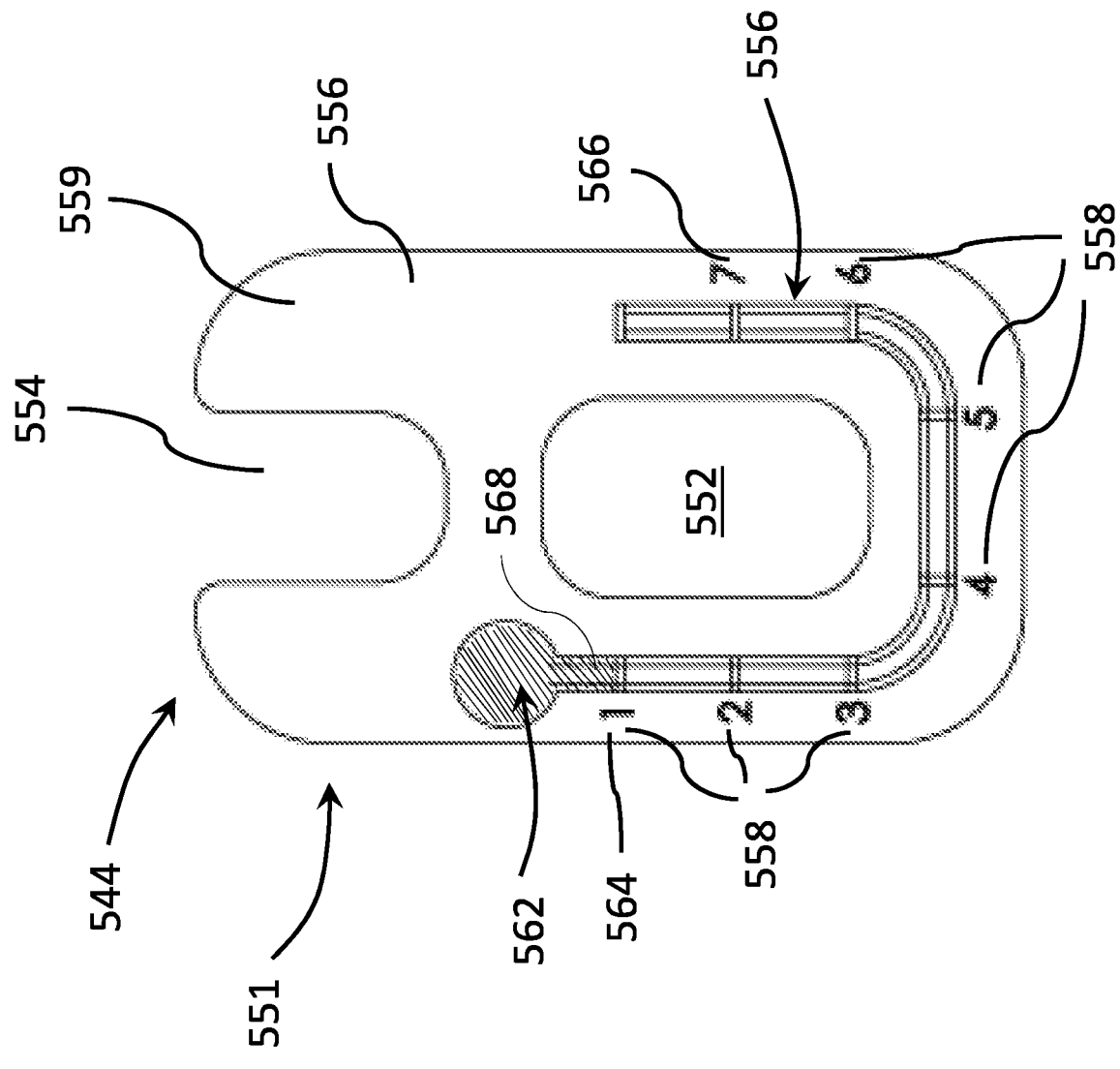
FIG. 43 is a top view of an embodiment of a catheter insertion cover.
Figure 44:
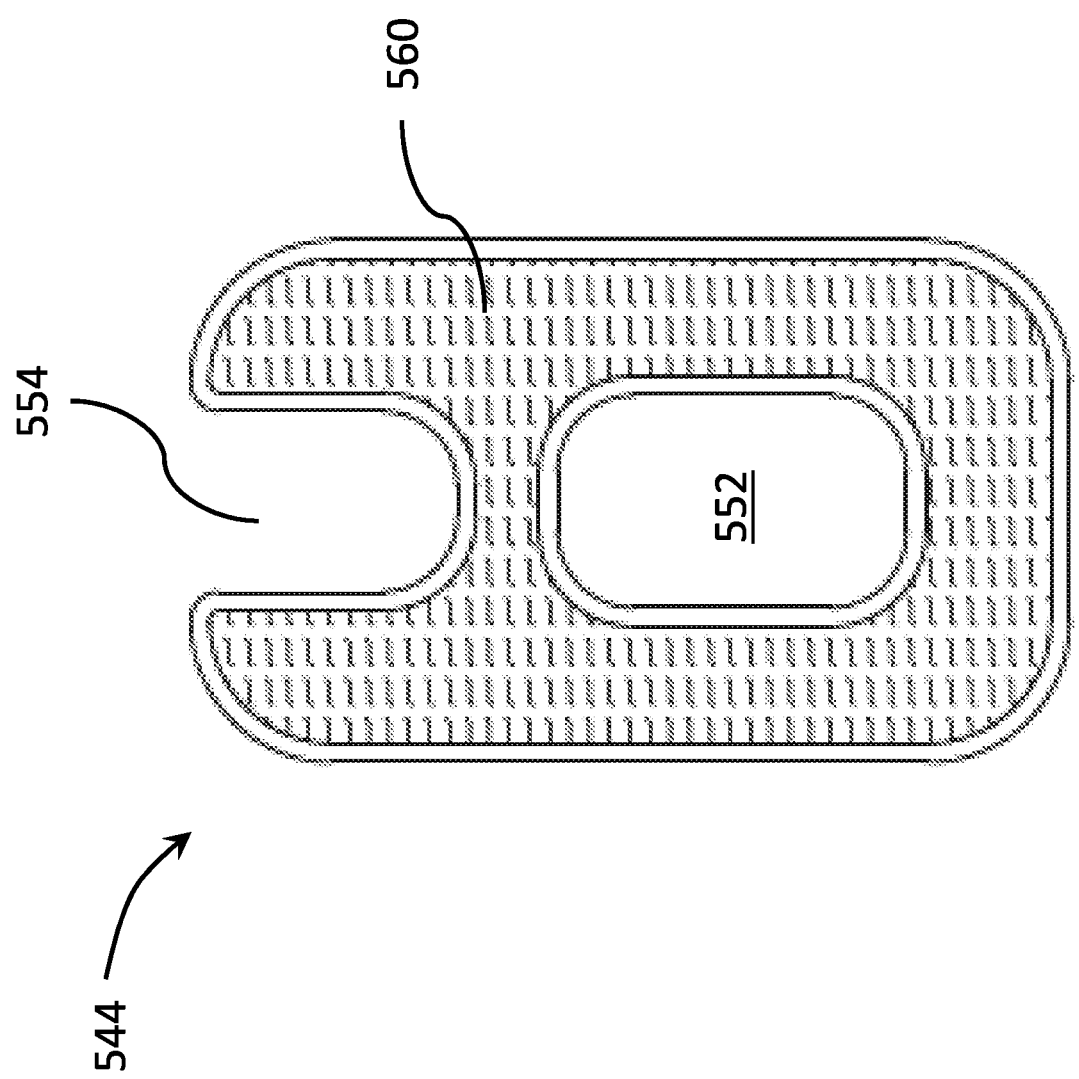
FIG. 44 is a bottom view of the catheter insertion cover of FIG. 43.
Figure 45:
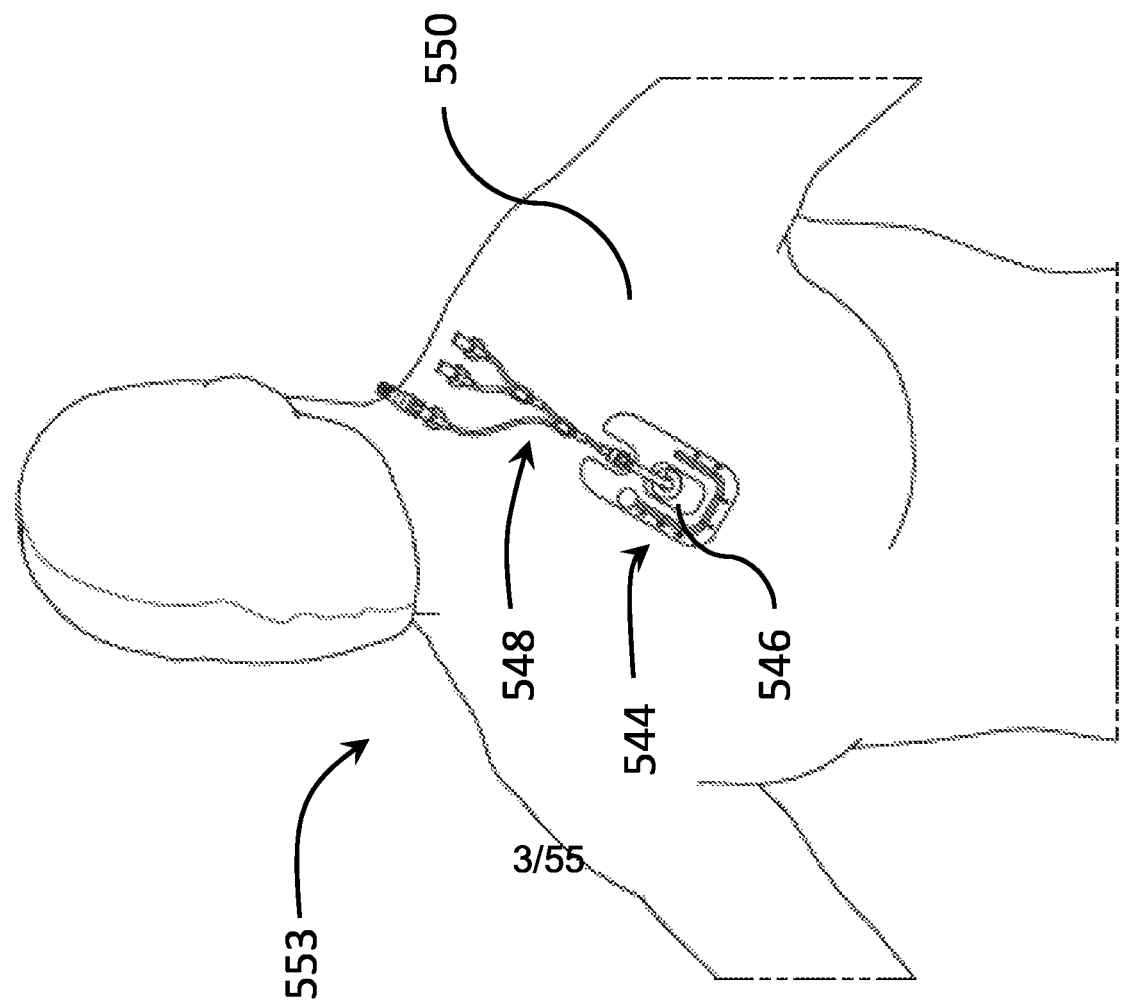
FIG. 45 is an isometric view of the catheter insertion cover of FIG. 43 covering the part of a venous catheter entering the skin of a patient.
Figure 46:
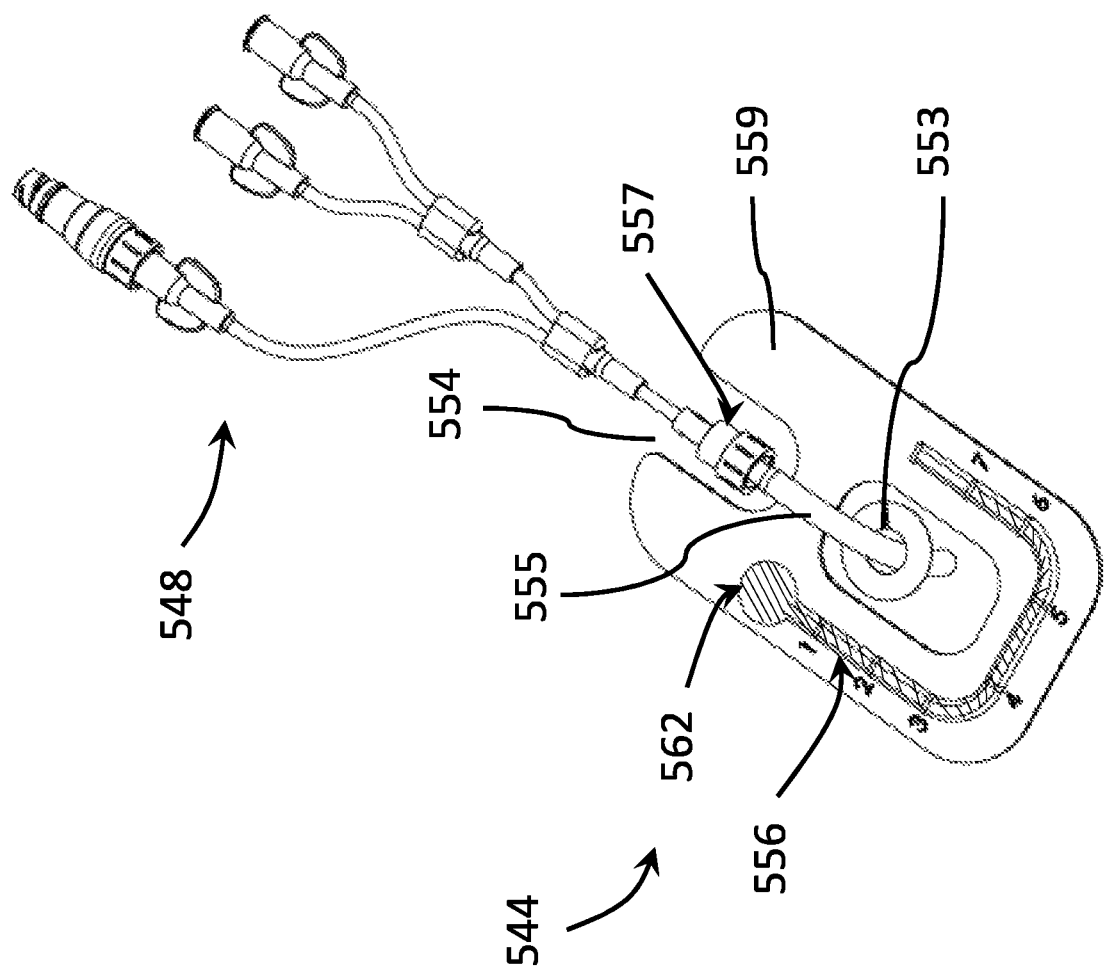
FIG. 46 is an enlarged, isometric view of the catheter insertion cover of FIG. 43.

As illustrated in FIGS. 43 and 46, the display portion 556 displays or indicates a continuous indicator (e.g., color contrast), gradually expanding from starting period marker 564 to ending period marker 566. In this example, ending period marker 566 indicates a seven day usage period, the designated usage period for the venous catheter 548. At day one, the timer displays an initial color contrast level 568 (FIG. 43), and at day seven, the timer displays the ending color contrast level 570 (FIG. 46) associated with the expiration of the designated usage period.

In another embodiment illustrated in FIGS. 47-50, the medical timing device 572 is configured to be locked to any medical tube 574 for purposes of tracking and indicating the in-use time of the medical tube 574 or the medical equipment attached to the medical tube 574. The medical tube 574 can include, without limitation, an IV bag tube, a feeding bag tube or any other tube used for medical purposes. In the example illustrated, the medical timing device 572 is used to track the in-use time of IV tube 574 fluidly connected to an IV bag 576.

Figure 47:
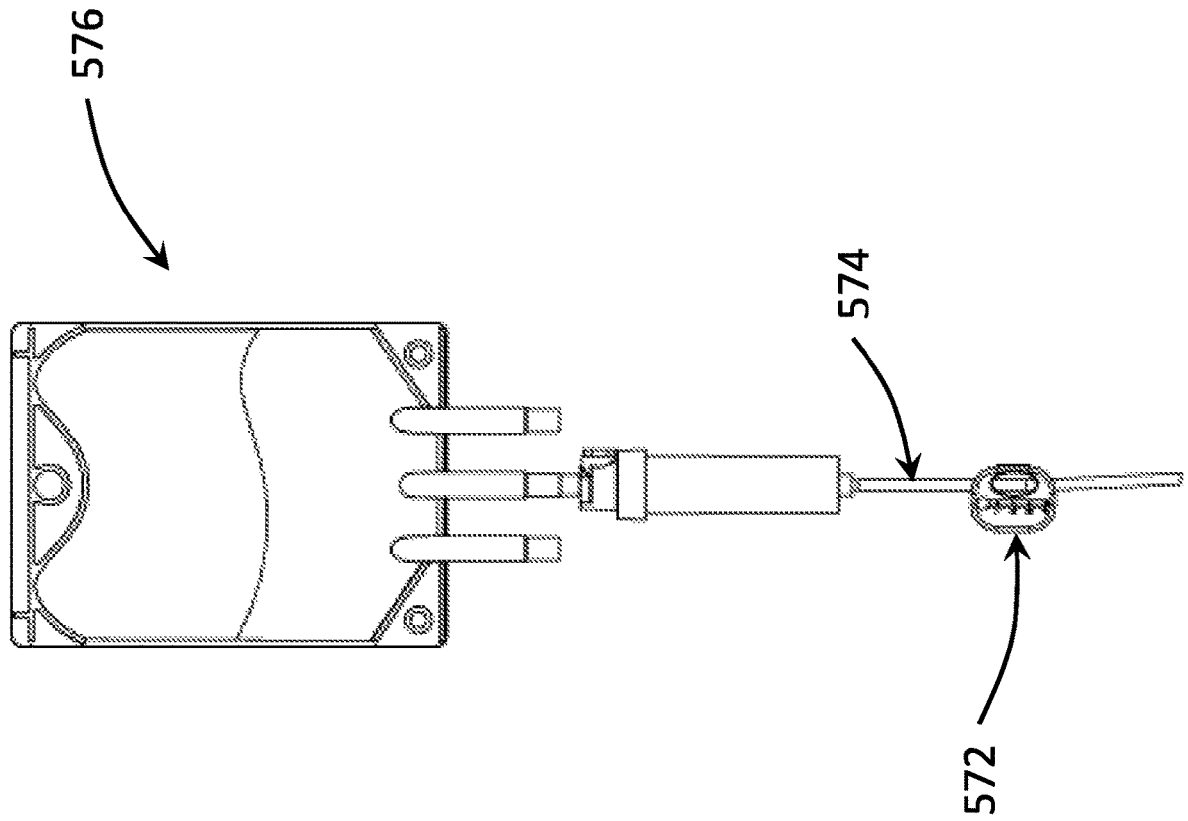
FIG. 47 is a front view of yet another embodiment of a medical timing device, illustrated locked onto an IV tube which, in turn, is connected to an IV bag.
Figure 48:
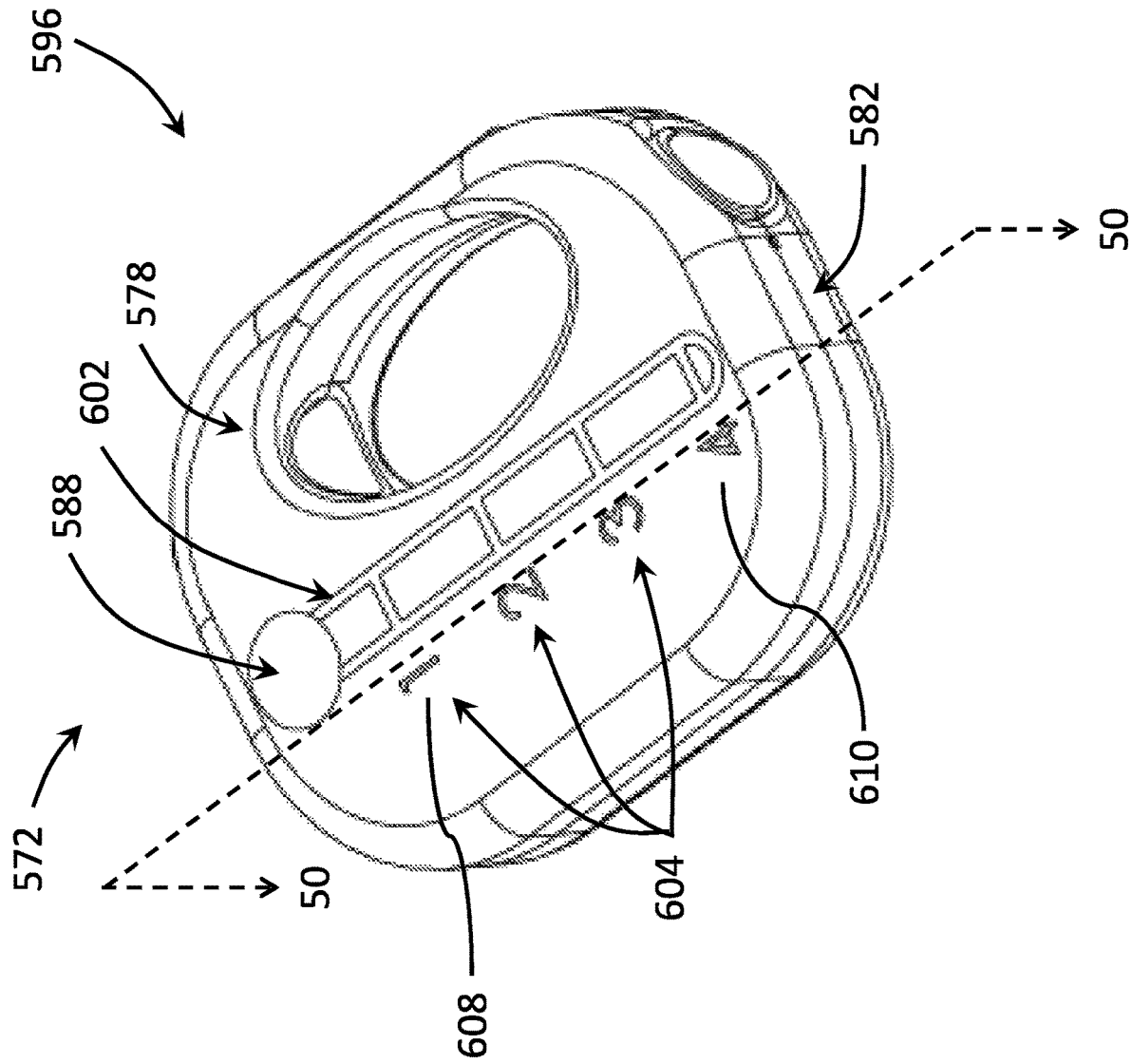
FIG. 48 is a top isometric view of the medical timing device of claim 47, illustrated in the closed or locked position.

In this embodiment, the medical timing device 572, having a clam shell configuration, includes: (a) a first portion 578 defining a first tubular channel 580 configured to receive a first portion of the medical tube 574; (b) a second portion 582 moveably coupled to the first portion 578 through a hinge 584, wherein the second portion 582 defines a second tubular channel 586 configured to receive a second portion of the medical tube 574; (c) a button or time activation member 588 coupled to the first portion 578; (d) a ram or driver 590 coupled to the second portion 582 and configured to make contact with, and apply a force to, a timer activation portion 592 (FIG. 50), such as an internal seal or membrane of the timer described below; (e) a plurality of frictional, traction or gripping members 594 configured to frictionally or adhesively engage the medical tube 574 when the medical timing device 572 is clamped onto the medical tube 574 in the locked position 596 (FIGS. 47-48); (f) a plurality of one-way fasteners or locking members 598 coupled to the first portion 578 which are configured to be irreversibly secured to or locked with the second portion 582 when the locking members 598 are inserted through the lock openings 600 defined by the second portion 582; (g) a display portion 602 coupled to the first portion 578, wherein the display portion 602 displays a series of period markers 604; and (h) a timer having the same structure, functionality and elements as the timer 492 described above.

Figure 49:
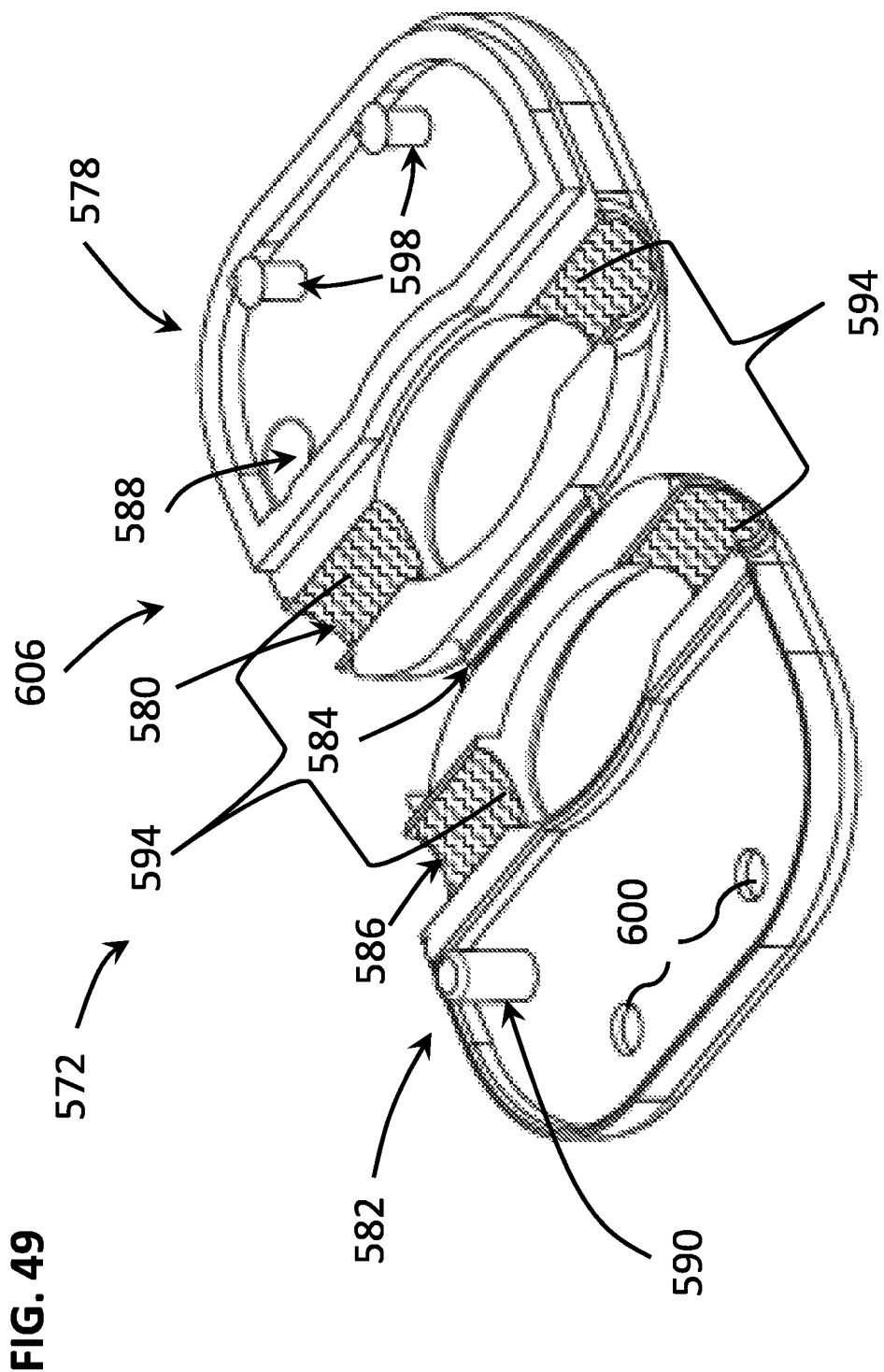
FIG. 49 is a top isometric view of the medical timing device of claim 47, illustrated in the open or unlocked position.

To deploy the medical timing device 572, the user separates the portions 578, 582 to achieve the unlocked position 606 illustrated in FIG. 49. Next, the user inserts the medical tube 578 into the channels 580, 586. Next, the user closes the medical timing device 572 to reach the locked position 596. In the locked position 596, the gripping members 594 engage the medical tube 574 (FIG. 47) to inhibit the medical timing device 572 from undesirably sliding on the medical tube 574. Also, in the locked position 596, the locking members 598 are locked together with the structure of the second portion 582 that defines the lock openings 600.

Figure 50:
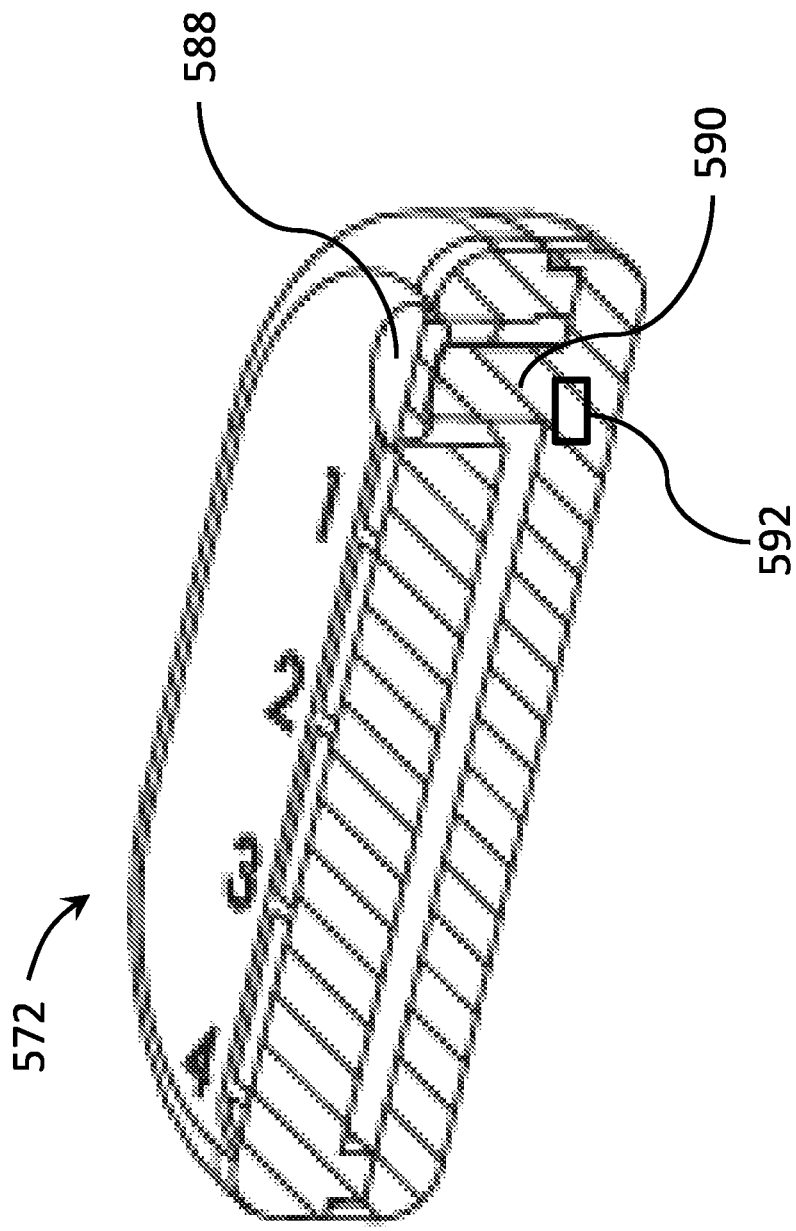
FIG. 50 is a cross-sectional view of the medical timing device of claim 47, taken substantially along line 50-50 of FIG. 48, illustrating the medical timing device in the closed or locked position.
Figure 51:
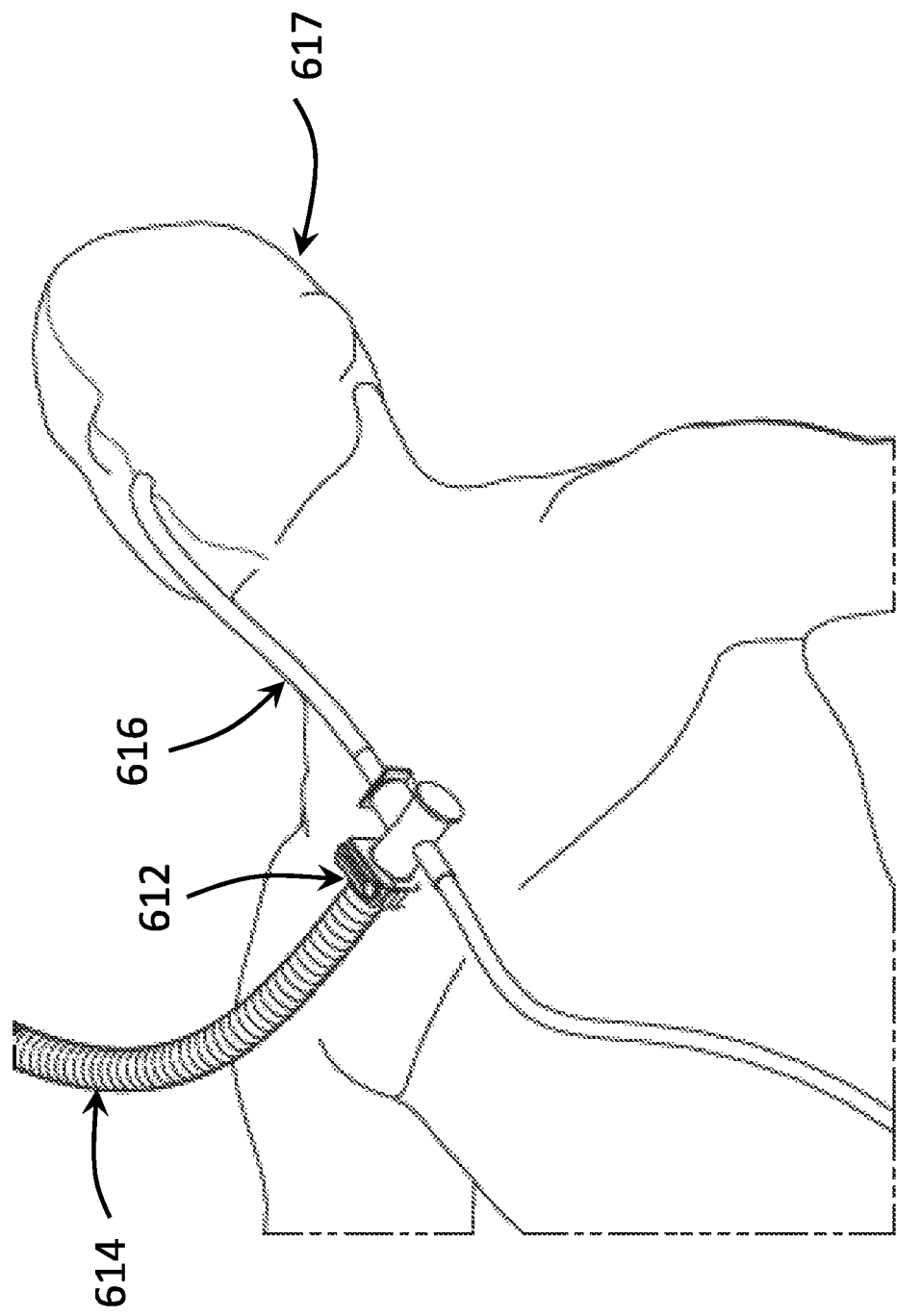
FIG. 51 is an isometric view of a further embodiment of a medical timing device locked onto a ventilation tube, illustrating the medical timing device in the closed or locked position.

Next, the use presses the actuator or time activation member 588, which causes the driver 590 to apply a force to the timer activation portion 592 (FIG. 50). This force causes the timer to enter into the active mode. In an embodiment, this force ruptures in internal seal or membrane of the timer, causing the timer to change to the active mode for indicating the passage of time. In another embodiment, this force causes the liquid in the timer to diffuse throughout the timer, causing the timer to change to the active mode for indicating the passage of time. The display portion 602 displays or indicates a continuous indicator (e.g., color contrast), gradually expanding from starting period marker 608 (indicating day one) to the ending period marker 610 (indicating day four). In this example, ending period marker 610 indicates a four day usage period, the designated usage period for the medical tube 574 or its permanently attached equipment (e.g., IV bag 756).

Figure 52:
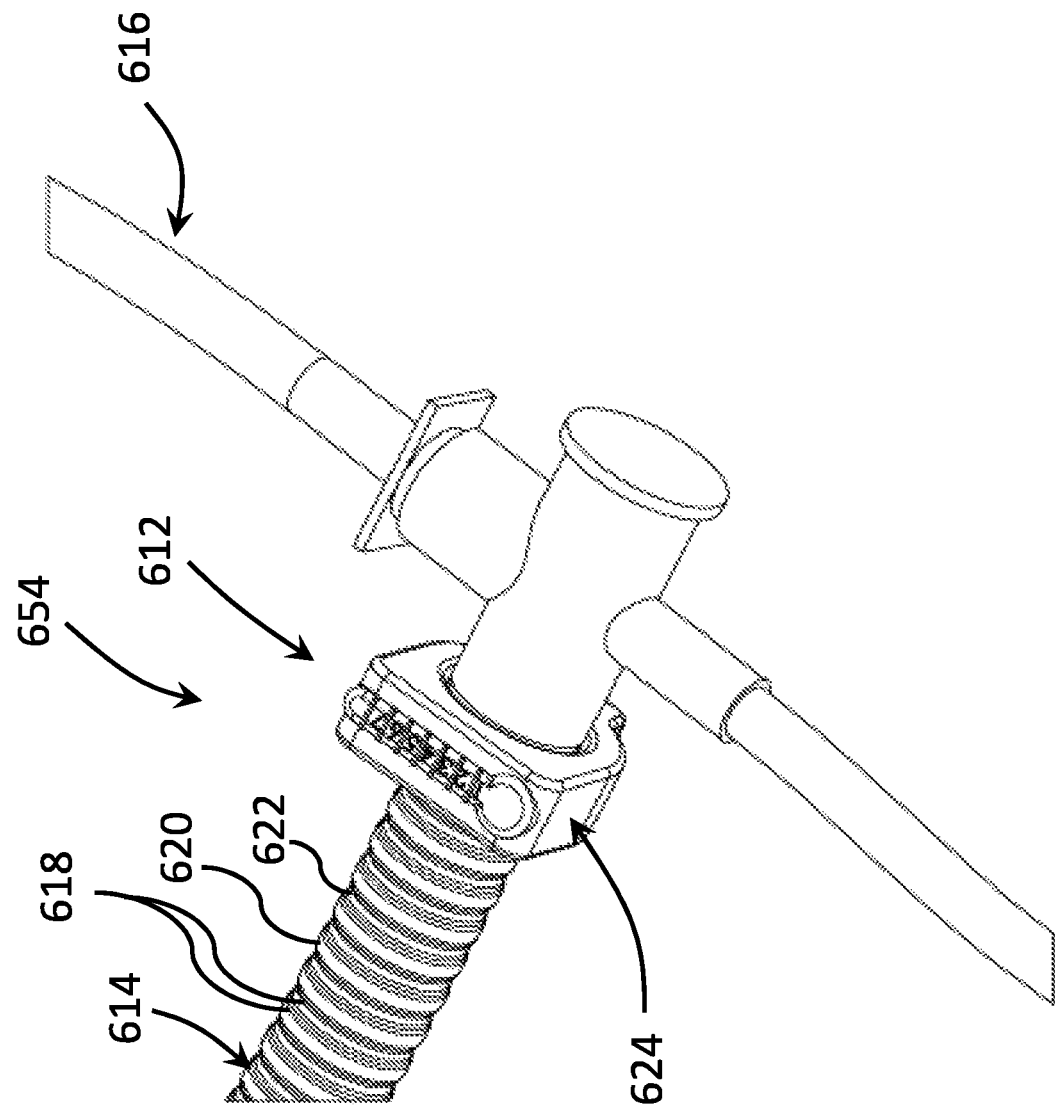
FIG. 52 is an enlarged isometric view of the medical timing device of FIG. 51 locked onto the ventilation tube, illustrating the medical timing device in the closed or locked position.

In another embodiment illustrated in FIGS. 51-55, the medical timing device 612 is configured to be locked to a corrugated ventilation tube 614 which, in turn, is fluidly connected to an endotracheal tube 616. The endotracheal tube 616 is configured to be inserted into the trachea of a patient 617, and ventilation tube 614 delivers air through the endotracheal tube 616 based on air supplied by a ventilator or breathing machine. In the embodiment illustrated, the endotracheal tube 616 has a corrugated exterior surface 618, as illustrated in FIG. 52. The corrugated exterior surface 618 has a series of spaced-apart ridges or a series of peaks 620 and valleys 622 configured to add some degree of stiffness to the ventilation tube 614 while enabling the ventilation tube 614 to be flexed or bent without kinking.

Figure 53:
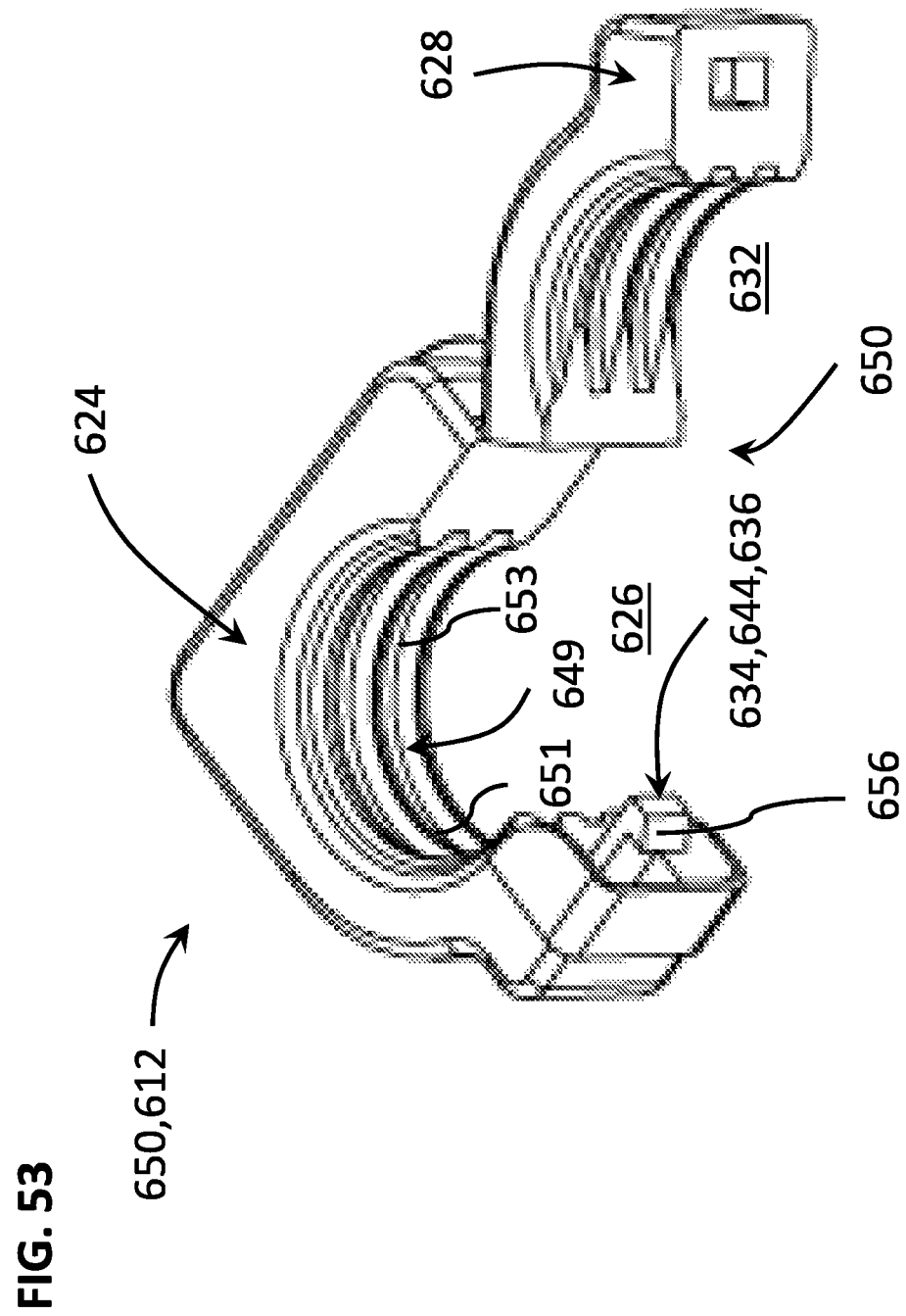
FIG. 53 is an enlarged isometric view of the medical timing device of FIG. 51, illustrating the medical timing device in the open or unlocked position.
Figure 54:
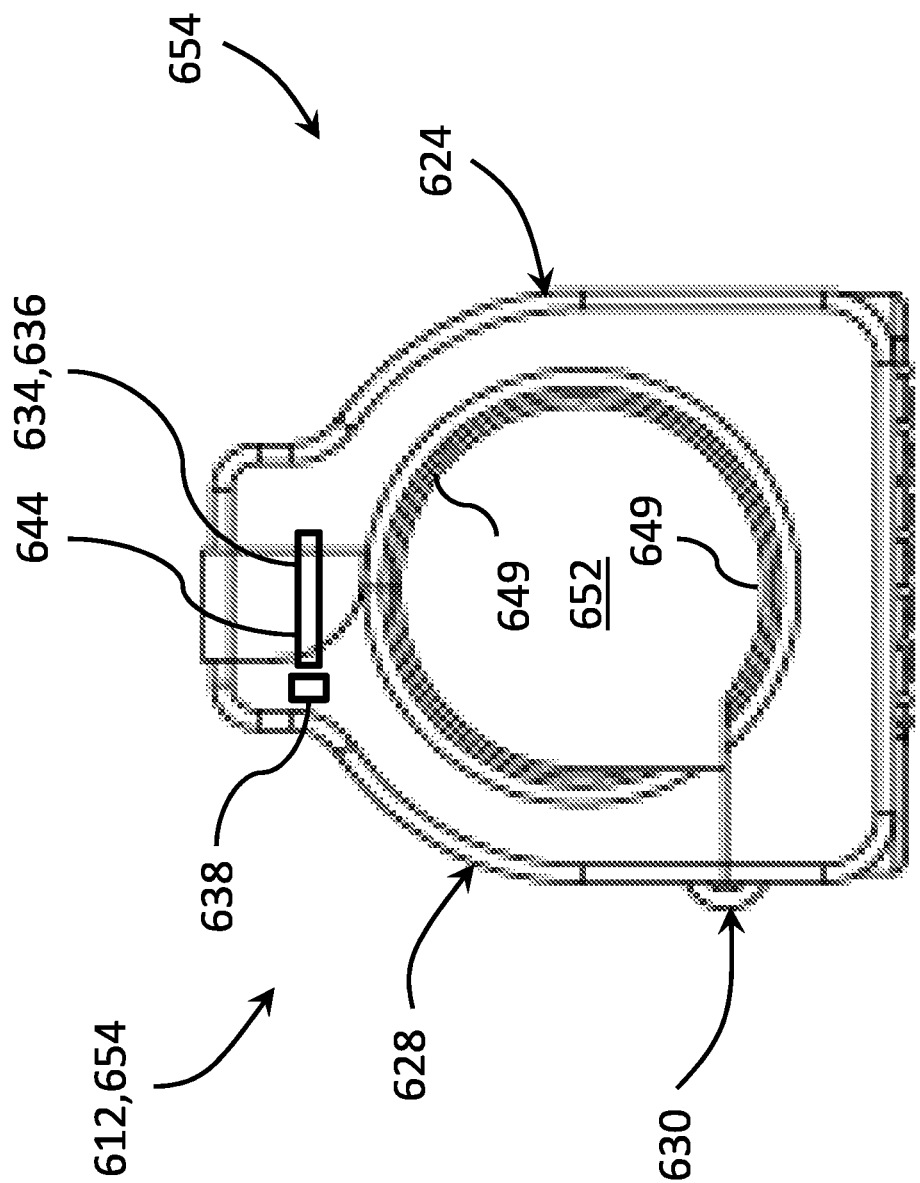
FIG. 54 is an enlarged side view of the medical timing device of FIG. 51, illustrating the medical timing device in the closed or locked position.
Figure 55:
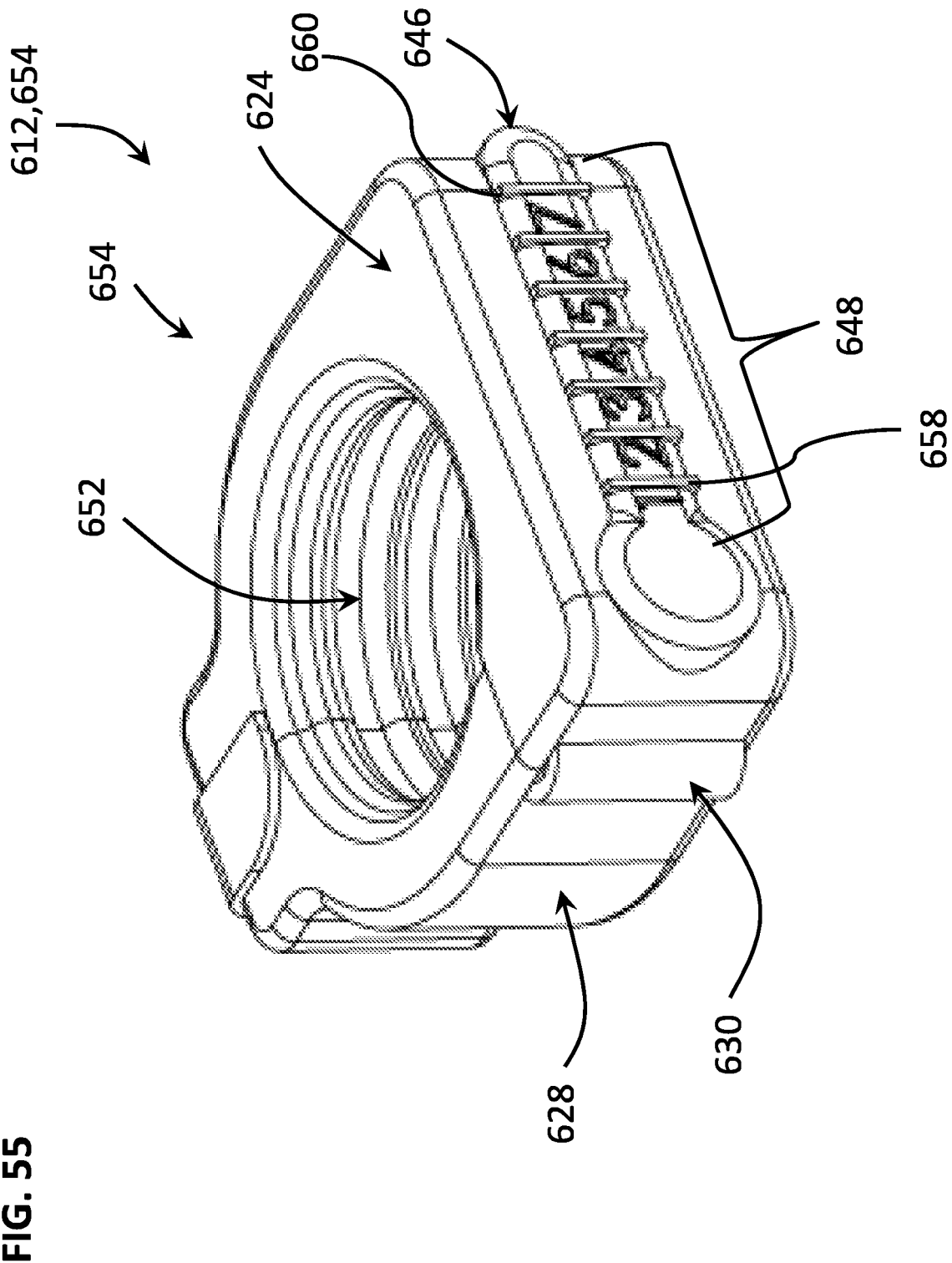
FIG. 55 is an enlarged isometric view of the medical timing device of FIG. 51, illustrating the medical timing device in the closed or locked position.

As illustrated in FIGS. 53-54, in this embodiment, the medical timing device 612 includes: (a) a first portion 624 defining a first tubular channel 626 configured to receive a first portion of the ventilation tube 614; (b) a second portion 628 moveably coupled to the first portion 624 through a hinge 630, wherein the second portion 628 defines a second tubular channel 632 configured to receive a second portion of the ventilation tube 614; (c) a tooth 634 coupled to the first portion 624, wherein the tooth 634 has a ram or driver 636 configured to make contact with, and apply a force to, a timer activation portion 638 (FIG. 54), such as an internal seal or membrane of the timer described below; (d) a locking member 640 of the second portion 628, wherein the locking member 640 defines a lock opening 642 configured to receive the tooth end 644; (e) a display portion 646 coupled to the first portion 624, wherein the display portion 646 displays a series of period markers 648; and (f) a timer having the same structure, functionality and elements as the timer 492 described above.

Referring to FIG. 53, in an embodiment, each of the portions 624, 628 has an interior surface 649. The interior surface 649 defines a plurality of peaks 651 and valleys 653. When the user inserts the ventilation tube 614 into the medical timing device 612, at least one peak 651 fits within one of the valleys 622 (FIG. 52), and at least one valley 653 receives one of the peaks 620 (FIG. 52). This mating engagement between the corrugated exterior surface 618 and the medical timing device 612 inhibits the undesired sliding or movement of the medical timing device 612 along the longitudinal axis of the ventilation tube 614.

To deploy the medical timing device 612, the user separates the portions 624, 628 to achieve the unlocked position 650 illustrated in FIG. 53. Next, the user inserts the ventilation tube 614 into the passageway 652 (FIG. 54) defined collectively by the united channels 626, 632. Next, the user closes the medical timing device 612 to reach the locked position 654 (FIGS. 51-52 and 54-55). In the locked position 654, the interior surface 649 is mated with the corrugated exterior surface 618 as described above. Next, the user applies a single action 54, such as a closing force moving the portions 624, 628 together. In response to such single action 54, multiple outcomes occur. One of the outcomes is that the hook-shaped portion 656 of the tooth end 644 becomes locked together with the locking member 640. This locks the medical timing device 612 onto the ventilation tube 614. Another one of the outcomes is that the tooth end 644 drives into the timer activation portion 638, applying a force to the timer activation portion 638. This force causes the timer to enter into the active mode. In an embodiment, this force ruptures in internal seal or membrane of the timer, causing the timer to change to the active mode for indicating the passage of time. In another embodiment, this force causes the liquid in the timer to diffuse throughout the timer, causing the timer to change to the active mode for indicating the passage of time.

In the active mode, the display portion 646 displays or indicates a continuous indicator (e.g., color contrast), gradually expanding from starting period marker 658 (indicating day one) to the ending period marker 660 (indicating day seven). In this example, ending period marker 660 indicates a seven day usage period, the designated usage period for the ventilation tube 614 or its permanently attached equipment (e.g., endotracheal tube 616).

In certain embodiments described above, such as medical device 58, catheter securement devices 62, 82, catheter securement device 488 and medical timing device 612, multiple outcomes (e.g., locking and timer activation) result from a single action 54. This can provide a significant advantage for users. For example, in the midst of high hospital time pressures, this single step or single action enables a nurse or other clinician to deploy either such device with greater security, speed, ease of use, simplicity and certainty than conventional methods for tracking the in-use time of medical articles.

In other embodiments, the catheter insertion cover 544, medical timing device 572 or alternative embodiments of the medical device 58, catheter securement devices 62, 82, catheter securement device 488, or medical timing device 612 can be configured and operable to perform the locking and timer activation outcomes in response to multiple user actions or steps. In such embodiments, such cover and devices provide advantages of greater security, speed, ease of use, simplicity and certainty than conventional methods for tracking the in-use time of medical articles.

In the examples described above and illustrated in the figures, certain usage periods are described, such as a seven or four day usage period. These periods are only examples. It should be appreciated that the medical community or healthcare industry can convey any suitable standards to establish any designated usage periods for various medical articles.

The locking functionality of the medical device 58, catheter securement devices 62, 82, catheter securement device 488, medical timing device 572 and medical timing device 612 is described above, at times, as being irreversible or permanent. It should be understood that, in some embodiments, this locking functionality enables a technician or user to unlock or open either such device using a suitable tool. Furthermore, it should be understood that, in some embodiments, this locking functionality enables a technician or user to unlock or open either such device by cracking, breaking or damaging such device. In addition, it should be understood that, in some embodiments, this locking functionality enables a technician or user to unlock or open either such device by exerting substantial force, effort or time, such as more than hand force or more than ten seconds of effort.

In an embodiment, the medical device 58, catheter securement device 82, catheter securement device 488, medical timing device 572 and medical timing device 612 are each constructed of a suitable polymer, such as a hard or rigid plastic, a semi-rigid plastic, a synthetic or natural rubber, a foam, a single or stack of polymeric substrates or layers or a suitable metal or combination of the foregoing. Furthermore, in an embodiment, such materials include an antimicrobial additive, antimicrobial characteristic, antibacterial additive or antibacterial characteristic to deter the growth or onset of harmful microbial organisms and bacteria.

Additional embodiments include any one of the embodiments described above, where one or more of its components, functionalities or structures is interchanged with, replaced by or augmented by one or more of the components, functionalities or structures of a different embodiment described above.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

The following is claimed:

1. A medical dressing comprising:
a flexible body comprising a top and a bottom;
an adhesive coupled to the bottom, wherein the adhesive is configured to adhere the bottom to a skin site; and
a window supported by the flexible body, wherein the window comprises a see-through surface configured to cover at least part of the skin site;
a timer coupled to the flexible body, wherein the timer comprises:
a fluid container positioned between the top and the bottom of the flexible body, wherein the fluid container is configured to hold a liquid; and
at least one absorptive layer supported by the flexible body;
a time activation member supported by the flexible body; and
a display portion supported by the flexible body, wherein the display portion comprises a plurality of period markers,
wherein, in response to a force applied to the time activation member:
the fluid container is configured to unseal, causing the liquid to at least partially diffuse through the at least one absorptive layer at a diffusion rate corresponding to a time-tracking function; and
the display portion is configured to indicate a passage of time based on the diffusion rate.

2. The medical dressing of claim 1, wherein:
the skin site comprises a vascular insertion site;
the window is flexible; and
the see-through surface is one of fully transparent, partially transparent, fully translucent, and partially translucent.

3. The medical dressing of claim 1, wherein:
the liquid comprises a color;
the display portion is configured to display the color along a path; and
the path extends at least partially around the window.

4. The medical dressing of claim 1, wherein the fluid container comprises a seal configured to be ruptured in response to the force.

5. The medical dressing of claim 1, wherein:
the timer comprises a stack of absorptive layers, wherein the stack comprises the at least one absorptive layer; and
the stack is associated with a wicking characteristic.

6. The medical dressing of claim 1, wherein the time activation member is a region of the top of the flexible body.

7. The medical dressing of claim 1, wherein the display portion is a region of the top of the flexible body, wherein the region is one of fully transparent, partially transparent, fully translucent, partially translucent, and see-through.

8. The medical dressing of claim 1, wherein:
the display portion defines a path comprising:
a first end located adjacent to the time activation member; and
a second end located opposite of the first end;
the display portion comprises a plurality of period markers between the first and second ends of the path;
the period markers are associated with a designated usage period; and
the period markers comprise: (a) a starting period marker adjacent to the first end of the path; and (b) an ending period marker adjacent to the second end of the path.

9. A medical dressing comprising:
a body comprising a top and a bottom;
a see-through surface supported by the body; and
a timer coupled to the body, wherein the timer comprises a structure configured to track a passage of time based on liquid diffusion,
wherein the top of the body comprises an activation portion, wherein the activation portion is configured to: (a) receive a force; and (b) transmit the force to the structure of the timer,
wherein the top of the body comprises a display portion,
wherein the display portion is configured to indicate the passage of time tracked by the timer.

10. The medical dressing of claim 9, wherein:
the body comprises a flexible structure comprised of one or more layers; and
the medical dressing comprises an adhesive applied to the bottom, wherein the adhesive is configured to adhere the bottom to skin.

11. The medical dressing of claim 9, wherein:
the structure supports a fluid;
the fluid comprises a color;
the display portion is configured to display the color along a path; and
the path extends at least partially around the see-through surface.

12. The medical dressing of claim 9, wherein:
the see-through surface is flexible;
the see-through surface is one of fully transparent, partially transparent, fully translucent, and partially translucent; and
the body defines a slot configured to at least partially receive a portion of a medical catheter.

13. The medical dressing of claim 9, comprising:
a window supported by the body, wherein:
the window comprises the see-through surface;
the see-through surface is configured to cover a portion of a skin site; and
the see-through surface is configured to provide visibility to the portion of the skin site; and
adhesive coupled to the bottom, wherein the adhesive is configured to adhere the bottom to skin surrounding the portion of the skin site.

14. A medical dressing comprising:
a body comprising a top and a bottom;
a see-through surface supported by the body; and
a timer coupled to the body, wherein the timer comprises a structure configured to track a passage of time based on liquid diffusion,
wherein the structure of the timer comprises a fluid container and an absorptive element,
wherein the fluid container is at least partially positioned between the top and the bottom of the body,
wherein the fluid container is configured to contain a fluid that is configured to at least partially diffuse through the absorptive element.

15. The medical dressing of claim 14, comprising:
an activation member configured to: (a) receive a force; and (b) unseal the fluid container in response to the force, wherein the activation member is one of: (i) a portion of the body, (ii) a portion of the top, and (iii) a portion of the timer; and
a display portion configured to indicate the passage of time, wherein the display portion is one of: (i) a portion of the body, (ii) a portion of the top, and (iii) a portion of the timer.

16. The medical dressing of claim 14, comprising:
a window supported by the body, wherein:
the window comprises the see-through surface;
the see-through surface is configured to cover a portion of a skin site; and
the see-through surface is configured to provide visibility to the portion of the skin site; and
adhesive coupled to the bottom, wherein the adhesive is configured to adhere the bottom to skin surrounding the portion of the skin site,
wherein the body defines an opening configured to at least partially receive a part of a medical catheter.

17. A medical dressing comprising:
a body comprising:
a top;
a bottom configured to be secured to a skin site; and
a flexible structure comprised of one or more layers;
a see-through surface supported by the body, wherein the see-through surface provides visibility to at least a portion of the skin site; and
a timer coupled to the body, wherein the timer excludes an electrical power source;
a display portion supported by the body, wherein the display portion is configured to indicate a passage of time based on a function of the timer, wherein:
the structure of the timer comprises a fluid container and an absorptive element;
the fluid container is at least partially positioned between the top and bottom of the body; and
the fluid container is configured to contain a fluid that is configured to at least partially diffuse through the absorptive element.

18. The medical dressing of claim 17, wherein the timer comprises a structure configured to track the passage of time based on liquid diffusion without being powered by a battery.

19. The medical dressing of claim 17, comprising:
an activation member configured to: (a) receive a force; and (b) unseal the fluid container in response to the force, wherein the activation member is one of: (i) a portion of the body, (ii) a portion of the top, and (iii) a portion of the timer; and
the display portion is one of: (i) a portion of the body, (ii) a portion of the top, and (iii) a portion of the timer.

20. The medical dressing of claim 17, wherein:
the see-through surface is positioned within a perimeter;
the display portion is configured to display an indication of the fluid extending along a path; and
the path comprises a curved shape, extending at least partially around the perimeter.

21. The medical dressing of claim 17, comprising:
a window supported by the body, wherein:
  the window comprises the see-through surface; and
  the see-through surface is configured to cover a portion of the skin site; and
adhesive coupled to the bottom, wherein the adhesive is configured to adhere the bottom to skin surrounding the portion of the skin site,
wherein the body defines an opening configured to at least partially receive a part of a medical catheter.

* * * * *